(12) United States Patent
Nakamoto et al.

(10) Patent No.: US 11,834,715 B2
(45) Date of Patent: Dec. 5, 2023

(54) OLIGONUCLEOTIDE-COMPRISING CELLULAR COMPONENT-BINDING REAGENTS AND METHODS OF USING THE SAME

(71) Applicant: Becton, Dickinson and Company, Franklin Lakes, NJ (US)

(72) Inventors: Margaret Nakamoto, Palo Alto, CA (US); Eleen Shum, San Carlos, CA (US); Nidhanjali Bansal, Milpitas, CA (US); Christina Chang, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 21 days.

(21) Appl. No.: 16/748,691

(22) Filed: Jan. 21, 2020

(65) Prior Publication Data

US 2020/0248263 A1 Aug. 6, 2020

Related U.S. Application Data

(60) Provisional application No. 62/852,778, filed on May 24, 2019, provisional application No. 62/797,903, filed on Jan. 28, 2019.

(51) Int. Cl.
*C12Q 1/6883* (2018.01)
*G01N 33/53* (2006.01)

(52) U.S. Cl.
CPC ....... *C12Q 1/6883* (2013.01); *G01N 33/5308* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2004/0219529 A1 | 11/2004 | Reddy et al. |
| 2008/0176233 A1 | 7/2008 | Nilsen et al. |
| 2012/0258880 A1 | 10/2012 | Schwartz et al. |
| 2012/2058881 | 10/2012 | Schwartz et al. |
| 2016/0289769 A1* | 10/2016 | Schwartz ............. C12Q 1/6806 |
| 2018/0088112 A1 | 3/2018 | Fan et al. |
| 2018/0267036 A1 | 9/2018 | Fan et al. |

FOREIGN PATENT DOCUMENTS

| | | |
|---|---|---|
| WO | WO2003031591 A2 | 4/2003 |
| WO | WO2018058073 A2 | 4/2018 |
| WO | WO2019084058 A2 | 5/2019 |
| WO | WO2020028266 A1 | 2/2020 |
| WO | WO2020037065 A1 | 2/2020 |
| WO | WO2020072380 A1 | 4/2020 |

OTHER PUBLICATIONS

Akkaya, et al. "A Simple, Versatile Antibody-Based Barcoding Method for Flow Cytometry", The Journal of Immunology, 2016; 197:2027-2038.
Becton, Dickinson and Company, "BD™ AbSeq on the BD Rhapsody™ system: Exploration of single-cell gene regulation by simultaneous digital mRNA and protein quantification", www.bd.com/genomic, 2018, 7 pages.
Shahi, et al. "Abseq: Ultrahigh-throughput single cell protein profiling with droplet microfluidic barcoding", Sci Rep. 2017;7:44447, 12 pages.
Yeung, et al. "Standardized oligonucleotide barcode antibody conjugates for multiplex immunophenotyping", BioLegend, 2018, 1 page.
Goltsev, et al. "Deep Profiling of Mouse Splenic Architecture with CODEX Multiplexed Imaging", Cell, vol. 174, No. 4, Aug. 9, 2018 (Aug. 9, 2018), pages 968-981.e15.
Peterson, et a. "Multiplexed quantification of proteins and transcripts in single cells", Nature Biotechnology, vol. 35, No. 10, Aug. 30, 2017 (Aug. 30, 2017), pp. 936-939.
Stoeckius, et al. "Simultaneous epitope and transcriptome measurement in single cells", Nature Methods, vol. 14, No. 9, Jul. 31, 2017 (Jul. 31, 2017), pp. 865-868.
Ullal, et al. "Cancer Cell Profiling by Barcoding Allows Multiplexed Protein Analysis in Fine-Needle Aspirates", Science Translational Medicine, vol. 6, No. 219, Jan. 15, 2014 (Jan. 15, 2014), pp. 219ra9-219ra9.

* cited by examiner

*Primary Examiner* — Katherine D Salmon
(74) *Attorney, Agent, or Firm* — Andrew R. Guzman; Bret E. Field; BOZICEVIC, FIELD & FRANCIS LLP

(57) ABSTRACT

Disclosed herein include systems, methods, compositions, and kits for quantitative analysis of a plurality of cellular component targets of cells of interest. In some embodiments, an oligonucleotide associated with a cellular component-binding reagent (e.g., an antibody) is associated with one or more detectable moieties (e.g., luminescent moieties, fluorescent moieties, a phosphorescent moieties). In some embodiments, the presence of the detectable moiety in the binding reagent oligonucleotide enables the cellular component-binding reagent to be employed for both fluorescence analysis (e.g., cell sorting) and sequence analysis (e.g., protein expression profiling).

19 Claims, 14 Drawing Sheets

Specification includes a Sequence Listing.

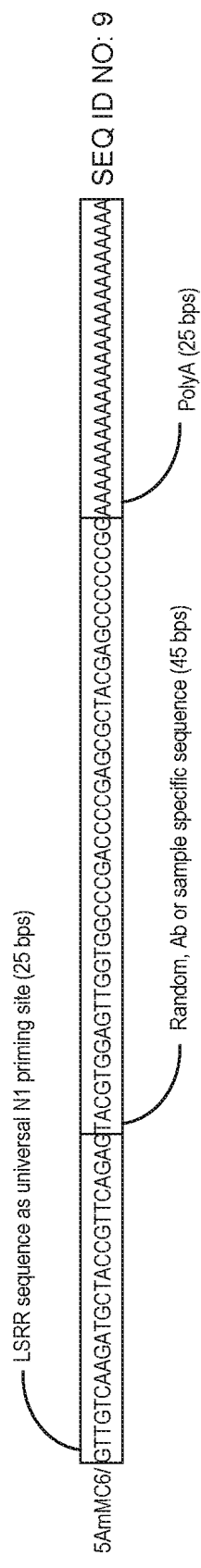
FIG. 10A  95mer oligo design.
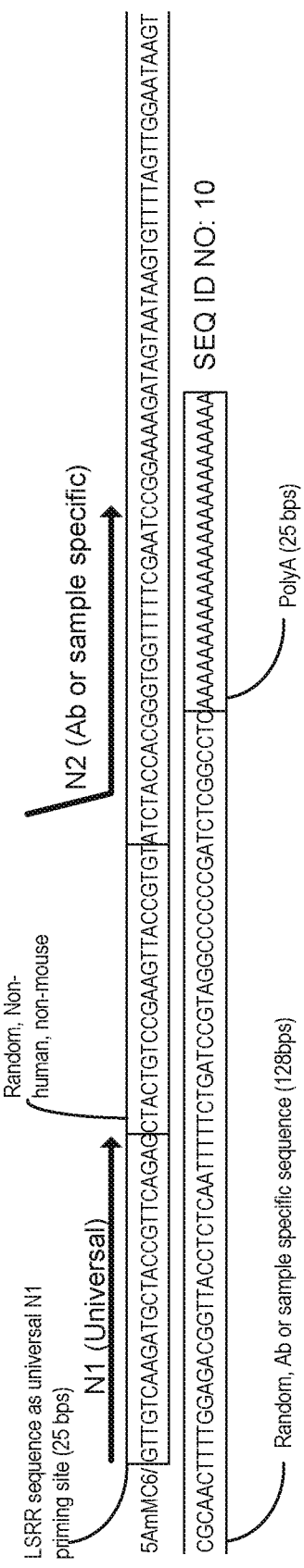
FIG. 10B  200mer oligo design. Targeted amplification scheme (nested specific)

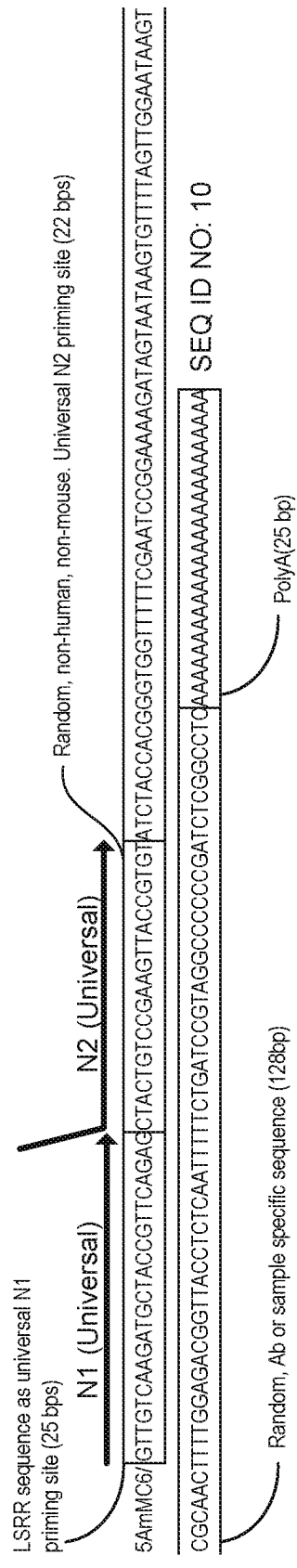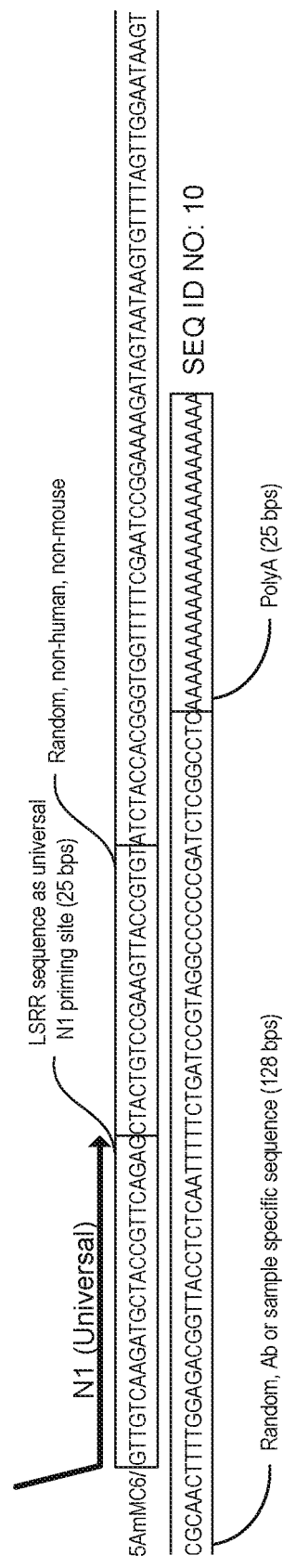

OLIGONUCLEOTIDE-COMPRISING CELLULAR COMPONENT-BINDING REAGENTS AND METHODS OF USING THE SAME

CROSS-REFERENCE TO RELATED APPLICATION

Pursuant to 35 U.S.C. § 119(e), this application claims priority to the filing dates of U.S. Provisional Patent Application Ser. No. 62/797,903 filed Jan. 28, 2019 and 62/852,778 filed May 24, 2019; the disclosures of which applications are incorporated herein by reference.

INTRODUCTION

Field

The present disclosure relates generally to the field of molecular biology, for example identifying cells of different samples and determining protein expression profiles in cells using molecular barcoding.

BACKGROUND

Current technology allows measurement of gene expression of single cells in a massively parallel manner (e.g., >10000 cells) by attaching cell specific oligonucleotide barcodes to poly(A) mRNA molecules from individual cells as each of the cells is co-localized with a barcoded reagent bead in a compartment. Gene expression may affect protein expression. Protein-protein interaction may affect gene expression and protein expression. There is a need for systems and methods that can quantitatively analyze protein expression in cells, and simultaneously measure protein expression and gene expression in cells.

SUMMARY

Disclosed herein include methods of quantitative analysis of a plurality of cellular component targets of cells of interest. In some embodiments, the method comprises: contacting a plurality of cellular component-binding reagents with a plurality of cells of a sample, each cell comprising cellular component targets of a plurality of cellular component targets, for specific binding with the plurality of cellular component targets, wherein each of the plurality of cellular component-binding reagents is associated with a cellular component-binding reagent specific oligonucleotide comprising a detectable moiety and an identifier sequence for the cellular component-binding reagent that the cellular component-binding reagent specific oligonucleotide is associated therewith, and wherein the cellular component-binding reagent is capable of specifically binding to a cellular component target of the plurality of cellular component targets, thereby generating cells of the plurality of cells each associated with cellular component-binding reagents. The method can comprise obtaining cells of interest from the plurality of cells based on the detectable moieties of the cellular component-binding reagent specific oligonucleotides associated with the cellular component-binding reagents, or lack thereof (for example, by positively selecting cells of interest based on presence or absence of the detectable moieties, and by negative depletion of cells not of interest based on the presence or absence of detectable moieties). The method can comprise contacting a plurality of barcodes with the cellular component-binding reagent specific oligonucleotides, or products thereof, associated with the cellular component-binding reagents associated with the cells of interest obtained, wherein each of the plurality of barcodes comprises a target binding region and a molecular label sequence to generate barcodes hybridized to the cellular component-binding reagent specific oligonucleotides, or products thereof. The method can comprise extending the barcodes hybridized to the cellular component-binding reagent specific oligonucleotides to produce a plurality of labeled nucleic acids, wherein each of the labeled nucleic acids comprises an identifier sequence, or a complementary sequence thereof, and a molecular label sequence, or a complementary sequence thereof. The method can comprise obtaining sequence information of the plurality of labeled nucleic acids, complementary sequences thereof, portions thereof, or a combination thereof, to determine the number of copies of each of the cellular component targets of the cellular component-binding reagents associated with each of the cells of interest.

In some embodiments, the detectable moiety comprises a luminescent moiety. In some embodiments, the luminescent moiety comprises a fluorescent moiety, a phosphorescent moiety, or a combination thereof. In some embodiments, obtaining the cells of interest comprises obtaining the cells of interest based on the fluorescent moieties, or the phosphorescent moieties, of the cellular component-binding reagent specific oligonucleotides associated with the cellular component-binding reagents, or lack thereof. In some embodiments, obtaining the cells of interest comprises obtaining the cells of interest flow cytometrically based on the fluorescent moieties, or the phosphorescent moieties, of the cellular component-binding reagent specific oligonucleotides associated with the cellular component-binding reagents, or lack thereof.

Disclosed herein include methods of analyzing a plurality of cellular component targets in a sample. In some embodiments, the method comprises: contacting a plurality of cellular component-binding reagents with a plurality of cells of a sample, each cell comprising cellular component targets of a plurality of cellular component targets, for specific binding with the plurality of cellular component targets, wherein each of the plurality of cellular component-binding reagents is associated with a cellular component-binding reagent specific oligonucleotide comprising a detectable moiety, or a precursor thereof, and an identifier sequence for the cellular component-binding reagent that the cellular component-binding reagent specific oligonucleotide is associated therewith, and wherein the cellular component-binding reagent is capable of specifically binding to a cellular component target of the plurality of cellular component targets, thereby generating cells of the plurality of cells each associated with the cellular component-binding reagents. The method can comprise performing an experiment on the plurality of cells using the moieties of the cellular component-binding reagent specific oligonucleotides associated with the cellular component-binding reagents, or lack thereof, to obtain an experiment result. The method can comprise contacting a plurality of barcodes with the cellular component-binding reagent specific oligonucleotides, or products thereof, associated with the cellular component-binding reagents associated with the cells, wherein each of the plurality of barcodes comprises a target binding region and a molecular label sequence to generate barcodes hybridized to the cellular component-binding reagent specific oligonucleotides, or products thereof. The method can comprise extending the barcodes hybridized to the cellular component-binding reagent specific oligonucleotides to produce a plurality of labeled nucleic acids, wherein each of the labeled nucleic acid comprises an identifier sequence, or a complementary sequence thereof, and a molecular label sequence, or a complementary sequence thereof. The method can comprise obtaining sequence information of the plurality of labeled nucleic acids, complementary sequences thereof, portions thereof, or a combination thereof, to determine the number of copies of each of the cellular component targets of the cellular component-binding reagents associated with the cells generated. The method can comprise performing an analysis of the experiment result of the cells and/or the number of copies of each of the cellular component targets of the cells associated with the cellular component-binding reagents. The method can comprise performing an analysis of the number of copies of each of the cellular component targets of the cells associated with the cellular component-binding reagents based on the experiment result of the cells. The method can comprise performing an analysis of the number of copies of each of the cellular component targets of the cells associated with the cellular component-binding reagents based on the experiment result of the cells. In some embodiments, performing the analysis comprises correlating the experiment result of the cells and the number of copies of each of the cellular component targets of the cells associated with the cellular component-binding reagents.

Disclosed herein include methods of analyzing a plurality of cellular component targets in a sample. In some embodiments, the method comprises: contacting a plurality of cellular component-binding reagents with a plurality of cells of a sample, each cell comprising cellular component targets of a plurality of cellular component targets, for specific binding with the plurality of cellular component targets, wherein each of the plurality of cellular component-binding reagents is associated with a cellular component-binding reagent specific oligonucleotide comprising a detectable moiety, or a precursor thereof, and an identifier sequence for the cellular component-binding reagent that the cellular component-binding reagent specific oligonucleotide is associated therewith, and wherein the cellular component-binding reagent is capable of specifically binding to a cellular component target of the plurality of cellular component targets, thereby generating cells of the plurality of cells each associated with the cellular component-binding reagents. The method can comprise performing an experiment on the plurality of cells using the moieties of the cellular component-binding reagent specific oligonucleotides associated with the cellular component-binding reagents, or lack thereof, to obtain an experiment result. The method can comprise selecting cells of interest from the cells associated with the cellular component-binding reagents based on the experiment result. The method can comprise contacting a plurality of barcodes with the cellular component-binding reagent specific oligonucleotides, or products thereof, associated with the cellular component-binding reagents associated with the cells of interest, wherein each of the plurality of barcodes comprises a target binding region and a molecular label sequence to generate barcodes hybridized to the cellular component-binding reagent specific oligonucleotides, or products thereof. The method can comprise extending the barcodes hybridized to the cellular component-binding reagent specific oligonucleotides to produce a plurality of labeled nucleic acids, wherein each of the labeled nucleic acid comprises an identifier sequence, or a complementary sequence thereof, and a molecular label sequence, or a complementary sequence thereof. The method can comprise obtaining sequence information of the plurality of labeled nucleic acids, complementary sequences thereof, portions thereof, or a combination thereof, to determine the number of copies of each of the cellular component targets of the cellular component-binding reagents associated with the cells of interest.

In some embodiments, performing the experiment comprises performing a microscopy observation of the cells associated with the cellular component-binding reagents using the detectable moieties of the cellular component-binding reagent specific oligonucleotides associated with the cellular component-binding reagents, or lack thereof. In some embodiments, performing the microscopy observation comprises imaging the cells associated with the cellular component-binding reagents using the detectable moieties of the cellular component-binding reagent specific oligonucleotides associated with the cellular component-binding reagents, or lack thereof. In some embodiments, imaging the cells comprises live imaging the cells associated with the cellular component-binding reagents using the detectable moieties of the cellular component-binding reagent specific oligonucleotides associated with the cellular component-binding reagents, or lack thereof. In some embodiments, at least one of the plurality of cellular component-binding reagents comprises a cell membrane-permeable cellular component-binding reagent, wherein contacting the plurality of cellular component-binding reagents with the plurality of cells comprises contacting the cell membrane-permeable cellular component-binding reagent with the plurality of cells, whereby the cell membrane-permeable cellular component-binding reagent is internalized into the cells of the plurality of cells.

Disclosed herein include methods of quantitative analysis of a plurality of cellular component targets in samples. In some embodiments, the method comprises: contacting a plurality of cellular component-binding reagents with a plurality of cellular component targets of a first sample and a second sample for specific binding with the plurality of cellular component targets, wherein each of the plurality of cellular component-binding reagents is associated with a cellular component-binding reagent specific oligonucleotide comprising a detectable moiety, or a precursor thereof, and a identifier sequence for the cellular component-binding reagent that the cellular component-binding reagent specific oligonucleotide is associated therewith, and wherein the cellular component-binding reagent is capable of specifically binding to a cellular component target of the plurality of cellular component targets, thereby generating cellular component targets of the plurality of cellular component targets associated with cellular component-binding reagents. The method can comprise determining a first quantity of the detectable moiety of the cellular component-binding reagent specific oligonucleotide associated with the cellular component-binding reagent associated with each of the plurality of cellular component targets in the first sample. The method can comprise contacting a plurality of barcodes with the cellular component-binding reagent specific oligonucleotides, or products thereof, associated with the cellular component-binding reagents associated with the cellular component targets of the first sample, wherein each of the plurality of barcodes comprises a target binding region and a molecular label sequence to generate barcodes hybridized to the cellular component-binding reagent specific oligonucleotides, or products thereof. The method can comprise extending the barcodes hybridized to the cellular component-binding reagent specific oligonucleotides, or products thereof, associated with the cellular component-binding reagents associated with the cellular component targets of the first sample to produce a plurality of labeled nucleic acids, wherein each of the labeled nucleic acid comprises an identifier sequence, or a complementary sequence thereof, and a molecular label sequence, or a complementary sequence thereof. The method can comprise obtaining sequence information of the plurality of labeled nucleic acids, complementary sequences thereof, portions thereof, or a combination thereof, to determine the number of copies of each of the cellular component targets of the first sample. The method can comprise determining a second quantity of the detectable moiety of the cellular component-binding reagent specific oligonucleotide associated with the cellular component-binding reagent associated with each of the plurality of cellular component targets in the second sample. The method can comprise determining the number of copies of each of the cellular component targets of the second sample based on (1) the first quantity of the detectable moiety of the cellular component-binding reagent specific oligonucleotide associated with the cellular component-binding reagent associated with each of the plurality of cellular component targets in the first sample, (2) the number of copies of each of the cellular component targets of the first sample determined, and (3) the second quantity of the detectable moiety of the cellular component-binding reagent specific oligonucleotide associated with the cellular component-binding reagent associated with each of the plurality of cellular component targets in the second sample.

In some embodiments, the number of copies of each of the cellular component targets of the second sample is inversely proportional to the first quantity of the moiety of the cellular component-binding reagent specific oligonucleotide associated with the cellular component-binding reagent associated with each of the plurality of cellular component targets in the first sample. In some embodiments, the number of copies of each of the cellular component targets of the second sample is directly proportional to the number of copies of each of the cellular component targets of the first sample determined. In some embodiments, the number of copies of each of the cellular component targets of the second sample is directly proportional to the second quantity of the moiety of the cellular component-binding reagent specific oligonucleotide associated with the cellular component-binding reagent associated with each of the plurality of cellular component targets in the second sampled.

In some embodiments, the detectable moiety comprises an optical moiety, a luminescent moiety, an electrochemically active moiety, a nanoparticle, or a combination thereof. In some embodiments, the luminescent moiety comprises a chemiluminescent moiety, an electroluminescent moiety, a photoluminescent moiety, or a combination thereof. In some embodiments, the photoluminescent moiety comprises a fluorescent moiety, a phosphorescent moiety, or a combination thereof. In some embodiments, the fluorescent moiety comprises a fluorescent dye. In some embodiments, the nanoparticle comprises a quantum dot. In some embodiments, the methods comprise performing a reaction to convert the detectable moiety precursor into the detectable moiety.

In some embodiments, the detectable moiety of the cellular component-binding reagent specific oligonucleotide is unique to the cellular component-binding reagent specific oligonucleotide. In some embodiments, the detectable moieties of two cellular component-binding reagent specific oligonucleotides are identical. In some embodiments, the cellular component-binding reagent specific oligonucleotide comprises a second detectable moiety. In some embodiments, the second detectable moiety of the cellular component-binding reagent specific oligonucleotide is unique to the cellular component-binding reagent specific oligonucleotide. In some embodiments, the combination of the detectable moiety and the second detectable moiety of the cellular component-binding reagent specific oligonucleotide is unique to the cellular component-binding reagent specific oligonucleotide. In some embodiments, the sample comprises a tissue section, or cells thereof.

In some embodiments, the methods comprise prior to extending barcodes: partitioning the cells of plurality of cells associated with cellular component-binding reagents to a plurality of partitions (e.g., a microwell, a droplet, etc.), wherein a partition of the plurality of partitions comprises a single cell from the cells associated with the cellular component-binding reagents; in the partition comprising the single cell, contacting a barcoding particle with the cellular component-binding reagent specific oligonucleotides, wherein the barcoding particle comprises the plurality of barcodes, and wherein two barcodes of the plurality of barcodes comprise different molecular label sequences. In some embodiments, at least one barcode of the plurality of barcodes is immobilized on the particle, partially immobilized on the particle, enclosed in the particle, partially enclosed in the particle, or a combination thereof. In some embodiments, the barcoding particle is disruptable. In some embodiments, the particle comprises a bead. In some embodiments, the barcoding particle is a solid bead, a semi-permeable bead, a hydrogel bead, or a combination thereof. In some embodiments, the partition is a well or a droplet.

In some embodiments, the number of unique molecular label sequences associated with the unique identifier sequence for the cellular component-binding reagent capable of specifically binding to the at least one cellular component target in the sequencing data indicates the number of copies of the at least one cellular component target in the one or more of the plurality of cells. In some embodiments, the cellular component-binding reagent specific oligonucleotide comprises the sequence of a first universal primer, a complementary sequence thereof, a partial sequence thereof, or a combination thereof. In some embodiments, the first universal primer is 5-50 nucleotides in length. In some embodiments, the first universal primer comprises an amplification primer, a sequencing primer, or a combination thereof. In some embodiments, the sequencing primer comprises a P7 sequencing primer. In some embodiments, obtaining sequencing information of the plurality of labeled nucleic acids or a portion thereof comprises subjecting the labeled nucleic acids to one or more reactions to generate a set of nucleic acids for nucleic acid sequencing. In some embodiments, each of the barcodes comprises a cell label, a second universal primer, an amplification adaptor, a sequencing adaptor, or a combination thereof. In some embodiments, subjecting the labeled nucleic acids to the one or more reactions comprises subjecting the labeled nucleic acids to an amplification reaction, using the first universal primer, a first primer comprising the sequence of the first universal primer, the second universal primer, a second primer comprising the sequence of the second universal primer, or a combination thereof, to generate the set of nucleic acids for nucleic acid sequencing.

In some embodiments, the cellular component-binding reagent specific oligonucleotide is associated with the cellular component-binding reagent through a linker. In some embodiments, the linker comprises a carbon chain. In some embodiments, the carbon chain comprises 2-30 carbons. In some embodiments, the plurality of cellular component targets comprises a plurality of protein targets, and wherein the cellular component-binding reagent is capable of specifically binding to a protein target of the plurality of protein targets. In some embodiments, the cellular component-binding reagent specific oligonucleotide is covalently attached to the cellular component-binding reagent. In some embodiments, the cellular component-binding reagent specific oligonucleotide is conjugated to the cellular component-binding reagent. In some embodiments, the cellular component-binding reagent specific oligonucleotide is conjugated to the cellular component-binding reagent through a chemical group selected from the group consisting of a UV photocleavable group, a streptavidin, a biotin, an amine, and a combination thereof. In some embodiments, the cellular component-binding reagent specific oligonucleotide is non-covalently attached to the cellular component-binding reagent. In some embodiments, the cellular component-binding reagent specific oligonucleotide is configured to be detachable from the cellular component-binding reagent.

In some embodiments, the methods comprise dissociating the cellular component-binding reagent specific oligonucleotide from the cellular component-binding reagent. In some embodiments, dissociating the cellular component-binding reagent specific oligonucleotide comprises detaching the cellular component-binding reagent specific oligonucleotide from the cellular component-binding reagent by UV photocleaving, chemical treatment, heating, enzyme treatment, or any combination thereof. In some embodiments, the dissociating occurs after barcoding the cellular component-binding reagent specific oligonucleotide. In some embodiments, the dissociating occurs before barcoding the cellular component-binding reagent specific oligonucleotide. In some embodiments, the cellular component-binding reagent specific oligonucleotide is configured to be non-detachable from the cellular component-binding reagent.

In some embodiments, the cellular component-binding reagent specific oligonucleotide comprises a sequence complementary to a capture sequence of a barcode configured to capture the sequence of the cellular component-binding reagent specific oligonucleotide. In some embodiments, the barcode comprises a target-binding region which comprises the capture sequence. In some embodiments, the target-binding region comprises a poly(dT) region. In some embodiments, the sequence of the cellular component-binding reagent specific oligonucleotide complementary to the capture sequence comprises a poly(dA) region.

In some embodiments, the methods comprise after contacting the plurality of cellular component-binding reagents with the plurality of cells, removing one or more cellular component-binding reagents of the plurality of cellular component-binding reagents that are not contacted with the plurality of cells. In some embodiments, removing the one or more cellular component-binding reagents not contacted with the plurality of cells comprises: removing the one or more cellular component-binding reagents not contacted with the respective at least one of the plurality of cellular component targets. In some embodiments, partitioning the plurality of cells comprises partitioning the plurality of cells associated with the plurality of cellular component-binding reagents and a plurality of barcoding particles comprising the barcoding particle to the plurality of partitions, wherein the partition of the plurality of partitions comprises the single cell from the plurality of cells associated with the cellular component-binding reagent and the barcoding particle. In some embodiments, the plurality of cellular component targets comprises a cell-surface protein, an intracellular protein, a cell marker, a B-cell receptor, a T-cell receptor, an antibody, a major histocompatibility complex, a tumor antigen, a receptor, or a combination thereof. In some embodiments, the plurality of cells comprises T cells, B cells, tumor cells, myeloid cells, blood cells, normal cells, fetal cells, maternal cells, or a mixture thereof.

In some embodiments, the cell membrane-permeable cellular component-binding reagent can be internalized into the one or more cells by diffusion through the cell membranes of the cells. The method can comprise permeabilizing cell membranes of the one or more cells. Permeabilizing the cell membranes of the cells comprises permeabilizing the cell membranes of the one or more cells using a detergent. The cell membrane-permeable reagent can internalize into the cells via one or more membrane transporter proteins of the one or more cells.

In some embodiments, the cell membrane-permeable cellular component-binding reagent comprises an organic molecule, a peptide, a lipid, or a combination thereof. The organic molecule can comprise a cell-membrane permeable organic molecule. The organic molecule can comprise a dye. The organic molecule can comprise a fluorescent dye. The organic molecule can comprise a ring structure. The ring structure can comprise 5-50 carbon atoms. The organic molecule can comprise a carbon chain. The carbon chain can comprise 5-50 carbon atoms. The organic molecule can be converted into a second organic molecule after being internalized into the one or more cells. The organic molecule can be acetoxymethyl calcein (calcein AM), and wherein the second organic molecule is calcein.

In some embodiments, the peptide can comprise a cell membrane-permeable peptide. The peptide can be 5-30 amino acids in length. The cell membrane-permeable reagent can insert into the cell membranes of the cells. The cell membrane-permeable cellular component-binding reagent can comprise a lipid.

Disclosed herein include methods of determining whether a cellular constituent in a sample comprises a cellular component target of interest. Aspects of the methods include: producing a detectably labeled sample comprising a cellular component-binding reagent, wherein the cellular component-binding reagent is associated with a cellular component-binding reagent specific oligonucleotide associated with a detectable moiety and comprising an identifier sequence for the cellular component-binding reagent with which the cellular component-binding reagent specific oligonucleotide is associated, and wherein the cellular component-binding reagent is capable of specifically binding to the cellular component target of interest; and assaying cellular constituents of the detectably labeled sample for the detectable moiety to determine whether a cellular constituent in a cellular sample comprises the cellular component target of interest. Embodiments of such methods further include separating cellular constituents that comprise the cellular component target of interest from other constituents of the cellular sample. In some instances the methods further comprise isolating a cellular constituent that comprises the cellular component target of interest into a single cell sample, e.g., in a partition. In some instances, the methods further comprise producing barcoded identifier sequences from the single cell sample. In some instances, the methods further comprise sequencing the barcoded identifier sequences to obtain sequence information for the single cell sample. In some instances, the methods further comprise quantitating the cellular component target of interest for the cellular constituent of the single cell sample from the sequence information. In some instances, the methods further comprise transcriptome analysis of the cellular constituents of the cellular sample that comprise the cellular component target of interest.

BRIEF DESCRIPTION OF THE DRAWINGS

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

FIGS. 10A-10D show non-limiting exemplary designs of oligonucleotides for determining protein expression and gene expression simultaneously and for sample indexing.

DEFINITIONS

Figure 1:
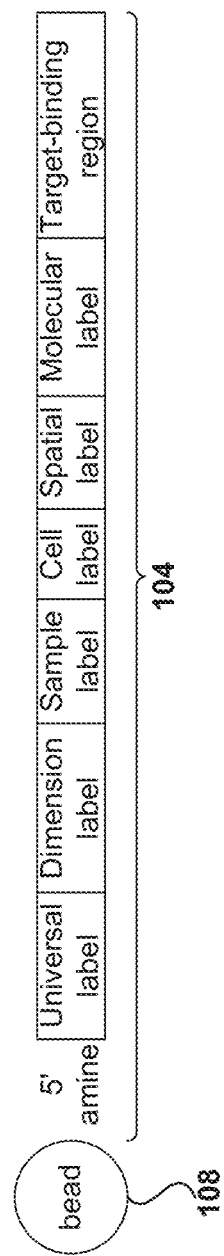
FIG. 1 illustrates a non-limiting exemplary stochastic barcode.

Unless defined otherwise, technical and scientific terms used herein have the same meaning as commonly understood by one of ordinary skill in the art to which the present disclosure belongs. See, e.g., Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, the term "adaptor" can mean a sequence to facilitate amplification or sequencing of associated nucleic acids. The associated nucleic acids can comprise target nucleic acids. The associated nucleic acids can comprise one or more of spatial labels, target labels, sample labels, indexing label, or barcode sequences (e.g., molecular labels). The adapters can be linear. The adaptors can be pre-adenylated adapters. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adapter can, in some embodiments, comprise a universal sequence. A universal sequence can be a region of nucleotide sequence that is common to two or more nucleic acid molecules. The two or more nucleic acid molecules can also have regions of different sequence. Thus, for example, the 5' adapters can comprise identical and/or universal nucleic acid sequences and the 3' adapters can comprise identical and/or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize to such a universal sequence. The target nucleic acid sequence-bearing molecules may be modified to attach universal adapters (e.g., non-target nucleic acid sequences) to one or both ends of the different target nucleic acid sequences. The one or more universal primers attached to the target nucleic acid can provide sites for hybridization of universal primers. The one or more universal primers attached to the target nucleic acid can be the same or different from each other.

As used herein, an antibody can be a full-length (e.g., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

In some embodiments, an antibody is a functional antibody fragment. For example, an antibody fragment can be a portion of an antibody such as F(ab')2, Fab', Fab, Fv, sFv and the like. An antibody fragment can bind with the same antigen that is recognized by the full-length antibody. An antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (for example, CD8, CD34, and CD45), and therapeutic antibodies.

As used herein the term "associated" or "associated with" can mean that two or more species are identifiable as being co-located at a point in time. An association can mean that two or more species are or were within a similar container. An association can be an informatics association. For example, digital information regarding two or more species can be stored and can be used to determine that one or more of the species were co-located at a point in time. An association can also be a physical association. In some embodiments, two or more associated species are "tethered", "attached", or "immobilized" to one another or to a common solid or semisolid surface. An association may refer to covalent or non-covalent means for attaching labels to solid or semi-solid supports such as beads. An association may be a covalent bond between a target and a label. An association can comprise hybridization between two molecules (such as a target molecule and a label).

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, the terms "complement", "complementary", and "reverse complement" can be used interchangeably. It is understood from the disclosure that if a molecule can hybridize to another molecule it may be the complement of the molecule that is hybridizing.

As used herein, the term "digital counting" can refer to a method for estimating a number of target molecules in a sample. Digital counting can include the step of determining a number of unique labels that have been associated with targets in a sample. This methodology, which can be stochastic in nature, transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "non-depleting reservoirs" can refer to a pool of barcodes (e.g., stochastic barcodes) made up of many different labels. A non-depleting reservoir can comprise large numbers of different barcodes such that when the non-depleting reservoir is associated with a pool of targets each target is likely to be associated with a unique barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of barcodes detected then allows calculation of the number of target molecules present in the original collection or sample. When the ratio of the number of copies of a target molecule present to the number of unique barcodes is low, the labeled target molecules are highly unique (i.e., there is a very low probability that more than one target molecule will have been labeled with a given label).

As used herein, the term "nucleic acid" refers to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g., altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide", "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkyl phosphotriesters, methyl and other alkyl phosphonate such as 3'-alkylene phosphonates, 5'-alkylene phosphonates, chiral phosphonates, phosphinates, phosphoramidates including 3'-amino phosphoramidate and aminoalkyl phosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (e.g., morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene (—$CH_2$), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g., adenine (A) and guanine (G)), and the pyrimidine bases, (e.g., thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5, 4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g., 9-(2-aminoethoxy)-H-pyrimido(5,4-(b) (1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g., 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo[2,3-d]pyrimidin-2-one).

As used herein, the term "sample" can refer to a composition comprising targets. Suitable samples for analysis by the disclosed methods, devices, and systems include cells, tissues, organs, or organisms.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of barcodes (e.g., stochastic barcodes) may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A bead can be non-spherical in shape. A plurality of solid supports spaced in an array may not comprise a substrate. A solid support may be used interchangeably with the term "bead."

As used herein, the term "stochastic barcode" can refer to a polynucleotide sequence comprising labels of the present disclosure. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "gene-specific stochastic barcode" can refer to a polynucleotide sequence comprising labels and a target-binding region that is gene-specific. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets. As used herein, the term "stochastic barcoding" can be used interchangeably with "stochastic labeling."

As used here, the term "target" can refer to a composition which can be associated with a barcode (e.g., a stochastic barcode). Exemplary suitable targets for analysis by the disclosed methods, devices, and systems include oligonucleotides, DNA, RNA, mRNA, microRNA, tRNA, and the like. Targets can be single or double stranded. In some embodiments, targets can be proteins, peptides, or polypeptides. In some embodiments, targets are lipids. As used herein, "target" can be used interchangeably with "species."

As used herein, the term "reverse transcriptases" can refer to a group of enzymes having reverse transcriptase activity (i.e., that catalyze synthesis of DNA from a RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transcriptases, and group II intron reverse transcriptases. Examples of group II intron reverse transcriptases include the *Lactococcus lactis* Ll.LtrB intron reverse transcriptase, the *Thermosynechococcus elongatus* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

The terms "universal adaptor primer," "universal primer adaptor" or "universal adaptor sequence" are used interchangeably to refer to a nucleotide sequence that can be used to hybridize to barcodes (e.g., stochastic barcodes) to generate gene-specific barcodes. A universal adaptor sequence can, for example, be a known sequence that is universal across all barcodes used in methods of the disclosure. For example, when multiple targets are being labeled using the methods disclosed herein, each of the target-specific sequences may be linked to the same universal adaptor sequence. In some embodiments, more than one universal adaptor sequences may be used in the methods disclosed herein. For example, when multiple targets are being labeled using the methods disclosed herein, at least two of the target-specific sequences are linked to different universal adaptor sequences. A universal adaptor primer and its complement may be included in two oligonucleotides, one of which comprises a target-specific sequence and the other comprises a barcode. For example, a universal adaptor sequence may be part of an oligonucleotide comprising a target-specific sequence to generate a nucleotide sequence that is complementary to a target nucleic acid. A second oligonucleotide comprising a barcode and a complementary sequence of the universal adaptor sequence may hybridize with the nucleotide sequence and generate a target-specific barcode (e.g., a target-specific stochastic barcode). In some embodiments, a universal adaptor primer has a sequence that is different from a universal PCR primer used in the methods of this disclosure.

DETAILED DESCRIPTION

Disclosed herein include methods of quantitative analysis of a plurality of cellular component targets of cells of interest. In some embodiments, the method comprises: contacting a plurality of cellular component-binding reagents with a plurality of cells of a sample, each cell comprising cellular component targets of a plurality of cellular component targets, for specific binding with the plurality of cellular component targets, wherein one or more of, including each of, the plurality of cellular component-binding reagents is associated with a cellular component-binding reagent specific oligonucleotide comprising a detectable moiety and an identifier sequence for the cellular component-binding reagent that the cellular component-binding reagent specific oligonucleotide is associated therewith, and wherein the cellular component-binding reagent is capable of specifically binding to a cellular component target of the plurality of cellular component targets, thereby generating cells of the plurality of cells each associated with cellular component-binding reagents; obtaining cells of interest from the plurality of cells based on the detectable moieties of the cellular component-binding reagent specific oligonucleotides associated with the cellular component-binding reagents, or lack thereof; contacting a plurality of barcodes with the cellular component-binding reagent specific oligonucleotides, or products thereof, associated with the cellular component-binding reagents associated with the cells of interest obtained, wherein each of the plurality of barcodes comprises a target binding region and a molecular label sequence to generate barcodes hybridized to the cellular component-binding reagent specific oligonucleotides, or products thereof; extending the barcodes hybridized to the cellular component-binding reagent specific oligonucleotides to produce a plurality of labeled nucleic acids, wherein each of the labeled nucleic acids comprises an identifier sequence, or a complementary sequence thereof, and/or a molecular label sequence, or a complementary sequence thereof; and obtaining sequence information of the plurality of labeled nucleic acids, complementary sequences thereof, portions thereof, or a combination thereof, to determine the number of copies of each of the cellular component targets of the cellular component-binding reagents associated with each of the cells of interest.

Disclosed herein include methods of analyzing a plurality of cellular component targets in a sample. In some embodiments, the method comprises: contacting a plurality of cellular component-binding reagents with a plurality of cells of a sample, each cell comprising cellular component targets of a plurality of cellular component targets, for specific binding with the plurality of cellular component targets, wherein one or more of, including each of, the plurality of cellular component-binding reagents is associated with a cellular component-binding reagent specific oligonucleotide comprising a detectable moiety, or a precursor thereof, and an identifier sequence for the cellular component-binding reagent that the cellular component-binding reagent specific oligonucleotide is associated therewith, and wherein the cellular component-binding reagent is capable of specifically binding to a cellular component target of the plurality of cellular component targets, thereby generating cells of the plurality of cells each associated with the cellular component-binding reagents; performing an experiment on the plurality of cells using the moieties of the cellular component-binding reagent specific oligonucleotides associated with the cellular component-binding reagents, or lack thereof, to obtain an experiment result; contacting a plurality of barcodes with the cellular component-binding reagent specific oligonucleotides, or products thereof, associated with the cellular component-binding reagents associated with the cells, wherein each of the plurality of barcodes comprises a target binding region and a molecular label sequence to generate barcodes hybridized to the cellular component-binding reagent specific oligonucleotides, or products thereof; extending the barcodes hybridized to the cellular component-binding reagent specific oligonucleotides to produce a plurality of labeled nucleic acids, wherein each of the labeled nucleic acid comprises an identifier sequence, or a complementary sequence thereof, and a molecular label sequence, or a complementary sequence thereof; and/or obtaining sequence information of the plurality of labeled nucleic acids, complementary sequences thereof, portions thereof, or a combination thereof, to determine the number of copies of each of the cellular component targets of the cellular component-binding reagents associated with the cells generated. The method can comprise performing an analysis of the experiment result of the cells and the number of copies of each of the cellular component targets of the cells associated with the cellular component-binding reagents; performing an analysis of the number of copies of each of the cellular component targets of the cells associated with the cellular component-binding reagents based on the experiment result of the cells; performing an analysis of the number of copies of each of the cellular component targets of the cells associated with the cellular component-binding reagents based on the experiment result of the cells, or a combination thereof.

Disclosed herein include methods of analyzing a plurality of cellular component targets in a sample. In some embodiments, the method comprises: contacting a plurality of cellular component-binding reagents with a plurality of cells of a sample, each cell comprising cellular component targets of a plurality of cellular component targets, for specific binding with the plurality of cellular component targets, wherein one or more of, including each of, the plurality of cellular component-binding reagents is associated with a cellular component-binding reagent specific oligonucleotide comprising a detectable moiety, or a precursor thereof, and an identifier sequence for the cellular component-binding reagent that the cellular component-binding reagent specific oligonucleotide is associated therewith, and wherein the cellular component-binding reagent is capable of specifically binding to a cellular component target of the plurality of cellular component targets, thereby generating cells of the plurality of cells each associated with the cellular component-binding reagents; performing an experiment on the plurality of cells using the moieties of the cellular component-binding reagent specific oligonucleotides associated with the cellular component-binding reagents, or lack thereof, to obtain an experiment result; selecting cells of interest from the cells associated with the cellular component-binding reagents based on the experiment result; contacting a plurality of barcodes with the cellular component-binding reagent specific oligonucleotides, or products thereof, associated with the cellular component-binding reagents associated with the cells of interest, wherein each of the plurality of barcodes comprises a target binding region and a molecular label sequence to generate barcodes hybridized to the cellular component-binding reagent specific oligonucleotides, or products thereof; extending the barcodes hybridized to the cellular component-binding reagent specific oligonucleotides to produce a plurality of labeled nucleic acids, wherein each of the labeled nucleic acid comprises an identifier sequence, or a complementary sequence thereof, and a molecular label sequence, or a complementary sequence thereof; and/or obtaining sequence information of the plurality of labeled nucleic acids, complementary sequences thereof, portions thereof, or a combination thereof, to determine the number of copies of each of the cellular component targets of the cellular component-binding reagents associated with the cells of interest.

Disclosed herein include methods of quantitative analysis of a plurality of cellular component targets in samples. In some embodiments, the methods comprise: contacting a plurality of cellular component-binding reagents with a plurality of cellular component targets of a first sample and a second sample for specific binding with the plurality of cellular component targets, wherein one or more of, including each of, the plurality of cellular component-binding reagents is associated with a cellular component-binding reagent specific oligonucleotide comprising a detectable moiety, or a precursor thereof, and a identifier sequence for the cellular component-binding reagent that the cellular component-binding reagent specific oligonucleotide is associated therewith, and wherein the cellular component-binding reagent is capable of specifically binding to a cellular component target of the plurality of cellular component targets, thereby generating cellular component targets of the plurality of cellular component targets associated with cellular component-binding reagents; determining a first quantity of the detectable moiety of the cellular component-binding reagent specific oligonucleotide associated with the cellular component-binding reagent associated with each of the plurality of cellular component targets in the first sample; contacting a plurality of barcodes with the cellular component-binding reagent specific oligonucleotides, or products thereof, associated with the cellular component-binding reagents associated with the cellular component targets of the first sample, wherein each of the plurality of barcodes comprises a target binding region and a molecular label sequence to generate barcodes hybridized to the cellular component-binding reagent specific oligonucleotides, or products thereof; extending the barcodes hybridized to the cellular component-binding reagent specific oligonucleotides, or products thereof, associated with the cellular component-binding reagents associated with the cellular component targets of the first sample to produce a plurality of labeled nucleic acids, wherein each of the labeled nucleic acid comprises an identifier sequence, or a complementary sequence thereof, and a molecular label sequence, or a complementary sequence thereof; obtaining sequence information of the plurality of labeled nucleic acids, complementary sequences thereof, portions thereof, or a combination thereof, to determine the number of copies of each of the cellular component targets of the first sample; determining a second quantity of the detectable moiety of the cellular component-binding reagent specific oligonucleotide associated with the cellular component-binding reagent associated with each of the plurality of cellular component targets in the second sample; and/or determining the number of copies of each of the cellular component targets of the second sample based on (1) the first quantity of the detectable moiety of the cellular component-binding reagent specific oligonucleotide associated with the cellular component-binding reagent associated with each of the plurality of cellular component targets in the first sample, (2) the number of copies of each of the cellular component targets of the first sample determined, and (3) the second quantity of the detectable moiety of the cellular component-binding reagent specific oligonucleotide associated with the cellular component-binding reagent associated with each of the plurality of cellular component targets in the second sample.

Disclosed herein include methods of determining whether a cellular constituent in a sample comprises a cellular component target of interest. Aspects of the methods include: producing a detectably labeled sample comprising a cellular component-binding reagent, wherein the cellular component-binding reagent is associated with a cellular component-binding reagent specific oligonucleotide associated with a detectable moiety and comprising an identifier sequence for the cellular component-binding reagent with which the cellular component-binding reagent specific oligonucleotide is associated, and wherein the cellular component-binding reagent is capable of specifically binding to the cellular component target of interest; and assaying cellular constituents of the detectably labeled sample for the detectable moiety to determine whether a cellular constituent in a cellular sample comprises the cellular component target of interest. Embodiments of such methods further include separating cellular constituents that comprise the cellular component target of interest from other constituents of the cellular sample. In some instances the methods further comprise isolating a cellular constituent that comprises the cellular component target of interest into a single cell sample, e.g., in a partition. In some instances, the methods further comprise producing barcoded identifier sequences from the single cell sample. In some instances, the methods further comprise sequencing the barcoded identifier sequences to obtain sequence information for the single cell sample. In some instances, the methods further comprise quantitating the cellular component target of interest for the cellular constituent of the single cell sample from the sequence information. In some instances, the methods further comprise transcriptome analysis of the cellular constituents of the cellular sample that comprise the cellular component target of interest.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

In further describing various aspects of the invention, various protocols and reagents/systems used therein are reviewed first in greater detail, following by an in-depth review of the various methods of the invention as well as a description of embodiments of kits that find use in practicing various embodiments of the methods.

Protocols and Reagents/Systems

Various protocols, reagents and systems find use in embodiments of methods of invention. These protocols, reagents and systems include barcodes and digital counting, substrates and microwell arrays, methods of barcoding, cellular component-binding reagents associated with oligonucleotides, association of barcodes, determining the number or presence of unique molecular label sequences, flow cytometry, next generation sequencing, partitioning, cell permeation and detectable moieties. Each of these is further reviewed in greater detail below.

Barcodes and Digital Counting

Quantifying small numbers of nucleic acids, for example messenger ribonucleotide acid (mRNA) molecules, is clinically important for determining, for example, the genes that are expressed in a cell at different stages of development or under different environmental conditions. However, it can also be very challenging to determine the absolute number of nucleic acid molecules (e.g., mRNA molecules), especially when the number of molecules is very small. One method to determine the absolute number of molecules in a sample is digital polymerase chain reaction (PCR). Ideally, PCR produces an identical copy of a molecule at each cycle. However, PCR can have disadvantages such that each molecule replicates with a stochastic probability, and this probability varies by PCR cycle and gene sequence, resulting in amplification bias and inaccurate gene expression measurements. Stochastic barcodes with unique molecular labels (also referred to as molecular indexes (MIs)) can be used to count the number of molecules and correct for amplification bias. Stochastic barcoding such as the Precise™ assay (Cellular Research, Inc. (Palo Alto, CA)) can correct for bias induced by PCR and library preparation steps by using molecular labels (MLs) to label mRNAs during reverse transcription (RT).

The Precise™ assay can utilize a non-depleting pool of stochastic barcodes with large number, for example 6561 to 65536, unique molecular labels on poly(T) oligonucleotides to hybridize to all poly(A)-mRNAs in a sample during the RT step. A stochastic barcode can comprise a universal PCR priming site. During RT, target gene molecules react randomly with stochastic barcodes. Each target molecule can hybridize to a stochastic barcode resulting to generate stochastically barcoded complementary ribonucleotide acid (cDNA) molecules). After labeling, stochastically barcoded cDNA molecules from microwells of a microwell plate, a droplet or other partition, can be pooled into a single tube for PCR amplification and sequencing, e.g., via a next generation sequencing protocol, e.g., as described below. Raw sequencing data can be analyzed to produce the number of reads, the number of stochastic barcodes with unique molecular labels, and the numbers of mRNA molecules.

Barcoding, such as stochastic barcoding, has been described in, for example, Fu et al., *Proc Natl Acad Sci U.S.A.*, 2011 May 31, 108(22):9026-31; U.S. Patent Application Publication No. US2011/0160078; Fan et al., *Science*, 2015 Feb. 6, 347(6222):1258367; US Patent Application Publication No. US2015/0299784; PCT Application Publication No. WO2015/031691 the content of each of these, including any supporting or supplemental information or material, is incorporated herein by reference in its entirety. In some embodiments, the barcode disclosed herein can be a stochastic barcode which can be a polynucleotide sequence that may be used to stochastically label (e.g., barcode, tag) a target. Barcodes can be referred to stochastic barcodes if the ratio of the number of different barcode sequences of the stochastic barcodes and the number of occurrence of any of the targets to be labeled can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be a mRNA species comprising mRNA molecules with identical or nearly identical sequence, an antibody identifier sequence, etc. Barcodes can be referred to as stochastic barcodes if the ratio of the number of different barcode sequences of the stochastic barcodes and the number of occurrence of any of the targets to be labeled is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1. Barcode sequences of stochastic barcodes can be referred to as molecular labels.

A barcode, for example a stochastic barcode, can comprise one or more labels. Exemplary labels can include a universal label, a cell label, a barcode sequence (e.g., a molecular label), a sample label, a plate label, a spatial label, and/or a pre-spatial label. FIG. 1 illustrates an exemplary barcode 104 with a spatial label. The barcode 104 can comprise a 5' amine that may link the barcode to a solid support 108. The barcode can comprise a universal label, a dimension label, a spatial label, a cell label, and/or a molecular label. The order of different labels (including but not limited to the universal label, the dimension label, the spatial label, the cell label, and the molecule label) in the barcode can vary. For example, as shown in FIG. 1, the universal label may be the 5'-most label, and the molecular label may be the 3'-most label. The spatial label, dimension label, and the cell label may be in any order. In some embodiments, the universal label, the spatial label, the dimension label, the cell label, and the molecular label are in any order. The barcode can comprise a target-binding region. The target-binding region can interact with a target (e.g., target nucleic acid, RNA, mRNA, DNA) in a sample. For example, a target-binding region can comprise an oligo (dT) sequence which can interact with poly(A) tails of mRNAs and/or cellular component-binding reagent specific oligonucleotide, etc. In some instances, the labels of the barcode (e.g., universal label, dimension label, spatial label, cell label, and barcode sequence) may be separated by 1, 2, 3, 4, 5, 6, 7, 8, 9, 10, 11, 12, 13, 14, 15, 16, 17, 18, 19, or 20 or more nucleotides.

A label, for example the cell label, can comprise a unique set of nucleic acid sub-sequences of defined length, e.g., seven nucleotides each (equivalent to the number of bits used in some Hamming error correction codes), which can be designed to provide error correction capability. The set of error correction sub-sequences comprise seven nucleotide sequences can be designed such that any pairwise combination of sequences in the set exhibits a defined "genetic distance" (or number of mismatched bases), for example, a set of error correction sub-sequences can be designed to exhibit a genetic distance of three nucleotides. In this case, review of the error correction sequences in the set of sequence data for labeled target nucleic acid molecules (described more fully below) can allow one to detect or correct amplification or sequencing errors. In some embodiments, the length of the nucleic acid sub-sequences used for creating error correction codes can vary, for example, they can be, or be about 1, 2, 3, 4, 5, 6, 7, 8, 9, 10, 15, 20, 30, 31, 40, 50, or a number or a range between any two of these values, nucleotides in length. In some embodiments, nucleic acid sub-sequences of other lengths can be used for creating error correction codes.

Universal Labels

A barcode can comprise one or more universal labels. In some embodiments, the one or more universal labels can be the same for all barcodes in the set of barcodes attached to a given solid support. In some embodiments, the one or more universal labels can be the same for all barcodes attached to a plurality of beads. In some embodiments, a universal label can comprise a nucleic acid sequence that is capable of hybridizing to a sequencing primer. Sequencing primers can be used for sequencing barcodes comprising a universal label. Sequencing primers (e.g., universal sequencing primers) can comprise sequencing primers associated with high-throughput sequencing platforms. In some embodiments, a universal label can comprise a nucleic acid sequence that is capable of hybridizing to a PCR primer. In some embodiments, the universal label can comprise a nucleic acid sequence that is capable of hybridizing to a sequencing primer and a PCR primer. The nucleic acid sequence of the universal label that is capable of hybridizing to a sequencing or PCR primer can be referred to as a primer binding site. A universal label can comprise a sequence that can be used to initiate transcription of the barcode. A universal label can comprise a sequence that can be used for extension of the barcode or a region within the barcode. A universal label can be, or be about, 1, 2, 3, 4, 5, 10, 15, 20, 25, 30, 35, 40, 45, 50, or a number or a range between any two of these values, nucleotides in length. For example, a universal label can comprise at least about 10 nucleotides. A universal label can be at least, or be at most, 1, 2, 3, 4, 5, 10, 15, 20, 25, 30, 35, 40, 45, 50, 100, 200, or 300 nucleotides in length. In some embodiments, a cleavable linker or modified nucleotide can be part of the universal label sequence to enable the barcode to be cleaved off from the support.

Dimension Labels

A barcode can comprise one or more dimension labels. In some embodiments, a dimension label can comprise a nucleic acid sequence that provides information about a dimension in which the labeling (e.g., stochastic labeling) occurred. For example, a dimension label can provide information about the time at which a target was barcoded. A dimension label can be associated with a time of barcoding (e.g., stochastic barcoding) in a sample. A dimension label can be activated at the time of labeling. Different dimension labels can be activated at different times. The dimension label provides information about the order in which targets, groups of targets, and/or samples were barcoded. For example, a population of cells can be barcoded at the G0 phase of the cell cycle. The cells can be pulsed again with barcodes (e.g., stochastic barcodes) at the G1 phase of the cell cycle. The cells can be pulsed again with barcodes at the S phase of the cell cycle, and so on. Barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be labeled before and/or after treatment with a drug and/or therapy. The changes in the number of copies of distinct targets can be indicative of the sample's response to the drug and/or therapy.

A dimension label can be activatable. An activatable dimension label can be activated at a specific time point. The activatable label can be, for example, constitutively activated (e.g., not turned off). The activatable dimension label can be, for example, reversibly activated (e.g., the activatable dimension label can be turned on and turned off). The dimension label can be, for example, reversibly activatable at least 1, 2, 3, 4, 5, 6, 7, 8, 9, 10, or more times. The dimension label can be reversibly activatable, for example, at least 1, 2, 3, 4, 5, 6, 7, 8, 9, 10 or more times. In some embodiments, the dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can, in some embodiments, be identical for all barcodes (e.g., stochastic barcodes) attached to a given solid support (e.g., a bead), but different for different solid supports (e.g., beads). In some embodiments, at least 60%, 70%, 80%, 85%, 90%, 95%, 97%, 99% or 100%, of barcodes on the same solid support can comprise the same dimension label. In some embodiments, at least 60% of barcodes on the same solid support can comprise the same dimension label. In some embodiments, at least 95% of barcodes on the same solid support can comprise the same dimension label.

There can be as many as $10^6$ or more unique dimension label sequences represented in a plurality of solid supports (e.g., beads). A dimension label can be, or be about 1, 2, 3, 4, 5, 10, 15, 20, 25, 30, 35, 40, 45, 50, or a number or a range between any two of these values, nucleotides in length. A dimension label can be at least, or be at most, 1, 2, 3, 4, 5, 10, 15, 20, 25, 30, 35, 40, 45, 50, 100, 200, or 300, nucleotides in length. A dimension label can comprise between about 5 to about 200 nucleotides. A dimension label can comprise between about 10 to about 150 nucleotides. A dimension label can comprise between about 20 to about 125 nucleotides in length.

Spatial Labels

A barcode can comprise one or more spatial labels. In some embodiments, a spatial label can comprise a nucleic acid sequence that provides information about the spatial orientation of a target molecule which is associated with the barcode. A spatial label can be associated with a coordinate in a sample. The coordinate can be a fixed coordinate. For example, a coordinate can be fixed in reference to a substrate. A spatial label can be in reference to a two or three-dimensional grid. A coordinate can be fixed in reference to a landmark. The landmark can be identifiable in space. A landmark can be a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g., A well, a container, or a droplet). In some embodiments, multiple spatial labels are used together to encode one or more positions in space.

The spatial label can be identical for all barcodes attached to a given solid support (e.g., a bead), but different for different solid supports (e.g., beads). In some embodiments, the percentage of barcodes on the same solid support comprising the same spatial label can be, or be about, 60%, 70%, 80%, 85%, 90%, 95%, 97%, 99%, 100%, or a number or a range between any two of these values. In some embodiments, the percentage of barcodes on the same solid support comprising the same spatial label can be at least, or be at most, 60%, 70%, 80%, 85%, 90%, 95%, 97%, 99%, or 100%. In some embodiments, at least 60% of barcodes on the same solid support can comprise the same spatial label. In some embodiments, at least 95% of barcodes on the same solid support can comprise the same spatial label.

There can be as many as $10^6$ or more unique spatial label sequences represented in a plurality of solid supports (e.g., beads). A spatial label can be, or be about, 1, 2, 3, 4, 5, 10, 15, 20, 25, 30, 35, 40, 45, 50, or a number or a range between any two of these values, nucleotides in length. A spatial label can be at least or at most 1, 2, 3, 4, 5, 10, 15, 20, 25, 30, 35, 40, 45, 50, 100, 200, or 300 nucleotides in length. A spatial label can comprise between about 5 to about 200 nucleotides. A spatial label can comprise between about 10 to about 150 nucleotides. A spatial label can comprise between about 20 to about 125 nucleotides in length.

Cell Labels

A barcode (e.g., a stochastic barcode) can comprise one or more cell labels. In some embodiments, a cell label can comprise a nucleic acid sequence that provides information for determining which target nucleic acid originated from which cell. In some embodiments, the cell label is identical for all barcodes attached to a given solid support (e.g., a bead), but different for different solid supports (e.g., beads). In some embodiments, the percentage of barcodes on the same solid support comprising the same cell label can be, or be about 60%, 70%, 80%, 85%, 90%, 95%, 97%, 99%, 100%, or a number or a range between any two of these values. In some embodiments, the percentage of barcodes on the same solid support comprising the same cell label can be, or be about 60%, 70%, 80%, 85%, 90%, 95%, 97%, 99%, or 100%. For example, at least 60% of barcodes on the same solid support can comprise the same cell label. As another example, at least 95% of barcodes on the same solid support can comprise the same cell label. There can be as many as $10^6$ or more unique cell label sequences represented in a plurality of solid supports (e.g., beads). A cell label can be, or be about, 1, 2, 3, 4, 5, 10, 15, 20, 25, 30, 35, 40, 45, 50, or a number or a range between any two of these values, nucleotides in length. A cell label can be at least, or be at most, 1, 2, 3, 4, 5, 10, 15, 20, 25, 30, 35, 40, 45, 50, 100, 200, or 300 nucleotides in length. For example, a cell label can comprise between about 5 to about 200 nucleotides. As another example, a cell label can comprise between about 10 to about 150 nucleotides. As yet another example, a cell label can comprise between about 20 to about 125 nucleotides in length.

Barcode Sequences

A barcode can comprise one or more barcode sequences. In some embodiments, a barcode sequence can comprise a nucleic acid sequence that provides identifying information for the specific type of target nucleic acid species hybridized to the barcode. A barcode sequence can comprise a nucleic acid sequence that provides a counter (e.g., that provides a rough approximation) for the specific occurrence of the target nucleic acid species hybridized to the barcode (e.g., target-binding region).

In some embodiments, a diverse set of barcode sequences are attached to a given solid support (e.g., a bead). In some embodiments, there can be, or be about, $10^2$, $10^3$, $10^4$, $10^5$, $10^6$, $10^7$, $10^8$, $10^9$, or a number or a range between any two of these values, unique molecular label sequences. For example, a plurality of barcodes can comprise about 6561 barcodes sequences with distinct sequences. As another example, a plurality of barcodes can comprise about 65536 barcode sequences with distinct sequences. In some embodiments, there can be at least, or be at most, $10^2$, $10^3$, $10^4$, $10^5$, $10^6$, $10^7$, $10^8$, or $10^9$, unique barcode sequences. The unique molecular label sequences can be attached to a given solid support (e.g., a bead).

The length of a barcode can be different in different implementations. For example, a barcode can be, or be about, 1, 2, 3, 4, 5, 10, 15, 20, 25, 30, 35, 40, 45, 50, or a number or a range between any two of these values, nucleotides in length. As another example, a barcode can be at least, or be at most, 1, 2, 3, 4, 5, 10, 15, 20, 25, 30, 35, 40, 45, 50, 100, 200, or 300 nucleotides in length.

Molecular Labels

A barcode (e.g., a stochastic barcode) can comprise one or more molecular labels. Molecular labels can include barcode sequences. In some embodiments, a molecular label can comprise a nucleic acid sequence that provides identifying information for the specific type of target nucleic acid species hybridized to the barcode. A molecular label can comprise a nucleic acid sequence that provides a counter for the specific occurrence of the target nucleic acid species hybridized to the barcode (e.g., target-binding region).

In some embodiments, a diverse set of molecular labels are attached to a given solid support (e.g., a bead). In some embodiments, there can be, or be about, $10^2$, $10^3$, $10^4$, $10^5$, $10^6$, $10^7$, $10^8$, $10^9$, or a number or a range between any two of these values, of unique molecular label sequences. For example, a plurality of barcodes can comprise about 6561 molecular labels with distinct sequences. As another example, a plurality of barcodes can comprise about 65536 molecular labels with distinct sequences. In some embodiments, there can be at least, or be at most, $10^2$, $10^3$, $10^4$, $10^5$, $10^6$, $10^7$, $10^8$, or $10^9$, unique molecular label sequences. Barcodes with unique molecular label sequences can be attached to a given solid support (e.g., a bead).

For stochastic barcoding using a plurality of stochastic barcodes, the ratio of the number of different molecular label sequences and the number of occurrence of any of the targets can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. In some embodiments, the ratio of the number of different molecular label sequences and the number of occurrence of any of the targets is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1.

A molecular label can be, or be about, 1, 2, 3, 4, 5, 10, 15, 20, 25, 30, 35, 40, 45, 50, or a number or a range between any two of these values, nucleotides in length. A molecular label can be at least, or be at most, 1, 2, 3, 4, 5, 10, 15, 20, 25, 30, 35, 40, 45, 50, 100, 200, or 300 nucleotides in length.

Target-Binding Region

A barcode can comprise one or more target binding regions, such as capture probes. In some embodiments, a target-binding region can hybridize with a target of interest. In some embodiments, the target binding regions can comprise a nucleic acid sequence that hybridizes specifically to a target (e.g., a target nucleic acid, a target molecule, a cellular nucleic acid to be analyzed), for example to a specific gene sequence. In some embodiments, a target binding region can comprise a nucleic acid sequence that can attach (e.g., hybridize) to a specific location of a specific target nucleic acid. In some embodiments, the target binding region can comprise a nucleic acid sequence that is capable of specific hybridization to a restriction enzyme site overhang (e.g., an EcoRI sticky-end overhang). The barcode can then ligate to any nucleic acid molecule comprising a sequence complementary to the restriction site overhang.

In some embodiments, a target binding region can comprise a non-specific target nucleic acid sequence. A non-specific target nucleic acid sequence can refer to a sequence that can bind to multiple target nucleic acids, independent of the specific sequence of the target nucleic acid. For example, target binding region can comprise a random multimer sequence, a poly(dA) sequence, a poly(dT) sequence, a poly(dG) sequence, a poly(dC) sequence, or a combination thereof. For example, the target binding region can be an oligo(dT) sequence that hybridizes to the poly(A) tail on mRNA molecules. For example, an mRNA molecule can be reverse transcribed using a reverse transcriptase, such as Moloney murine leukemia virus (MMLV) reverse transcriptase, to generate a cDNA molecule with a poly(dC) tail. A barcode can include a target binding region with a poly(dG) tail. Upon base pairing between the poly(dG) tail of the barcode and the poly(dC) tail of the cDNA molecule, the reverse transcriptase switches template strands, from cellular RNA molecule to the barcode, and continues replication to the 5' end of the barcode. By doing so, the resulting cDNA molecule contains the sequence of the barcode (such as the molecular label) on the 3' end of the cDNA molecule.

A random multimer sequence can be, for example, a random dimer, trimer, quatramer, pentamer, hexamer, septamer, octamer, nonamer, decamer, or higher multimer sequence of any length. In some embodiments, the target binding region is the same for all barcodes attached to a given bead. In some embodiments, the target binding regions for the plurality of barcodes attached to a given bead can comprise two or more different target binding sequences. A target binding region can be, or be about, 1, 2, 3, 4, 5, 10, 15, 20, 25, 30, 35, 40, 45, 50, or a number or a range between any two of these values, nucleotides in length. A target binding region can be at most about 1, 2, 3, 4, 5, 10, 15, 20, 25, 30, 35, 40, 45, 50 or more nucleotides in length.

In some embodiments, a target-binding region can comprise an oligo(dT) which can hybridize with mRNAs comprising polyadenylated ends. A target-binding region can be gene-specific. For example, a target-binding region can be configured to hybridize to a specific region of a target. A target-binding region can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these values, nucleotides in length. A target-binding region can be at least, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30, nucleotides in length. A target-binding region can be about 5-30 nucleotides in length. When a barcode comprises a gene-specific target-binding region, the barcode can be referred to herein as a gene-specific barcode.

The target-binding region can interact with a target in a sample. The target can be, or comprise, ribonucleic acids (RNAs), messenger RNAs (mRNAs), microRNAs, small interfering RNAs (siRNAs), RNA degradation products, RNAs each comprising a poly(A) tail, or any combination thereof. In some embodiments, the plurality of targets can include deoxyribonucleic acids (DNAs).

In some embodiments, a target-binding region can comprise an oligo(dT) sequence which can interact with poly(A) tails of mRNAs. One or more of the labels of the barcode (e.g., the universal label, the dimension label, the spatial label, the cell label, and the barcode sequences (e.g., molecular label)) can be separated by a spacer from another one or two of the remaining labels of the barcode. The spacer can be, for example, 1, 2, 3, 4, 5, 6, 7, 8, 9, 10, 11, 12, 13, 14, 15, 16, 17, 18, 19, or 20, or more nucleotides. In some embodiments, none of the labels of the barcode is separated by spacer.

Orientation Property

A stochastic barcode (e.g., a stochastic barcode) can comprise one or more orientation properties which can be used to orient (e.g., align) the barcodes. A barcode can comprise a moiety for isoelectric focusing. Different barcodes can comprise different isoelectric focusing points. When these barcodes are introduced to a sample, the sample can undergo isoelectric focusing in order to orient the barcodes into a known way. In this way, the orientation property can be used to develop a known map of barcodes in a sample. Exemplary orientation properties can include, electrophoretic mobility (e.g., based on size of the barcode), isoelectric point, spin, conductivity, and/or self-assembly. For example, barcodes with an orientation property of self-assembly, can self-assemble into a specific orientation (e.g., nucleic acid nanostructure) upon activation.

Affinity Property

A barcode (e.g., a stochastic barcode) can comprise one or more affinity properties. For example, a spatial label can comprise an affinity property. An affinity property can include a chemical and/or biological moiety that can facilitate binding of the barcode to another entity (e.g., cell receptor). For example, an affinity property can comprise an antibody, for example, an antibody specific for a specific moiety (e.g., receptor) on a sample. In some embodiments, the antibody can guide the barcode to a specific cell type or molecule. Targets at and/or near the specific cell type or molecule can be labeled (e.g., stochastically labeled). The affinity property can, in some embodiments, provide spatial information in addition to the nucleotide sequence of the spatial label because the antibody can guide the barcode to a specific location. The antibody can be a therapeutic antibody, for example a monoclonal antibody or a polyclonal antibody. The antibody can be humanized or chimeric. The antibody can be a naked antibody or a fusion antibody.

The antibody can be a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

The antibody fragment can be, for example, a portion of an antibody such as F(ab')2, Fab', Fab, Fv, sFv and the like.

In some embodiments, the antibody fragment can bind with the same antigen that is recognized by the full-length antibody. The antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (CD8, CD34, CD45), and therapeutic antibodies.

Universal Adaptor Primer

A barcode can comprise one or more universal adaptor primers. For example, a gene-specific barcode, such as a gene-specific stochastic barcode, can comprise a universal adaptor primer. A universal adaptor primer can refer to a nucleotide sequence that is universal across all barcodes. A universal adaptor primer can be used for building gene-specific barcodes. A universal adaptor primer can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these nucleotides in length. A universal adaptor primer can be at least, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 nucleotides in length. A universal adaptor primer can be from 5-30 nucleotides in length.

Linker

When a barcode comprises more than one of a type of label (e.g., more than one cell label or more than one barcode sequence, such as one molecular label), the labels may be interspersed with a linker label sequence. A linker label sequence can be at least about 5, 10, 15, 20, 25, 30, 35, 40, 45, 50 or more nucleotides in length. A linker label sequence can be at most about 5, 10, 15, 20, 25, 30, 35, 40, 45, 50 or more nucleotides in length. In some instances, a linker label sequence is 12 nucleotides in length. A linker label sequence can be used to facilitate the synthesis of the barcode. The linker label can comprise an error-correcting (e.g., Hamming) code.

Solid Supports

Barcodes, such as stochastic barcodes, disclosed herein can, in some embodiments, be associated with a solid support. The solid support can be, for example, a synthetic particle. In some embodiments, some or all of the barcode sequences, such as molecular labels for stochastic barcodes (e.g., the first barcode sequences) of a plurality of barcodes (e.g., the first plurality of barcodes) on a solid support differ by at least one nucleotide. The cell labels of the barcodes on the same solid support can be the same. The cell labels of the barcodes on different solid supports can differ by at least one nucleotide. For example, first cell labels of a first plurality of barcodes on a first solid support can have the same sequence, and second cell labels of a second plurality of barcodes on a second solid support can have the same sequence. The first cell labels of the first plurality of barcodes on the first solid support and the second cell labels of the second plurality of barcodes on the second solid support can differ by at least one nucleotide. A cell label can be, for example, about 5-20 nucleotides long. A barcode sequence can be, for example, about 5-20 nucleotides long. The synthetic particle can be, for example, a bead.

The bead can be, for example, a silica gel bead, a controlled pore glass bead, a magnetic bead, a Dynabead, a Sephadex/Sepharose bead, a cellulose bead, a polystyrene bead, or any combination thereof. The bead can comprise a material such as polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof.

In some embodiments, the bead can be a polymeric bead, for example a deformable bead or a gel bead, functionalized with barcodes or stochastic barcodes (such as gel beads from 10× Genomics (San Francisco, CA). In some implementation, a gel bead can comprise a polymer-based gels. Gel beads can be generated, for example, by encapsulating one or more polymeric precursors into droplets. Upon exposure of the polymeric precursors to an accelerator (e.g., tetramethylethylenediamine (TEMED)), a gel bead may be generated.

In some embodiments, the particle can be degradable. For example, the polymeric bead can dissolve, melt, or degrade, for example, under a desired condition. The desired condition can include an environmental condition. The desired condition may result in the polymeric bead dissolving, melting, or degrading in a controlled manner. A gel bead may dissolve, melt, or degrade due to a chemical stimulus, a physical stimulus, a biological stimulus, a thermal stimulus, a magnetic stimulus, an electric stimulus, a light stimulus, or any combination thereof.

Analytes and/or reagents, such as oligonucleotide barcodes, for example, may be coupled/immobilized to the interior surface of a gel bead (e.g., the interior accessible via diffusion of an oligonucleotide barcode and/or materials used to generate an oligonucleotide barcode) and/or the outer surface of a gel bead or any other microcapsule described herein. Coupling/immobilization may be via any form of chemical bonding (e.g., covalent bond, ionic bond) or physical phenomena (e.g., Van der Waals forces, dipole-dipole interactions, etc.). In some embodiments, coupling/immobilization of a reagent to a gel bead or any other microcapsule described herein may be reversible, such as, for example, via a labile moiety (e.g., via a chemical cross-linker, including chemical cross-linkers described herein). Upon application of a stimulus, the labile moiety may be cleaved and the immobilized reagent set free. In some embodiments, the labile moiety is a disulfide bond. For example, in the case where an oligonucleotide barcode is immobilized to a gel bead via a disulfide bond, exposure of the disulfide bond to a reducing agent can cleave the disulfide bond and free the oligonucleotide barcode from the bead. The labile moiety may be included as part of a gel bead or microcapsule, as part of a chemical linker that links a reagent or analyte to a gel bead or microcapsule, and/or as part of a reagent or analyte. In some embodiments, at least one barcode of the plurality of barcodes can be immobilized on the particle, partially immobilized on the particle, enclosed in the particle, partially enclosed in the particle, or any combination thereof.

In some embodiments, a gel bead can comprise a wide range of different polymers including but not limited to: polymers, heat sensitive polymers, photosensitive polymers, magnetic polymers, pH sensitive polymers, salt-sensitive polymers, chemically sensitive polymers, polyelectrolytes, polysaccharides, peptides, proteins, and/or plastics. Polymers may include but are not limited to materials such as poly(N-isopropylacrylamide) (PNIPAAm), poly(styrene sulfonate) (PSS), poly(allyl amine) (PAAm), poly(acrylic acid) (PAA), poly(ethylene imine) (PEI), poly(diallyldimethyl-ammonium chloride) (PDADMAC), poly(pyrolle) (PPy), poly(vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthaladehyde) (PTHF), poly(hexyl viologen) (PHV), poly(L-lysine) (PLL), poly(L-arginine) (PARG), poly(lactic-co-glycolic acid) (PLGA).

Numerous chemical stimuli can be used to trigger the disruption, dissolution, or degradation of the beads. Examples of these chemical changes may include, but are not limited to pH-mediated changes to the bead wall, disintegration of the bead wall via chemical cleavage of cross-link bonds, triggered depolymerization of the bead wall, and bead wall switching reactions. Bulk changes may also be used to trigger disruption of the beads.

Bulk or physical changes to the microcapsule through various stimuli also offer many advantages in designing capsules to release reagents. Bulk or physical changes occur on a macroscopic scale, in which bead rupture is the result of mechano-physical forces induced by a stimulus. These processes may include, but are not limited to pressure induced rupture, bead wall melting, or changes in the porosity of the bead wall.

Biological stimuli may also be used to trigger disruption, dissolution, or degradation of beads. Generally, biological triggers resemble chemical triggers, but many examples use biomolecules, or molecules commonly found in living systems such as enzymes, peptides, saccharides, fatty acids, nucleic acids and the like. For example, beads may comprise polymers with peptide cross-links that are sensitive to cleavage by specific proteases. More specifically, one example may comprise a microcapsule comprising GFLGK peptide cross links. Upon addition of a biological trigger such as the protease Cathepsin B, the peptide cross links of the shell well are cleaved and the contents of the beads are released. In other cases, the proteases may be heat-activated. In another example, beads comprise a shell wall comprising cellulose. Addition of the hydrolytic enzyme chitosan serves as biologic trigger for cleavage of cellulosic bonds, depolymerization of the shell wall, and release of its inner contents.

The beads may also be induced to release their contents upon the application of a thermal stimulus. A change in temperature can cause a variety changes to the beads. A change in heat may cause melting of a bead such that the bead wall disintegrates. In other cases, the heat may increase the internal pressure of the inner components of the bead such that the bead ruptures or explodes. In still other cases, the heat may transform the bead into a shrunken dehydrated state. The heat may also act upon heat-sensitive polymers within the wall of a bead to cause disruption of the bead.

Inclusion of magnetic nanoparticles to the bead wall of microcapsules may allow triggered rupture of the beads as well as guide the beads in an array. A device of this disclosure may comprise magnetic beads for either purpose. In one example, incorporation of $Fe_3O_4$ nanoparticles into polyelectrolyte containing beads triggers rupture in the presence of an oscillating magnetic field stimulus.

A bead may also be disrupted, dissolved, or degraded as the result of electrical stimulation. Similar to magnetic particles described in the previous section, electrically sensitive beads can allow for both triggered rupture of the beads as well as other functions such as alignment in an electric field, electrical conductivity or redox reactions. In one example, beads containing electrically sensitive material are aligned in an electric field such that release of inner reagents can be controlled. In other examples, electrical fields may induce redox reactions within the bead wall itself that may increase porosity.

A light stimulus may also be used to disrupt the beads. Numerous light triggers are possible and may include systems that use various molecules such as nanoparticles and chromophores capable of absorbing photons of specific ranges of wavelengths. For example, metal oxide coatings can be used as capsule triggers. UV irradiation of polyelectrolyte capsules coated with $SiO_2$ may result in disintegration of the bead wall. In yet another example, photo switchable materials such as azobenzene groups may be incorporated in the bead wall. Upon the application of UV or visible light, chemicals such as these undergo a reversible cis-to-trans isomerization upon absorption of photons. In this aspect, incorporation of photon switches result in a bead wall that may disintegrate or become more porous upon the application of a light trigger.

Figure 2:
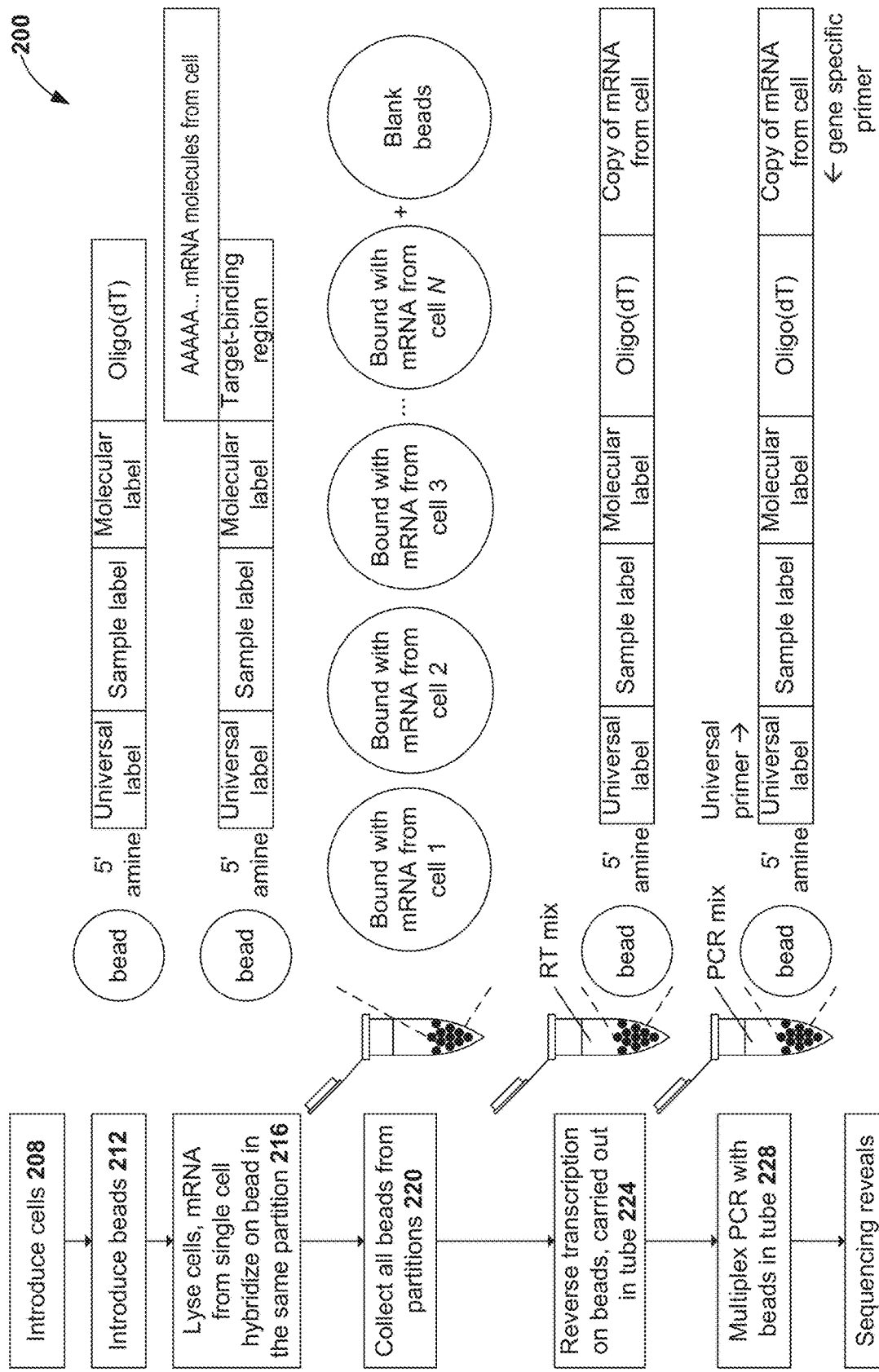
FIG. 2 shows a non-limiting exemplary workflow of stochastic barcoding and digital counting.

For example, in a non-limiting example of barcoding (e.g., stochastic barcoding) illustrated in FIG. 2, after introducing cells such as single cells onto a plurality of microwells of a microwell array at block 208, beads can be introduced onto the plurality of microwells of the microwell array at block 212. Each microwell can comprise one bead. The beads can comprise a plurality of barcodes. A barcode can comprise a 5' amine region attached to a bead. The barcode can comprise a universal label, a barcode sequence (e.g., a molecular label), a target-binding region, or any combination thereof.

The barcodes disclosed herein can be associated with (e.g., attached to) a solid support (e.g., a bead). The barcodes associated with a solid support can each comprise a barcode sequence selected from a group comprising at least 100 or 1000 barcode sequences with unique sequences. In some embodiments, different barcodes associated with a solid support can comprise barcode with different sequences. In some embodiments, a percentage of barcodes associated with a solid support comprises the same cell label. For example, the percentage can be, or be about 60%, 70%, 80%, 85%, 90%, 95%, 97%, 99%, 100%, or a number or a range between any two of these values. As another example, the percentage can be at least, or be at most 60%, 70%, 80%, 85%, 90%, 95%, 97%, 99%, or 100%. In some embodiments, barcodes associated with a solid support can have the same cell label. The barcodes associated with different solid supports can have different cell labels selected from a group comprising at least 100 or 1000 cell labels with unique sequences.

The barcodes disclosed herein can be associated to (e.g., attached to) a solid support (e.g., a bead). In some embodiments, barcoding the plurality of targets in the sample can be performed with a solid support including a plurality of synthetic particles associated with the plurality of barcodes. In some embodiments, the solid support can include a plurality of synthetic particles associated with the plurality of barcodes. The spatial labels of the plurality of barcodes on different solid supports can differ by at least one nucleotide. The solid support can, for example, include the plurality of barcodes in two dimensions or three dimensions. The synthetic particles can be beads. The beads can be silica gel beads, controlled pore glass beads, magnetic beads, Dynabeads, Sephadex/Sepharose beads, cellulose beads, polystyrene beads, or any combination thereof. The solid support can include a polymer, a matrix, a hydrogel, a needle array device, an antibody, or any combination thereof. In some embodiments, the solid supports can be free floating. In some embodiments, the solid supports can be embedded in a semi-solid or solid array. The barcodes may not be associated with solid supports. The barcodes can be individual nucleotides. The barcodes can be associated with a substrate.

As used herein, the terms "tethered," "attached," and "immobilized," are used interchangeably, and can refer to covalent or non-covalent means for attaching barcodes to a solid support. Any of a variety of different solid supports can be used as solid supports for attaching pre-synthesized barcodes or for in situ solid-phase synthesis of barcode.

In some embodiments, the solid support is a bead. The bead can comprise one or more types of solid, porous, or hollow sphere, ball, bearing, cylinder, or other similar configuration which a nucleic acid can be immobilized (e.g., covalently or non-covalently). The bead can be, for example, composed of plastic, ceramic, metal, polymeric material, or any combination thereof. A bead can be, or comprise, a discrete particle that is spherical (e.g., microspheres) or have a non-spherical or irregular shape, such as cubic, cuboid, pyramidal, cylindrical, conical, oblong, or disc-shaped, and the like. In some embodiments, a bead can be non-spherical in shape.

Beads can comprise a variety of materials including, but not limited to, paramagnetic materials (e.g., magnesium, molybdenum, lithium, and tantalum), superparamagnetic materials (e.g., ferrite ($Fe_3O_4$; magnetite) nanoparticles), ferromagnetic materials (e.g., iron, nickel, cobalt, some alloys thereof, and some rare earth metal compounds), ceramic, plastic, glass, polystyrene, silica, methylstyrene, acrylic polymers, titanium, latex, Sepharose, agarose, hydrogel, polymer, cellulose, nylon, or any combination thereof.

In some embodiments, the bead (e.g., the bead to which the labels are attached) is a hydrogel bead. In some embodiments, the bead comprises hydrogel.

Some embodiments disclosed herein include one or more particles (for example, beads). Each of the particles can comprise a plurality of oligonucleotides (e.g., barcodes). Each of the plurality of oligonucleotides can comprise a barcode sequence (e.g., a molecular label sequence), a cell label, and a target-binding region (e.g., an oligo(dT) sequence, a gene-specific sequence, a random multimer, or a combination thereof). The cell label sequence of each of the plurality of oligonucleotides can be the same. The cell label sequences of oligonucleotides on different particles can be different such that the oligonucleotides on different particles can be identified. The number of different cell label sequences can be different in different implementations. In some embodiments, the number of cell label sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of cell label sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. In some embodiments, no more than 1, 2, 3, 4, 5, 6, 7, 8, 9, 10, 20, 30, 40, 50, 60, 70, 80, 90, 100, 200, 300, 400, 500, 600, 700, 800, 900, 1000, or more of the plurality of the particles include oligonucleotides with the same cell sequence. In some embodiment, the plurality of particles that include oligonucleotides with the same cell sequence can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or more. In some embodiments, none of the plurality of the particles has the same cell label sequence.

The plurality of oligonucleotides on each particle can comprise different barcode sequences (e.g., molecular labels). In some embodiments, the number of barcode sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. In some embodiments, the number of barcode sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. For example, at least 100 of the plurality of oligonucleotides comprise different barcode sequences. As another example, in a single particle, at least 100, 500, 1000, 5000, 10000, 15000, 20000, 50000, a number or a range between any two of these values, or more of the plurality of oligonucleotides comprise different barcode sequences. Some embodiments provide a plurality of the particles comprising barcodes. In some embodiments, the ratio of an occurrence (or a copy or a number) of a target to be labeled and the different barcode sequences can be at least 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, or more. In some embodiments, each of the plurality of oligonucleotides further comprises a sample label, a universal label, or both. The particle can be, for example, a nanoparticle or microparticle.

The size of the beads can vary. For example, the diameter of the bead can range from 0.1 micrometer to 50 micrometers. In some embodiments, the diameter of the bead can be, or be about, 0.1, 0.5, 1, 2, 3, 4, 5, 6, 7, 8, 9, 10, 20, 30, 40, 50 micrometers, or a number or a range between any two of these values.

The diameter of the bead can be related to the diameter of the wells of the substrate. In some embodiments, the diameter of the bead can be, or be about, 10%, 20%, 30%, 40%, 50%, 60%, 70%, 80%, 90%, 100%, or a number or a range between any two of these values, longer or shorter than the diameter of the well. The diameter of the beads can be related to the diameter of a cell (e.g., a single cell entrapped by a well of the substrate). In some embodiments, the diameter of the bead can be at least, or be at most, 10%, 20%, 30%, 40%, 50%, 60%, 70%, 80%, 90%, or 100% longer or shorter than the diameter of the well. The diameter of the beads can be related to the diameter of a cell (e.g., a single cell entrapped by a well of the substrate). In some embodiments, the diameter of the bead can be, or be about, 10%, 20%, 30%, 40%, 50%, 60%, 70%, 80%, 90%, 100%, 150%, 200%, 250%, 300%, or a number or a range between any two of these values, longer or shorter than the diameter of the cell. In some embodiments, the diameter of the beads can be at least, or be at most, 10%, 20%, 30%, 40%, 50%, 60%, 70%, 80%, 90%, 100%, 150%, 200%, 250%, or 300% longer or shorter than the diameter of the cell.

A bead can be attached to and/or embedded in a substrate. A bead can be attached to and/or embedded in a gel, hydrogel, polymer and/or matrix. The spatial position of a bead within a substrate (e.g., gel, matrix, scaffold, or polymer) can be identified using the spatial label present on the barcode on the bead which can serve as a location address.

Examples of beads can include, but are not limited to, streptavidin beads, agarose beads, magnetic beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, silica beads, silica-like beads, anti-biotin microbeads, anti-fluorochrome microbeads, and BcMag™ Carboxyl-Terminated Magnetic Beads.

A bead can be associated with (e.g., impregnated with) quantum dots or fluorescent dyes to make it fluorescent in one fluorescence optical channel or multiple optical channels. A bead can be associated with iron oxide or chromium oxide to make it paramagnetic or ferromagnetic. Beads can be identifiable. For example, a bead can be imaged using a camera. A bead can have a detectable code associated with the bead. For example, a bead can comprise a barcode. A bead can change size, for example, due to swelling in an organic or inorganic solution. A bead can be hydrophobic. A bead can be hydrophilic. A bead can be biocompatible.

A solid support (e.g., a bead) can be visualized. The solid support can comprise a visualizing tag (e.g., fluorescent dye). A solid support (e.g., a bead) can be etched with an identifier (e.g., a number). The identifier can be visualized through imaging the beads.

A solid support can comprise an insoluble, semi-soluble, or insoluble material. A solid support can be referred to as "functionalized" when it includes a linker, a scaffold, a building block, or other reactive moiety attached thereto, whereas a solid support may be "nonfunctionalized" when it lack such a reactive moiety attached thereto. The solid support can be employed free in solution, such as in a microtiter well format; in a flow-through format, such as in a column; or in a dipstick.

The solid support can comprise a membrane, paper, plastic, coated surface, flat surface, glass, slide, chip, or any combination thereof. A solid support can take the form of resins, gels, microspheres, or other geometric configurations. A solid support can comprise silica chips, microparticles, nanoparticles, plates, arrays, capillaries, flat supports such as glass fiber filters, glass surfaces, metal surfaces (steel, gold silver, aluminum, silicon and copper), glass supports, plastic supports, silicon supports, chips, filters, membranes, microwell plates, slides, plastic materials including multiwell plates or membranes (e.g., formed of polyethylene, polypropylene, polyamide, polyvinylidenedifluoride), and/or wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

The solid support can comprise a polymer matrix (e.g., gel, hydrogel). The polymer matrix may be able to permeate intracellular space (e.g., around organelles). The polymer matrix may able to be pumped throughout the circulatory system.

Substrates and Microwell Array

As used herein, a substrate can refer to a type of solid support. A substrate can refer to a solid support that can comprise barcodes or stochastic barcodes of the disclosure. A substrate can, for example, comprise a plurality of microwells. For example, a substrate can be a well array comprising two or more microwells. In some embodiments, a microwell can comprise a small reaction chamber of defined volume. In some embodiments, a microwell can entrap one or more cells. In some embodiments, a microwell can entrap only one cell. In some embodiments, a microwell can entrap one or more solid supports. In some embodiments, a microwell can entrap only one solid support. In some embodiments, a microwell entraps a single cell and a single solid support (e.g., a bead). A microwell can comprise barcode reagents of the disclosure.

Methods of Barcoding

The disclosure provides for methods for estimating the number of distinct targets at distinct locations in a physical sample (e.g., tissue, organ, tumor, cell). The methods can comprise placing barcodes (e.g., stochastic barcodes) in close proximity with the sample, lysing the sample, associating distinct targets with the barcodes, amplifying the targets and/or digitally counting the targets. The method can further comprise analyzing and/or visualizing the information obtained from the spatial labels on the barcodes. In some embodiments, a method comprises visualizing the plurality of targets in the sample. Mapping the plurality of targets onto the map of the sample can include generating a two-dimensional map or a three-dimensional map of the sample. The two-dimensional map and the three-dimensional map can be generated prior to or after barcoding (e.g., stochastically barcoding) the plurality of targets in the sample. Visualizing the plurality of targets in the sample can include mapping the plurality of targets onto a map of the sample. Mapping the plurality of targets onto the map of the sample can include generating a two-dimensional map or a three-dimensional map of the sample. The two-dimensional map and the three-dimensional map can be generated prior to or after barcoding the plurality of targets in the sample. in some embodiments, the two-dimensional map and the three-dimensional map can be generated before or after lysing the sample. Lysing the sample before or after generating the two-dimensional map or the three-dimensional map can include heating the sample, contacting the sample with a detergent, changing the pH of the sample, or any combination thereof.

In some embodiments, barcoding the plurality of targets comprises hybridizing a plurality of barcodes with a plurality of targets to create barcoded targets (e.g., stochastically barcoded targets). Barcoding the plurality of targets can comprise generating an indexed library of the barcoded targets. Generating an indexed library of the barcoded targets can be performed with a solid support comprising the plurality of barcodes (e.g., stochastic barcodes).

Contacting a Sample and a Barcode

The disclosure provides for methods for contacting a sample (e.g., cells) to a substrate of the disclosure. A sample comprising, for example, a cell, organ, or tissue thin section, can be contacted to barcodes (e.g., stochastic barcodes). The cells can be contacted, for example, by gravity flow wherein the cells can settle and create a monolayer. The sample can be a tissue thin section. The thin section can be placed on the substrate. The sample can be one-dimensional (e.g., forms a planar surface). The sample (e.g., cells) can be spread across the substrate, for example, by growing/culturing the cells on the substrate.

When barcodes are in close proximity to targets, the targets can hybridize to the barcode. The barcodes can be contacted at a non-depletable ratio such that each distinct target can associate with a distinct barcode of the disclosure. To ensure efficient association between the target and the barcode, the targets can be cross-linked to barcode.

Cell Lysis

Following the distribution of cells and barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g., SDS, Li dodecyl sulfate, Triton X-100, Tween-20, or NP-40), an organic solvent (e.g., methanol or acetone), or digestive enzymes (e.g., proteinase K, pepsin, or trypsin), or any combination thereof. To increase the association of a target and a barcode, the rate of the diffusion of the target molecules can be altered by for example, reducing the temperature and/or increasing the viscosity of the lysate.

In some embodiments, the sample can be lysed using a filter paper. The filter paper can be soaked with a lysis buffer on top of the filter paper. The filter paper can be applied to the sample with pressure which can facilitate lysis of the sample and hybridization of the targets of the sample to the substrate.

In some embodiments, lysis can be performed by mechanical lysis, heat lysis, optical lysis, and/or chemical lysis. Chemical lysis can include the use of digestive enzymes such as proteinase K, pepsin, and trypsin. Lysis can be performed by the addition of a lysis buffer to the substrate. A lysis buffer can comprise Tris HCl. A lysis buffer can comprise at least about 0.01, 0.05, 0.1, 0.5, or 1 M or more Tris HCl. A lysis buffer can comprise at most about 0.01, 0.05, 0.1, 0.5, or 1 M or more Tris HCL. A lysis buffer can comprise about 0.1 M Tris HCl. The pH of the lysis buffer can be at least about 1, 2, 3, 4, 5, 6, 7, 8, 9, 10, or more. The pH of the lysis buffer can be at most about 1, 2, 3, 4, 5, 6, 7, 8, 9, 10, or more. In some embodiments, the pH of the lysis buffer is about 7.5. The lysis buffer can comprise a salt (e.g., LiCl). The concentration of salt in the lysis buffer can be at least about 0.1, 0.5, or 1 M or more. The concentration of salt in the lysis buffer can be at most about 0.1, 0.5, or 1 M or more. In some embodiments, the concentration of salt in the lysis buffer is about 0.5M. The lysis buffer can comprise a detergent (e.g., SDS, Li dodecyl sulfate, triton X, tween, NP-40). The concentration of the detergent in the lysis buffer can be at least about 0.0001%, 0.0005%, 0.001%, 0.005%, 0.01%, 0.05%, 0.1%, 0.5%, 1%, 2%, 3%, 4%, 5%, 6%, or 7%, or more. The concentration of the detergent in the lysis buffer can be at most about 0.0001%, 0.0005%, 0.001%, 0.005%, 0.01%, 0.05%, 0.1%, 0.5%, 1%, 2%, 3%, 4%, 5%, 6%, or 7%, or more. In some embodiments, the concentration of the detergent in the lysis buffer is about 1% Li dodecyl sulfate. The time used in the method for lysis can be dependent on the amount of detergent used. In some embodiments, the more detergent used, the less time needed for lysis. The lysis buffer can comprise a chelating agent (e.g., EDTA, EGTA). The concentration of a chelating agent in the lysis buffer can be at least about 1, 5, 10, 15, 20, 25, or 30 mM or more. The concentration of a chelating agent in the lysis buffer can be at most about 1, 5, 10, 15, 20, 25, or 30 mM or more. In some embodiments, the concentration of chelating agent in the lysis buffer is about 10 mM. The lysis buffer can comprise a reducing reagent (e.g., beta-mercaptoethanol, DTT). The concentration of the reducing reagent in the lysis buffer can be at least about 1, 5, 10, 15, or 20 mM or more. The concentration of the reducing reagent in the lysis buffer can be at most about 1, 5, 10, 15, or 20 mM or more. In some embodiments, the concentration of reducing reagent in the lysis buffer is about 5 mM. In some embodiments, a lysis buffer can comprise about 0.1M TrisHCl, about pH 7.5, about 0.5M LiCl, about 1% lithium dodecyl sulfate, about 10 mM EDTA, and about 5 mM DTT.

Lysis can be performed at a temperature of about 4, 10, 15, 20, 25, or 30° C. Lysis can be performed for about 1, 5, 10, 15, or 20 or more minutes. A lysed cell can comprise at least about 100000, 200000, 300000, 400000, 500000, 600000, or 700000 or more target nucleic acid molecules. A lysed cell can comprise at most about 100000, 200000, 300000, 400000, 500000, 600000, or 700000 or more target nucleic acid molecules.

Attachment of Barcodes to Target Nucleic Acid Molecules

Following lysis of the cells and release of nucleic acid molecules therefrom, the nucleic acid molecules can randomly associate with the barcodes of the co-localized solid support. Association can comprise hybridization of a barcode's target recognition region to a complementary portion of the target nucleic acid molecule (e.g., oligo(dT) of the barcode can interact with a poly(A) tail of a target). The assay conditions used for hybridization (e.g., buffer pH, ionic strength, temperature, etc.) can be chosen to promote formation of specific, stable hybrids. In some embodiments, the nucleic acid molecules released from the lysed cells can associate with the plurality of probes on the substrate (e.g., hybridize with the probes on the substrate). When the probes comprise oligo(dT), mRNA molecules can hybridize to the probes and be reverse transcribed. The oligo(dT) portion of the oligonucleotide can act as a primer for first strand synthesis of the cDNA molecule. For example, in a non-limiting example of barcoding illustrated in FIG. 2, at block 216, mRNA molecules can hybridize to barcodes on beads. For example, single-stranded nucleotide fragments can hybridize to the target-binding regions of barcodes.

Attachment can further comprise ligation of a barcode's target recognition region and a portion of the target nucleic acid molecule. For example, the target binding region can comprise a nucleic acid sequence that can be capable of specific hybridization to a restriction site overhang (e.g., an EcoRI sticky-end overhang). The assay procedure can further comprise treating the target nucleic acids with a restriction enzyme (e.g., EcoRI) to create a restriction site overhang. The barcode can then be ligated to any nucleic acid molecule comprising a sequence complementary to the restriction site overhang. A ligase (e.g., T4 DNA ligase) can be used to join the two fragments.

For example, in a non-limiting example of barcoding illustrated in FIG. 2, at block 220, the labeled targets from a plurality of cells (or a plurality of samples) (e.g., target-barcode molecules) can be subsequently pooled, for example, into a tube. The labeled targets can be pooled by, for example, retrieving the barcodes and/or the beads to which the target-barcode molecules are attached.

The retrieval of solid support-based collections of attached target-barcode molecules can be implemented by use of magnetic beads and an externally-applied magnetic field. Once the target-barcode molecules have been pooled, all further processing can proceed in a single reaction vessel. Further processing can include, for example, reverse transcription reactions, amplification reactions, cleavage reactions, dissociation reactions, and/or nucleic acid extension reactions. Further processing reactions can be performed within the microwells, that is, without first pooling the labeled target nucleic acid molecules from a plurality of cells.

Reverse Transcription or Nucleotide Extension

The disclosure provides for a method to create a target-barcode conjugate using reverse transcription (e.g., at block 224 of FIG. 2) or nucleotide extension (e.g., of a sample indexing oligonucleotide or a cellular component=binding reagent specific oligonucleotide). The target-barcode conjugate can comprise the barcode and a complementary sequence of all or a portion of the target nucleic acid (i.e., a barcoded cDNA molecule, such as a stochastically barcoded cDNA molecule). Reverse transcription of the associated RNA molecule can occur by the addition of a reverse transcription primer along with the reverse transcriptase. The reverse transcription primer can be an oligo(dT) primer, a random hexanucleotide primer, or a target-specific oligonucleotide primer. Oligo(dT) primers can be, or can be about, 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, reverse transcription of an mRNA molecule to generate to a labeled-RNA molecule can occur by the addition of a reverse transcription primer. In some embodiments, the reverse transcription primer is an oligo (dT) primer, random hexanucleotide primer, or a target-specific oligonucleotide primer. Generally, oligo(dT) primers are 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, a target is a cDNA molecule. For example, an mRNA molecule can be reverse transcribed using a reverse transcriptase, such as Moloney murine leukemia virus (MMLV) reverse transcriptase, to generate a cDNA molecule with a poly(dC) tail. A barcode can include a target binding region with a poly(dG) tail. Upon base pairing between the poly(dG) tail of the barcode and the poly(dC) tail of the cDNA molecule, the reverse transcriptase switches template strands, from cellular RNA molecule to the barcode, and continues replication to the 5' end of the barcode. By doing so, the resulting cDNA molecule contains the sequence of the barcode (such as the molecular label) on the 3' end of the cDNA molecule.

Reverse transcription can occur repeatedly to produce multiple labeled-cDNA molecules. The methods disclosed herein can comprise conducting at least about 1, 2, 3, 4, 5, 6, 7, 8, 9, 10, 11, 12, 13, 14, 15, 16, 17, 18, 19, or 20 reverse transcription reactions. The method can comprise conducting at least about 25, 30, 35, 40, 45, 50, 55, 60, 65, 70, 75, 80, 85, 90, 95, or 100 reverse transcription reactions.

Amplification

One or more nucleic acid amplification reactions (e.g., at block 228 of FIG. 2) can be performed to create multiple copies of the labeled target nucleic acid molecules. Amplification can be performed in a multiplexed manner, wherein multiple target nucleic acid sequences are amplified simultaneously. The amplification reaction can be used to add sequencing adaptors to the nucleic acid molecules. The amplification reactions can comprise amplifying at least a portion of a sample label, if present. The amplification reactions can comprise amplifying at least a portion of the cellular label and/or barcode sequence (e.g., a molecular label). The amplification reactions can comprise amplifying at least a portion of a sample tag, a cell label, a spatial label, a barcode sequence (e.g., a molecular label), a target nucleic acid, or a combination thereof. The amplification reactions can comprise amplifying 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range or a number between any two of these values, of the plurality of nucleic acids. The method can further comprise conducting one or more cDNA synthesis reactions to produce one or more cDNA copies of target-barcode molecules comprising a sample label, a cell label, a spatial label, and/or a barcode sequence (e.g., a molecular label).

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification does not produce circularized transcripts.

In some embodiments, the methods disclosed herein further comprise conducting a polymerase chain reaction on the labeled nucleic acid (e.g., labeled-RNA, labeled-DNA, labeled-cDNA) to produce a labeled amplicon (e.g., a stochastically labeled amplicon). The labeled amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample label, a spatial label, a cell label, and/or a barcode sequence (e.g., a molecular label). The labeled amplicon can be a single-stranded molecule. The single-stranded molecule can comprise DNA, RNA, or a combination thereof. The nucleic acids of the disclosure can comprise synthetic or altered nucleic acids.

Amplification can comprise use of one or more non-natural nucleotides. Non-natural nucleotides can comprise photolabile or triggerable nucleotides. Examples of non-natural nucleotides can include, but are not limited to, peptide nucleic acid (PNA), morpholine and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise, for example, 1, 2, 3, 4, 5, 6, 7, 8, 9, 10, 11, 12, 13, 14, or 15 or more nucleotides. The one or more primers can comprise at least 1, 2, 3, 4, 5, 6, 7, 8, 9, 10, 11, 12, 13, 14, or 15 or more nucleotides. The one or more primers can comprise less than 12-15 nucleotides. The one or more primers can anneal to at least a portion of the plurality of labeled targets (e.g., stochastically labeled targets). The one or more primers can anneal to the 3' end or 5' end of the plurality of labeled targets. The one or more primers can anneal to an internal region of the plurality of labeled targets. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled targets. The one or more primers can comprise a fixed panel of primers. The one or more primers can comprise at least one or more custom primers. The one or more primers can comprise at least one or more control primers. The one or more primers can comprise at least one or more gene-specific primers.

The one or more primers can comprise a universal primer. The universal primer can anneal to a universal primer binding site. The one or more custom primers can anneal to a first sample label, a second sample label, a spatial label, a cell label, a barcode sequence (e.g., a molecular label), a target, or any combination thereof. The one or more primers can comprise a universal primer and a custom primer. The custom primer can be designed to amplify one or more targets. The targets can comprise a subset of the total nucleic acids in one or more samples. The targets can comprise a subset of the total labeled targets in one or more samples. The one or more primers can comprise at least 96 or more custom primers. The one or more primers can comprise at least 960 or more custom primers. The one or more primers can comprise at least 9600 or more custom primers. The one or more custom primers can anneal to two or more different labeled nucleic acids. The two or more different labeled nucleic acids can correspond to one or more genes.

Any amplification scheme can be used in the methods of the present disclosure. For example, in one scheme, the first round PCR can amplify molecules attached to the bead using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and barcode sequence (e.g., molecular label) on read 1, the gene on read 2, and the sample index on index 1 read.

In some embodiments, nucleic acids can be removed from the substrate using chemical cleavage. For example, a chemical group or a modified base present in a nucleic acid can be used to facilitate its removal from a solid support. For example, an enzyme can be used to remove a nucleic acid from a substrate. For example, a nucleic acid can be removed from a substrate through a restriction endonuclease digestion. For example, treatment of a nucleic acid containing a dUTP or ddUTP with uracil-d-glycosylase (UDG) can be used to remove a nucleic acid from a substrate. For example, a nucleic acid can be removed from a substrate using an enzyme that performs nucleotide excision, such as a base excision repair enzyme, such as an apurinic/apyrimidinic (AP) endonuclease. In some embodiments, a nucleic acid can be removed from a substrate using a photocleavable group and light. In some embodiments, a cleavable linker can be used to remove a nucleic acid from the substrate. For example, the cleavable linker can comprise at least one of biotin/avidin, biotin/streptavidin, biotin/neutravidin, Ig-protein A, a photo-labile linker, acid or base labile linker group, or an aptamer.

When the probes are gene-specific, the molecules can hybridize to the probes and be reverse transcribed and/or amplified. In some embodiments, after the nucleic acid has been synthesized (e.g., reverse transcribed), it can be amplified. Amplification can be performed in a multiplex manner, wherein multiple target nucleic acid sequences are amplified simultaneously. Amplification can add sequencing adaptors to the nucleic acid.

In some embodiments, amplification can be performed on the substrate, for example, with bridge amplification. cDNAs can be homopolymer tailed in order to generate a compatible end for bridge amplification using oligo(dT) probes on the substrate. In bridge amplification, the primer that is complementary to the 3' end of the template nucleic acid can be the first primer of each pair that is covalently attached to the solid particle. When a sample containing the template nucleic acid is contacted with the particle and a single thermal cycle is performed, the template molecule can be annealed to the first primer and the first primer is elongated in the forward direction by addition of nucleotides to form a duplex molecule consisting of the template molecule and a newly formed DNA strand that is complementary to the template. In the heating step of the next cycle, the duplex molecule can be denatured, releasing the template molecule from the particle and leaving the complementary DNA strand attached to the particle through the first primer. In the annealing stage of the annealing and elongation step that follows, the complementary strand can hybridize to the second primer, which is complementary to a segment of the complementary strand at a location removed from the first primer. This hybridization can cause the complementary strand to form a bridge between the first and second primers secured to the first primer by a covalent bond and to the second primer by hybridization. In the elongation stage, the second primer can be elongated in the reverse direction by the addition of nucleotides in the same reaction mixture, thereby converting the bridge to a double-stranded bridge. The next cycle then begins, and the double-stranded bridge can be denatured to yield two single-stranded nucleic acid molecules, each having one end attached to the particle surface via the first and second primers, respectively, with the other end of each unattached. In the annealing and elongation step of this second cycle, each strand can hybridize to a further complementary primer, previously unused, on the same particle, to form new single-strand bridges. The two previously unused primers that are now hybridized elongate to convert the two new bridges to double-strand bridges.

The amplification reactions can comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids.

Amplification of the labeled nucleic acids can comprise PCR-based methods or non-PCR based methods. Amplification of the labeled nucleic acids can comprise exponential amplification of the labeled nucleic acids. Amplification of the labeled nucleic acids can comprise linear amplification of the labeled nucleic acids. Amplification can be performed by polymerase chain reaction (PCR). PCR can refer to a reaction for the in vitro amplification of specific DNA sequences by the simultaneous primer extension of complementary strands of DNA. PCR can encompass derivative forms of the reaction, including but not limited to, RT-PCR, real-time PCR, nested PCR, quantitative PCR, multiplexed PCR, digital PCR, suppression PCR, semi-suppressive PCR and assembly PCR.

In some embodiments, amplification of the labeled nucleic acids comprises non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), a Qβ replicase (Qβ), use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and/or ramification extension amplification (RAM).

In some embodiments, the methods disclosed herein further comprise conducting a nested polymerase chain reaction on the amplified amplicon (e.g., target). The amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample tag or molecular identifier label. Alternatively, the amplicon can be a single-stranded molecule. The single-stranded molecule can comprise DNA, RNA, or a combination thereof. The nucleic acids of the present invention can comprise synthetic or altered nucleic acids.

In some embodiments, the method comprises repeatedly amplifying the labeled nucleic acid to produce multiple amplicons. The methods disclosed herein can comprise conducting at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Amplification can further comprise adding one or more control nucleic acids to one or more samples comprising a plurality of nucleic acids. Amplification can further comprise adding one or more control nucleic acids to a plurality of nucleic acids. The control nucleic acids can comprise a control label.

Amplification can comprise use of one or more non-natural nucleotides. Non-natural nucleotides can comprise photolabile and/or triggerable nucleotides. Examples of non-natural nucleotides include, but are not limited to, peptide nucleic acid (PNA), morpholine and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise one or more oligonucleotides. The one or more oligonucleotides can comprise at least about 7-9 nucleotides. The one or more oligonucleotides can comprise less than 12-15 nucleotides. The one or more primers can anneal to at least a portion of the plurality of labeled nucleic acids. The one or more primers can anneal to the 3' end and/or 5' end of the plurality of labeled nucleic acids. The one or more primers can anneal to an internal region of the plurality of labeled nucleic acids. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled nucleic acids. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. The one or more custom primers can anneal to the first sample tag, the second sample tag, the molecular identifier label, the nucleic acid or a product thereof. The one or more primers can comprise a universal primer and a custom primer. The custom primer can be designed to amplify one or more target nucleic acids. The target nucleic acids can comprise a subset of the total nucleic acids in one or more samples. In some embodiments, the primers are the probes attached to the array of the disclosure.

In some embodiments, barcoding (e.g., stochastically barcoding) the plurality of targets in the sample further comprises generating an indexed library of the barcoded targets (e.g., stochastically barcoded targets) or barcoded fragments of the targets. The barcode sequences of different barcodes (e.g., the molecular labels of different stochastic barcodes) can be different from one another. Generating an indexed library of the barcoded targets includes generating a plurality of indexed polynucleotides from the plurality of targets in the sample. For example, for an indexed library of the barcoded targets comprising a first indexed target and a second indexed target, the label region of the first indexed polynucleotide can differ from the label region of the second indexed polynucleotide by, by about, by at least, or by at most, 1, 2, 3, 4, 5, 6, 7, 8, 9, 10, 20, 30, 40, 50, or a number or a range between any two of these values, nucleotides. In some embodiments, generating an indexed library of the barcoded targets includes contacting a plurality of targets, for example mRNA molecules, with a plurality of oligonucleotides including a poly(T) region and a label region; and conducting a first strand synthesis using a reverse transcriptase to produce single-strand labeled cDNA molecules each comprising a cDNA region and a label region, wherein the plurality of targets includes at least two mRNA molecules of different sequences and the plurality of oligonucleotides includes at least two oligonucleotides of different sequences. Generating an indexed library of the barcoded targets can further comprise amplifying the single-strand labeled cDNA molecules to produce double-strand labeled cDNA molecules; and conducting nested PCR on the double-strand labeled cDNA molecules to produce labeled amplicons. In some embodiments, the method can include generating an adaptor-labeled amplicon.

Barcoding (e.g., stochastic barcoding) can include using nucleic acid barcodes or tags to label individual nucleic acid (e.g., DNA or RNA) molecules. In some embodiments, it involves adding DNA barcodes or tags to cDNA molecules as they are generated from mRNA. Nested PCR can be performed to minimize PCR amplification bias. Adaptors can be added for sequencing using, for example, next generation sequencing (NGS). The sequencing results can be used to determine cell labels, molecular labels, and sequences of nucleotide fragments of the one or more copies of the targets, for example at block 232 of FIG. 2.

Figure 3:
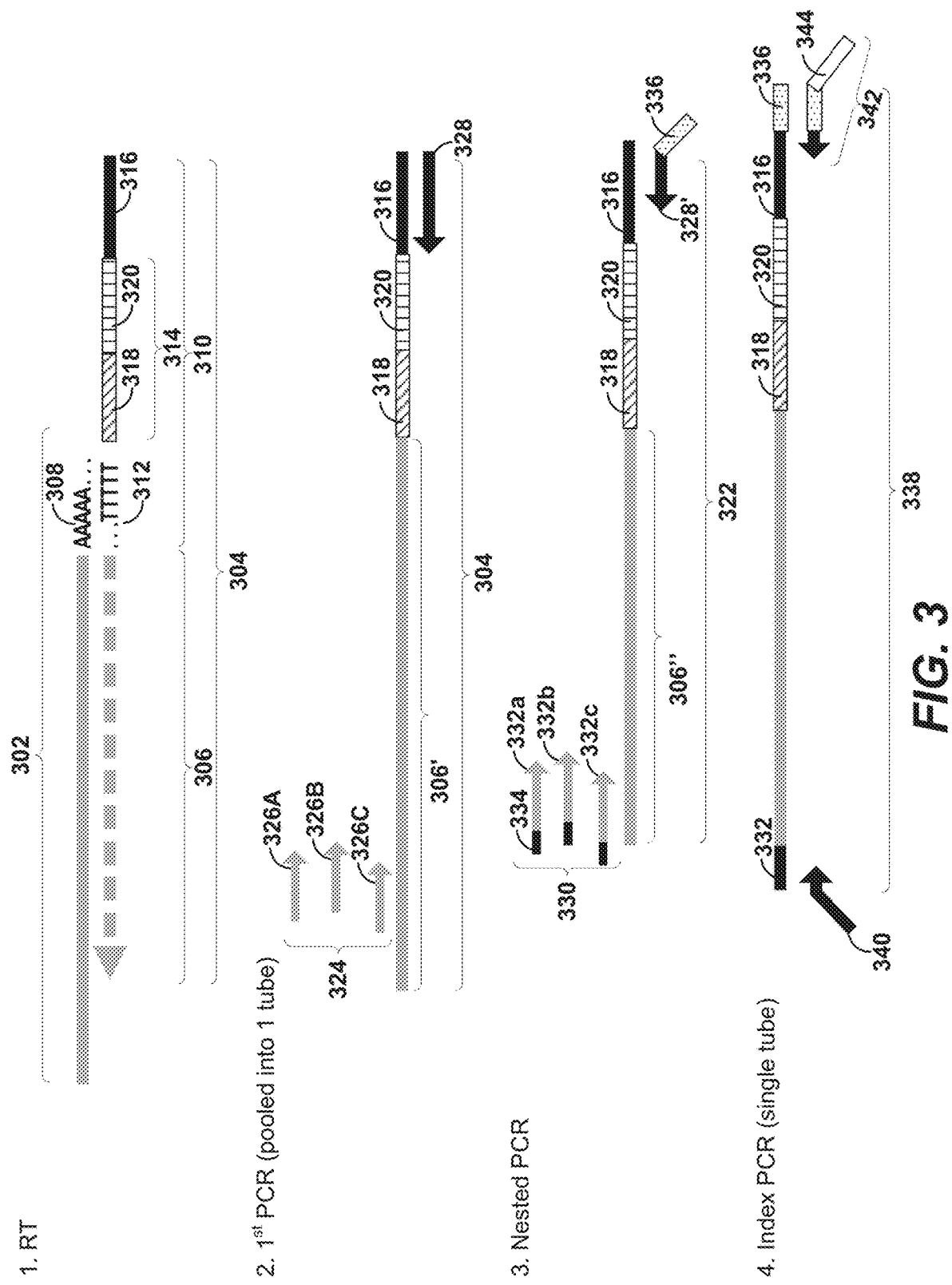
FIG. 3 is a schematic illustration showing a non-limiting exemplary process for generating an indexed library of the stochastically barcoded targets from a plurality of targets.

FIG. 3 is a schematic illustration showing a non-limiting exemplary process of generating an indexed library of the barcoded targets (e.g., stochastically barcoded targets), such as barcoded mRNAs or fragments thereof, barcoded identifier sequences of cellular component binding reagents, etc. As shown in step 1, the reverse transcription process can encode each mRNA molecule with a unique molecular label, a cell label, and a universal PCR site. In particular, RNA molecules 302 can be reverse transcribed to produce labeled cDNA molecules 304, including a cDNA region 306, by hybridization (e.g., stochastic hybridization) of a set of barcodes (e.g., stochastic barcodes) 310 to the poly(A) tail region 308 of the RNA molecules 302. Each of the barcodes 310 can comprise a target-binding region, for example a poly(dT) region 312, a label region 314 (e.g., a barcode sequence or a molecule), and a universal PCR region 316.

In some embodiments, the cell label can include 3 to 20 nucleotides. In some embodiments, the molecular label can include 3 to 20 nucleotides. In some embodiments, each of the plurality of stochastic barcodes further comprises one or more of a universal label and a cell label, wherein universal labels are the same for the plurality of stochastic barcodes on the solid support and cell labels are the same for the plurality of stochastic barcodes on the solid support. In some embodiments, the universal label can include 3 to 20 nucleotides. In some embodiments, the cell label comprises 3 to 20 nucleotides.

In some embodiments, the label region 314 can include a barcode sequence or a molecular label 318 and a cell label 320. In some embodiments, the label region 314 can include one or more of a universal label, a dimension label, and a cell label. The barcode sequence or molecular label 318 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The cell label 320 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The universal label can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. Universal labels can be the same for the plurality of stochastic barcodes on the solid support and cell labels are the same for the plurality of stochastic barcodes on the solid support. The dimension label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length.

In some embodiments, the label region 314 can comprise, comprise about, comprise at least, or comprise at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different labels, such as a barcode sequence or a molecular label 318 and a cell label 320. Each label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length. A set of barcodes or stochastic barcodes 310 can contain, contain about, contain at least, or can be at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, barcodes or stochastic barcodes 310. And the set of barcodes or stochastic barcodes 310 can, for example, each contain a unique label region 314. The labeled cDNA molecules 304 can be purified to remove excess barcodes or stochastic barcodes 310. Purification can comprise Ampure bead purification.

As shown in step 2, products from the reverse transcription process in step 1 can be pooled into 1 tube and PCR amplified with a $1^{st}$ PCR primer pool and a $1^{st}$ universal PCR primer. Pooling is possible because of the unique label region 314. In particular, the labeled cDNA molecules 304 can be amplified to produce nested PCR labeled amplicons 322. Amplification can comprise multiplex PCR amplification. Amplification can comprise a multiplex PCR amplification with 96 multiplex primers in a single reaction volume. In some embodiments, multiplex PCR amplification can utilize, utilize about, utilize at least, or utilize at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, multiplex primers in a single reaction volume. Amplification can comprise using a $1^{st}$ PCR primer pool 324 comprising custom primers 326A-C targeting specific genes and a universal primer 328. The custom primers 326 can hybridize to a region within the cDNA portion 306' of the labeled cDNA molecule 304. The universal primer 328 can hybridize to the universal PCR region 316 of the labeled cDNA molecule 304.

As shown in step 3 of FIG. 3, products from PCR amplification in step 2 can be amplified with a nested PCR primers pool and a $2^{nd}$ universal PCR primer. Nested PCR can minimize PCR amplification bias. In particular, the nested PCR labeled amplicons 322 can be further amplified by nested PCR. The nested PCR can comprise multiplex PCR with nested PCR primers pool 330 of nested PCR primers 332a-c and a $2^{nd}$ universal PCR primer 328' in a single reaction volume. The nested PCR primer pool 328 can contain, contain about, contain at least, or contain at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different nested PCR primers 330. The nested PCR primers 332 can contain an adaptor 334 and hybridize to a region within the cDNA portion 306" of the labeled amplicon 322. The universal primer 328' can contain an adaptor 336 and hybridize to the universal PCR region 316 of the labeled amplicon 322. Thus, step 3 produces adaptor-labeled amplicon 338. In some embodiments, nested PCR primers 332 and the $2^{nd}$ universal PCR primer 328' may not contain the adaptors 334 and 336. The adaptors 334 and 336 can instead be ligated to the products of nested PCR to produce adaptor-labeled amplicon 338.

As shown in step 4, PCR products from step 3 can be PCR amplified for sequencing using library amplification primers. In particular, the adaptors 334 and 336 can be used to conduct one or more additional assays on the adaptor-labeled amplicon 338. The adaptors 334 and 336 can be hybridized to primers 340 and 342. The one or more primers 340 and 342 can be PCR amplification primers. The one or more primers 340 and 342 can be sequencing primers. The one or more adaptors 334 and 336 can be used for further amplification of the adaptor-labeled amplicons 338. The one or more adaptors 334 and 336 can be used for sequencing the adaptor-labeled amplicon 338. The primer 342 can contain a plate index 344 so that amplicons generated using the same set of barcodes or stochastic barcodes 310 can be sequenced in one sequencing reaction using next generation sequencing (NGS).

Cellular Component-Binding Reagents

Compositions Comprising Cellular Component Binding Reagents Associated with Oligonucleotides Some embodiments disclosed herein provide a plurality of compositions each comprising a cellular component binding reagent (such as a protein binding reagent) that is conjugated with an oligonucleotide, wherein the oligonucleotide comprises a unique identifier for the cellular component binding reagent to which it is conjugated. Cellular component binding reagents (such as barcoded antibodies) and their uses (such as sample indexing of cells) have been described in U.S. Patent Application Publication No. US2018/0088112 and U.S. Patent Application Publication No. US2018/0346970; the content of each of these is incorporated herein by reference in its entirety.

In some embodiments, the cellular component binding reagent is capable of specifically binding to a cellular component target. For example, a binding target of the cellular component binding reagent can be, or comprise, a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof. In some embodiments, the cellular component binding reagent (e.g., a protein binding reagent) is capable of specifically binding to an antigen target or a protein target. In some embodiments, each of the oligonucleotides can comprise a barcode, such as a stochastic barcode. A barcode can comprise a barcode sequence (e.g., a molecular label), a cell label, a sample label, or any combination thereof. In some embodiments, each of the oligonucleotides can comprise a linker. In some embodiments, each of the oligonucleotides can comprise a binding site for an oligonucleotide probe, such as a poly(A) tail. For example, the poly(A) tail can be, e.g., unanchored to a solid support or anchored to a solid support. The poly(A) tail can be from about 10 to 50 nucleotides in length. In some embodiments, the poly(A) tail can be 18 nucleotides in length. The oligonucleotides can comprise deoxyribonucleotides, ribonucleotides, or both.

The unique identifiers can be, for example, a nucleotide sequence having any suitable length, for example, from about 4 nucleotides to about 200 nucleotides. In some embodiments, the unique identifier is a nucleotide sequence of 25 nucleotides to about 45 nucleotides in length. In some embodiments, the unique identifier can have a length that is, is about, is less than, is greater than, 4 nucleotides, 5 nucleotides, 6 nucleotides, 7 nucleotides, 8 nucleotides, 9 nucleotides, 10 nucleotides, 15 nucleotides, 20 nucleotides, 25 nucleotides, 30 nucleotides, 35 nucleotides, 40 nucleotides, 45 nucleotides, 50 nucleotides, 55 nucleotides, 60 nucleotides, 70 nucleotides, 80 nucleotides, 90 nucleotides, 100 nucleotides, 200 nucleotides, or a range that is between any two of the above values.

In some embodiments, the unique identifiers are selected from a diverse set of unique identifiers. The diverse set of unique identifiers can comprise, or comprise about, 20, 30, 40, 50, 60, 70, 80, 90, 100, 200, 300, 400, 500, 600, 700, 800, 900, 1000, 2000, 5000, or a number or a range between any two of these values, different unique identifiers. The diverse set of unique identifiers can comprise at least, or comprise at most, 20, 30, 40, 50, 60, 70, 80, 90, 100, 200, 300, 400, 500, 600, 700, 800, 900, 1000, 2000, or 5000, different unique identifiers. In some embodiments, the set of unique identifiers is designed to have minimal sequence homology to the DNA or RNA sequences of the sample to be analyzed. In some embodiments, the sequences of the set of unique identifiers are different from each other, or the complement thereof, by, or by about, 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, or a number or a range between any two of these values. In some embodiments, the sequences of the set of unique identifiers are different from each other, or the complement thereof, by at least, or by at most, 1 nucleotide, 2 nucleotides, 3 nucleotides, 4 nucleotides, 5 nucleotides, 6 nucleotides, 7 nucleotides, 8 nucleotides, 9 nucleotides, 10 nucleotides. In some embodiments, the sequences of the set of unique identifiers are different from each other, or the complement thereof, by at least 3%, at least 5%, at least 8%, at least 10%, at least 15%, at least 20%, or more.

In some embodiments, the unique identifiers can comprise a binding site for a primer, such as universal primer. In some embodiments, the unique identifiers can comprise at least two binding sites for a primer, such as a universal primer. In some embodiments, the unique identifiers can comprise at least three binding sites for a primer, such as a universal primer. The primers can be used for amplification of the unique identifiers, for example, by PCR amplification. In some embodiments, the primers can be used for nested PCR reactions.

Any suitable cellular component binding reagents are contemplated in this disclosure, such as protein binding reagents, antibodies or fragments thereof, aptamers, small molecules, ligands, peptides, oligonucleotides, etc., or any combination thereof. In some embodiments, the cellular component binding reagents can be polyclonal antibodies, monoclonal antibodies, recombinant antibodies, single chain antibody (sc-Ab), or fragments thereof, such as Fab, Fv, etc. In some embodiments, the plurality of cellular component binding reagents can comprise, or comprise about, 20, 30, 40, 50, 60, 70, 80, 90, 100, 200, 300, 400, 500, 600, 700, 800, 900, 1000, 2000, 5000, or a number or a range between any two of these values, different cellular component reagents. In some embodiments, the plurality of cellular component binding reagents can comprise at least, or comprise at most, 20, 30, 40, 50, 60, 70, 80, 90, 100, 200, 300, 400, 500, 600, 700, 800, 900, 1000, 2000, or 5000, different cellular component reagents.

The oligonucleotide can be conjugated with the cellular component binding reagent through various mechanism. In some embodiments, the oligonucleotide can be conjugated with the cellular component binding reagent covalently. In some embodiment, the oligonucleotide can be conjugated with the cellular component binding reagent non-covalently. In some embodiments, the oligonucleotide is conjugated with the cellular component binding reagent through a linker. The linker can be, for example, cleavable or detachable from the cellular component binding reagent and/or the oligonucleotide. In some embodiments, the linker can comprise a chemical group that reversibly attaches the oligonucleotide to the cellular component binding reagents. The chemical group can be conjugated to the linker, for example, through an amine group. In some embodiments, the linker can comprise a chemical group that forms a stable bond with another chemical group conjugated to the cellular component binding reagent. For example, the chemical group can be a UV photocleavable group, a disulfide bond, a streptavidin, a biotin, an amine, etc. In some embodiments, the chemical group can be conjugated to the cellular component binding reagent through a primary amine on an amino acid, such as lysine, or the N-terminus. Commercially available conjugation kits, such as the Protein-Oligo Conjugation Kit (Solulink, Inc., San Diego, California), the Thunder-Link® oligo conjugation system (Innova Biosciences, Cambridge, United Kingdom), etc., can be used to conjugate the oligonucleotide to the cellular component binding reagent.

The oligonucleotide can be conjugated to any suitable site of the cellular component binding reagent (e.g., a protein binding reagent), as long as it does not interfere with the specific binding between the cellular component binding reagent and its cellular component target. In some embodiments, the cellular component binding reagent is a protein, such as an antibody. In some embodiments, the cellular component binding reagent is not an antibody. In some embodiments, the oligonucleotide can be conjugated to the antibody anywhere other than the antigen-binding site, for example, the Fc region, the $C_H1$ domain, the $C_H2$ domain, the $C_H3$ domain, the $C_L$ domain, etc. Methods of conjugating oligonucleotides to cellular component binding reagents (e.g., antibodies) have been previously disclosed, for example, in U.S. Pat. No. 6,531,283, the content of which is hereby expressly incorporated by reference in its entirety. Stoichiometry of oligonucleotide to cellular component binding reagent can be varied. To increase the sensitivity of detecting the cellular component binding reagent specific oligonucleotide in sequencing, it may be advantageous to increase the ratio of oligonucleotide to cellular component binding reagent during conjugation. In some embodiments, each cellular component binding reagent can be conjugated with a single oligonucleotide molecule. In some embodiments, each cellular component binding reagent can be conjugated with more than one oligonucleotide molecule, for example, at least, or at most, 2, 3, 4, 5, 10, 20, 30, 40, 50, 100, 1000, or a number or a range between any two of these values, oligonucleotide molecules wherein each of the oligonucleotide molecule comprises the same, or different, unique identifiers. In some embodiments, each cellular component binding reagent can be conjugated with more than one oligonucleotide molecule, for example, at least, or at most, 2, 3, 4, 5, 10, 20, 30, 40, 50, 100, 1000, oligonucleotide molecules, wherein each of the oligonucleotide molecule comprises the same, or different, unique identifiers.

In some embodiments, the plurality of cellular component binding reagents are capable of specifically binding to a plurality of cellular component targets in a sample, such as a single cell, a plurality of cells, a tissue sample, a tumor sample, a blood sample, or the like. In some embodiments, the plurality of cellular component targets comprises a cell-surface protein, a cell marker, a B-cell receptor, a T-cell receptor, an antibody, a major histocompatibility complex, a tumor antigen, a receptor, or any combination thereof. In some embodiments, the plurality of cellular component targets can comprise intracellular cellular components. In some embodiments, the plurality of cellular component targets can comprise intracellular cellular components. In some embodiments, the plurality of cellular components can be, or be about, 1%, 2%, 3%, 4%, 5%, 6%, 7%, 8%, 9%, 10%, 20%, 30%, 40%, 50%, 60%, 70%, 80%, 90%, 95%, 98%, 99%, or a number or a range between any two of these values, of all the cellular components (e.g., proteins) in a cell or an organism. In some embodiments, the plurality of cellular components can be at least, or be at most, 1%, 2%, 3%, 4%, 5%, 6%, 7%, 8%, 9%, 10%, 20%, 30%, 40%, 50%, 60%, 70%, 80%, 90%, 95%, 98%, or 99%, of all the cellular components (e.g., proteins) in a cell or an organism. In some embodiments, the plurality of cellular component targets can comprise, or comprise about, 2, 3, 4, 5, 10, 20, 30, 40, 50, 100, 1000, 10000, or a number or a range between any two of these values, different cellular component targets. In some embodiments, the plurality of cellular component targets can comprise at least, or comprise at most, 2, 3, 4, 5, 10, 20, 30, 40, 50, 100, 1000, 10000, different cellular component targets.

Figure 4:
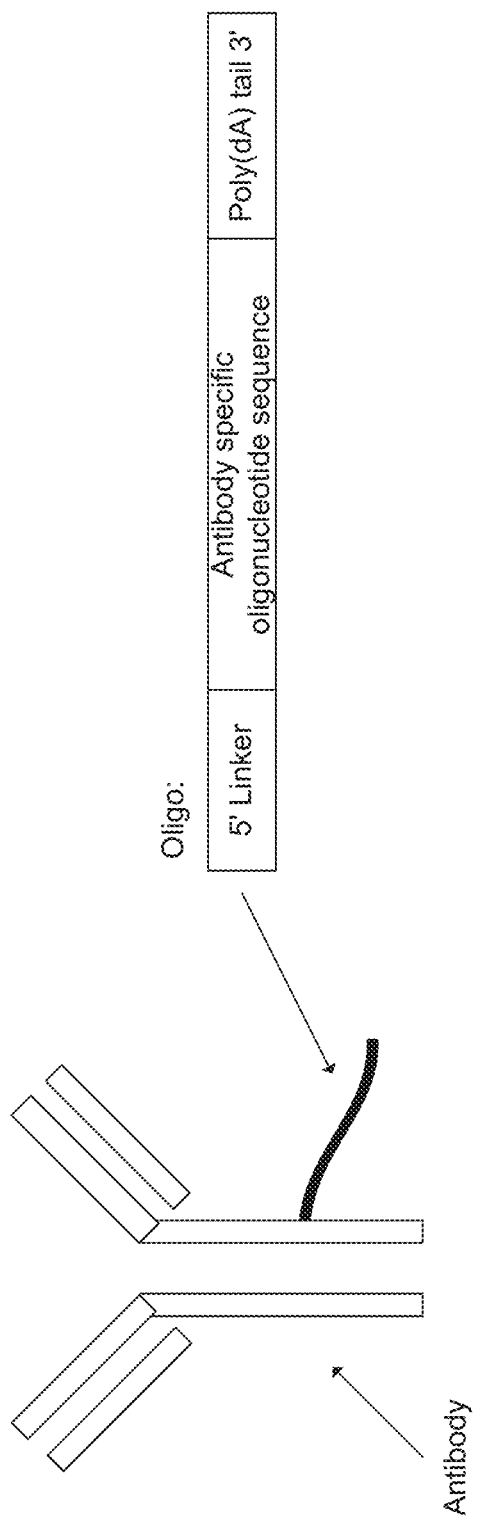
FIG. 4 shows a schematic illustration of an exemplary protein binding reagent (antibody illustrated here) associated with an oligonucleotide comprising a unique identifier for the protein binding reagent.

FIG. 4 shows a schematic illustration of an exemplary cellular component binding reagent (e.g., an antibody) that is associated (e.g., conjugated) with an oligonucleotide comprising a unique identifier sequence for the antibody. An oligonucleotide-conjugated with a cellular component binding reagent, an oligonucleotide for conjugation with a cellular component binding reagent, or an oligonucleotide previously conjugated with a cellular component binding reagent can be referred to herein as an antibody oligonucleotide (abbreviated as a binding reagent oligonucleotide). An oligonucleotide-conjugated with an antibody, an oligonucleotide for conjugation with an antibody, or an oligonucleotide previously conjugated with an antibody can be referred to herein as an antibody oligonucleotide (abbreviated as an "AbOligo" or "AbO"). The oligonucleotide can also comprise additional components, including but not limited to, one or more linker, one or more unique identifier for the antibody, optionally one or more barcode sequences (e.g., molecular labels), and a poly(A) tail. In some embodiments, the oligonucleotide can comprise, from 5' to 3', a linker, a unique identifier, a barcode sequence (e.g., a molecular label), and a poly(A) tail. An antibody oligonucleotide can be an mRNA mimic.

Figure 5:
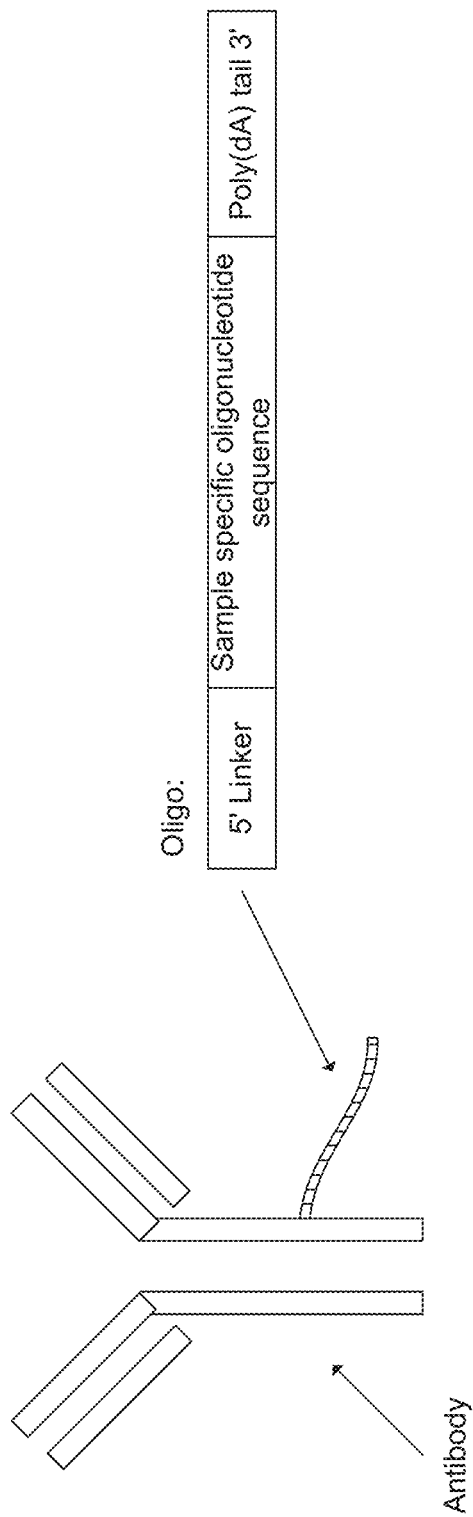
FIG. 5 shows a schematic illustration of an exemplary binding reagent (antibody illustrated here) associated with an oligonucleotide comprising a unique identifier for sample indexing to determine cells from the same or different samples.

FIG. 5 shows a schematic illustration of an exemplary cellular component binding reagent (e.g., an antibody) that is associated (e.g., conjugated) with an oligonucleotide comprising a sample indexing sequence for the antibody. The cellular component binding reagent can be capable of specifically binding to at least one cellular component target, such as an antigen target or a protein target. A binding reagent oligonucleotide (e.g., a sample indexing oligonucleotide, or an antibody oligonucleotide) can comprise a sequence (e.g., a sample indexing sequence) for performing the methods of the disclosure. For example, a sample indexing oligonucleotide can comprise a sample indexing sequence for identifying sample origin of one or more cells of a sample. Indexing sequences (e.g., sample indexing sequences) of at least two compositions comprising two cellular component binding reagents (e.g., sample indexing compositions) of the plurality of compositions comprising cellular component binding reagents can comprise different sequences. In some embodiments, the binding reagent oligonucleotide is not homologous to genomic sequences of a species. The binding reagent oligonucleotide can be configured to be (or can be) detachable or non-detachable from the cellular component binding reagent.

The oligonucleotide conjugated to a cellular component binding reagent can, for example, comprise a barcode sequence (e.g., a molecular label sequence), a poly(A) tail, or a combination thereof. An oligonucleotide conjugated to a cellular component binding reagent can be an mRNA mimic. In some embodiments, the sample indexing oligonucleotide comprises a sequence complementary to a capture sequence of at least one barcode of the plurality of barcodes. A target binding region of the barcode can comprise the capture sequence. The target binding region can, for example, comprise a poly(dT) region. In some embodiments, the sequence of the sample indexing oligonucleotide complementary to the capture sequence of the barcode can comprise a poly(A) tail. The sample indexing oligonucleotide can comprise a molecular label.

In some embodiments, the binding reagent oligonucleotide (e.g., the sample oligonucleotide) comprises a nucleotide sequence of, or a nucleotide sequence of about, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, nucleotides in length. In some embodiments, the binding reagent oligonucleotide comprises a nucleotide sequence of at least, or of at most, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000, nucleotides in length.

The cellular component-binding reagent comprises a specific binding member that specifically binds to a cellular component target. The affinity between a pair of a specific binding member and the cellular component target to which it specifically binds may vary, where in some instances they may specifically bind to each other in a binding complex that is characterized by a KD (dissociation constant) of $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, or $10^{-15}$ M or less (it is noted that these values can apply to other specific binding pair interactions mentioned elsewhere in this description, in certain embodiments). In some embodiments, the cellular component binding reagent comprises an antibody, a tetramer, an aptamers, a protein scaffold, or a combination thereof. The binding reagent oligonucleotide can be conjugated to the cellular component binding reagent, for example, through a linker. The binding reagent oligonucleotide can comprise the linker. The linker can comprise a chemical group. The chemical group can be reversibly, or irreversibly, attached to the molecule of the cellular component binding reagent. The chemical group can be selected from the group consisting of a UV photocleavable group, a disulfide bond, a streptavidin, a biotin, an amine, and any combination thereof.

In some embodiments, the cellular component binding reagent can bind to ADAM10, CD156c, ANO6, ATP1B2, ATP1B3, BSG, CD147, CD109, CD230, CD29, CD298, ATP1B3, CD44, CD45, CD47, CD51, CD59, CD63, CD97, CD98, SLC3A2, CLDND1, HLA-ABC, ICAM1, ITFG3, MPZL1, NA K ATPase alpha1, ATP1A1, NPTN, PMCA ATPase, ATP2B1, SLC1A5, SLC29A1, SLC2A1, SLC44A2, or any combination thereof.

In some embodiments, the protein target is, or comprises, an extracellular protein, an intracellular protein, or any combination thereof. In some embodiments, the antigen or protein target is, or comprises, a cell-surface protein, a cell marker, a B-cell receptor, a T-cell receptor, a major histocompatibility complex, a tumor antigen, a receptor, an integrin, or any combination thereof. The antigen or protein target can be, or comprise, a lipid, a carbohydrate, or any combination thereof. The protein target can be selected from a group comprising a number of protein targets. The number of antigen target or protein targets can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values. The number of protein targets can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000.

The cellular component binding reagent (e.g., a protein binding reagent) can be associated with two or more binding reagent oligonucleotide (e.g., sample indexing oligonucleotides) with an identical sequence. The cellular component binding reagent can be associated with two or more binding reagent oligonucleotides with different sequences. The number of binding reagent oligonucleotides associated with the cellular component binding reagent can be different in different implementations. In some embodiments, the number of binding reagent oligonucleotides, whether having an identical sequence, or different sequences, can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values. In some embodiments, the number of binding reagent oligonucleotides can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, or 1000.

The plurality of compositions comprising cellular component binding reagents (e.g., the plurality of sample indexing compositions) can comprise one or more additional cellular component binding reagents not conjugated with the binding reagent oligonucleotide (such as sample indexing oligonucleotide), which is also referred to herein as the binding reagent oligonucleotide-free cellular component binding reagent (such as sample indexing oligonucleotide-free cellular component binding reagent). The number of additional cellular component binding reagents in the plurality of compositions can be different in different implementations. In some embodiments, the number of additional cellular component binding reagents can be, or be about, 1, 2, 3, 4, 5, 6, 7, 8, 9, 10, 20, 30, 40, 50, 60, 70, 80, 90, 100, or a number or a range between any two of these values. In some embodiments, the number of additional cellular component binding reagents can be at least, or be at most, 1, 2, 3, 4, 5, 6, 7, 8, 9, 10, 20, 30, 40, 50, 60, 70, 80, 90, or 100. The cellular component binding reagent and any of the additional cellular component binding reagents can be identical, in some embodiments.

In some embodiments, a mixture comprising cellular component binding reagent(s) that is conjugated with one or more binding reagent oligonucleotides (e.g., sample indexing oligonucleotides) and cellular component binding reagent(s) that is not conjugated with binding reagent oligonucleotides is provided. The mixture can be used in some embodiments of the methods disclosed herein, for example, to contact the sample(s) and/or cell(s). The ratio of (1) the number of a cellular component binding reagent conjugated with a binding reagent oligonucleotide and (2) the number of another cellular component binding reagent (e.g., the same cellular component binding reagent) not conjugated with the binding reagent oligonucleotide (e.g., sample indexing oligonucleotide) or other binding reagent oligonucleotide(s) in the mixture can be different in different implementations. In some embodiments, the ratio can be, or be about, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, 1:10000, or a number or a range between any two of the values. In some embodiments, the ratio can be at least, or be at most, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, or 1:10000.

In some embodiments, the ratio can be, or be about, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values. In some embodiments, the ratio can be at least, or be at most, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1.

A cellular component binding reagent can be conjugated with a binding reagent oligonucleotide (e.g., a sample indexing oligonucleotide), or not. In some embodiments, the percentage of the cellular component binding reagent conjugated with a binding reagent oligonucleotide (e.g., a sample indexing oligonucleotide) in a mixture comprising the cellular component binding reagent that is conjugated with the binding reagent oligonucleotide and the cellular component binding reagent(s) that is not conjugated with the binding reagent oligonucleotide can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of the cellular component binding reagent conjugated with a sample indexing oligonucleotide in a mixture can be at least, or be at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

In some embodiments, the percentage of the cellular component binding reagent not conjugated with a binding reagent oligonucleotide (e.g., a sample indexing oligonucleotide) in a mixture comprising a cellular component binding reagent conjugated with a binding reagent oligonucleotide (e.g., a sample indexing oligonucleotide) and the cellular component binding reagent that is not conjugated with the sample indexing oligonucleotide can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of the cellular component binding reagent not conjugated with a binding reagent oligonucleotide in a mixture can be at least, or be at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

Binding Reagent Oligonucleotides Associated with a Detectable Moiety

In some embodiments, the oligonucleotide associated with a cellular component-binding reagent (e.g., antibody oligonucleotide ("AbOligo" or "AbO"), binding reagent oligonucleotide, cellular component-binding reagent specific oligonucleotides, sample indexing oligonucleotides) is associated with one or more detectable moieties, e.g., where the binding reagent oligonucleotide comprises one or more detectable moieties (e.g., an optical moiety, a luminescent moiety, an electrochemically active moiety, a nanoparticle), where the binding reagent oligonucleotide is non-covalently bound to a detectable moiety, e.g., where the detectable moiety is part of a label nucleic acid hybridized to the binding reagent oligonucleotide, etc. Advantageously, in some embodiments, the association of the detectable moiety in the binding reagent oligonucleotide enables the cellular component-binding reagent to be employed for both fluorescence analysis (e.g., cell sorting) and sequence analysis (e.g., protein expression profiling).

Figure 9:
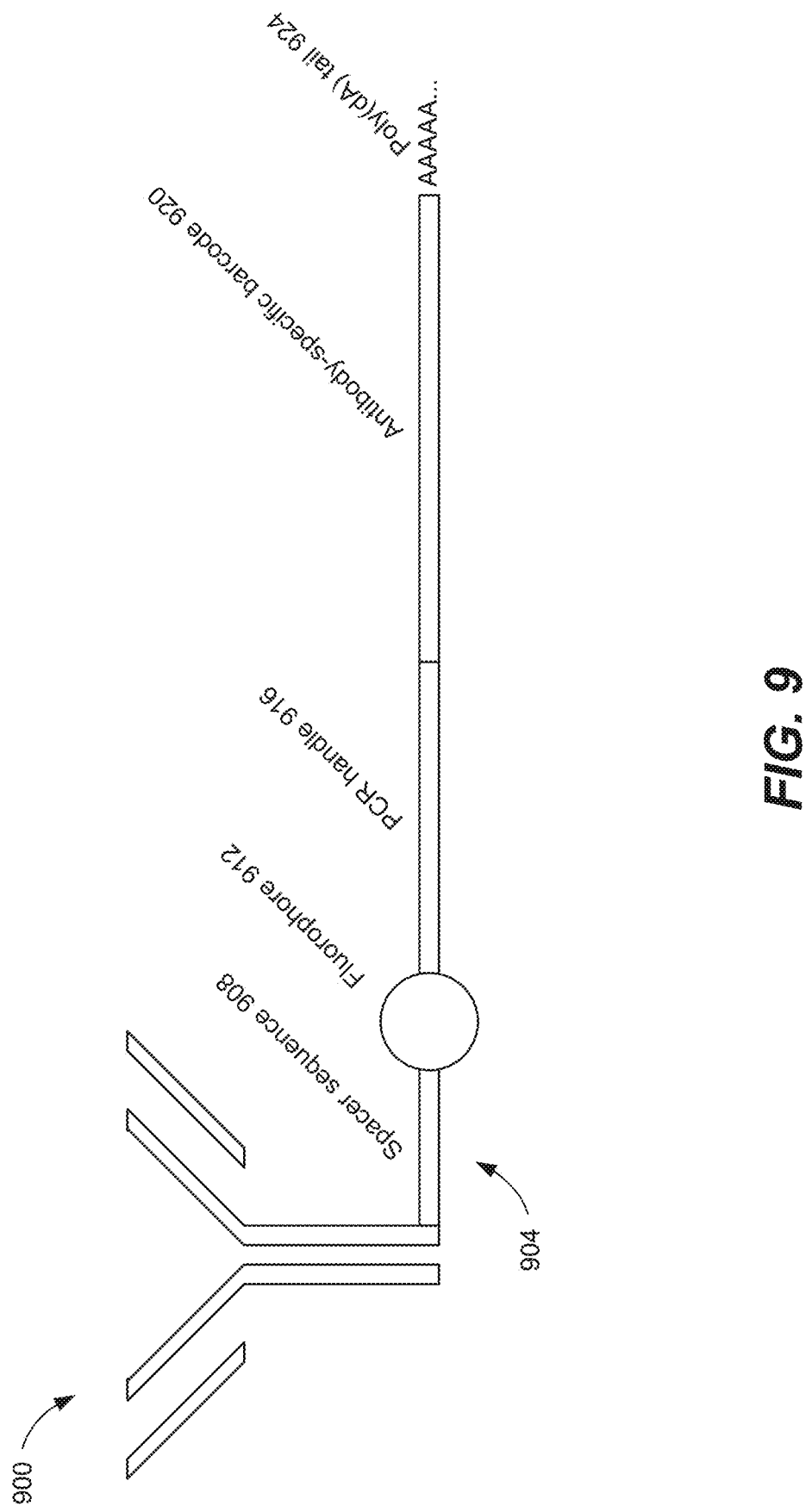
FIG. 9 shows a schematic illustration of a non-limiting exemplary protein binding reagent (an antibody illustrated here) associated with an oligonucleotide comprising a detectable moiety (a fluorophore illustrated here).

FIG. 9 shows a schematic illustration of a non-limiting exemplary binding reagent oligonucleotide 904 (antibody oligonucleotide illustrated here) that is associated with a binding reagent 900 (antibody illustrated here). A spacer sequence 908 (or a linker) can be situated between the binding reagent oligonucleotide 904 and the binding reagent 900. The spacer sequence 908 can be, for example, 1, 2, 3, 4, 5, 6, 7, 8, 9, 10, 11, 12, 13, 14, 15, 16, 17, 18, 19, or 20, or more nucleotides. The binding reagent oligonucleotide 904 can be an mRNA mimic. The binding reagent oligonucleotide 904 can comprise one or more fluorophores 912 (e.g., a fluorescent moiety, a fluorescent tag), which are thereby associated with the binding reagent oligonucleotide, as the binding reagent oligonucleotide comprises the one or more fluorophores. In some embodiments, the binding reagent oligonucleotide 904 comprises an alternative detectable moiety other than a fluorophore (e.g., an optical moiety, a luminescent moiety, an electrochemically active moiety, a nanoparticle). The binding reagent oligonucleotide 904 can comprise a poly(dA) tail 924. The poly(dA) tail 924 can enable capture of the binding reagent oligonucleotide 904. The binding reagent oligonucleotide 904 can include a unique identifier sequence 920 (such as an antibody-specific barcode or a sample indexing sequence). The antibody-specific barcode 920 can be specific to each antibody species. In some embodiments, the antibody barcode 920 can be the same for all or some of binding reagent oligonucleotides 904. In some embodiments, the antibody barcode 920 of different binding reagent oligonucleotides 904 are different.

The binding reagent oligonucleotide 904 can include a PCR handle 916 (e.g., a complete or partial Illumina R2 and/or P7 sequence) that can be used for amplification of the oligonucleotide sequence. In some embodiments, the PCR handle 916 is employed for targeted PCR amplification during library preparation that attaches Illumina sequencing adapters to the amplicons. In some embodiments, the PCR handle 916 comprises the sequence of a first universal primer, a complimentary sequence thereof, a partial sequence thereof, or a combination thereof. In some embodiments, the PCR handle 916 can be the same for all or some of binding reagent oligonucleotides 904. In some embodiments, the PCR handle comprises an amplification primer, a complimentary sequence thereof, a partial sequence thereof, or a combination thereof. In some embodiments, the first universal primer comprises a sequencing primer, a complimentary sequence thereof, a partial sequence thereof, or a combination thereof. In some embodiments, the sequencing primer comprises an Illumina sequencing primer. In some embodiments, the sequencing primer comprises a portion of an Illumina sequencing primer. In some embodiments, the sequencing primer comprises a P7 sequencing primer. In some embodiments, the sequencing primer comprises a portion of P7 sequencing primer. In some embodiments, the PCR handle comprises an adapter for Illumina P7. In some embodiments, the PCR handle comprises a partial adapter for Illumina P7. In some embodiments, the amplification primer is an Illumina P7 sequence or a subsequence thereof. In some embodiments, the sequencing primer is an Illumina R2 sequence or a subsequence thereof. In some embodiments, the first universal primer is 5-50 nucleotides in length. In some embodiments, The PCR handle can comprise a nucleic acid sequence of at least 5 nucleotides, for example at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides, including ranges between any two of the listed values, for example 5-50, 5-45, 5-40, 5-35, 5-30, 5-25, 5-20, 5-15, 5-14, 5-13, 5-12, 5-11, 5-10, 5-9, 5-8, 5-7, 5-6, 6-50, 6-45, 6-40, 6-35, 6-30, 6-25, 6-20, 6-15, 6-14, 6-13, 6-12, 6-11, 6-10, 6-9, 6-8, 6-7, 7-50, 7-45, 7-40, 7-35, 7-30, 7-25, 7-20, 7-15, 7-14, 7-13, 7-12, 7-11, 7-10, 7-9, 7-8, 8-50, 8-45, 8-40, 8-35, 8-30, 8-25, 8-20, 8-15, 8-14, 8-13, 8-12, 8-11, 8-10, 8-9, 9-50, 9-45, 9-40, 9-35, 9-30, 9-25, 9-20, 9-15, 9-14, 9-13, 9-12, 9-11, 9-10, 10-50, 10-45, 10-40, 10-35, 10-30, 10-25, 10-20, 10-15, 10-14, 10-13, 10-12, or 10-11 nucleotides. The PCR handle can comprise a nucleic acid sequence of at least 5 nucleotides of the sequence of a first universal primer, an amplification primer, a sequencing primer, a complimentary sequence thereof, a partial sequence thereof, or a combination thereof, for example at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides, including ranges between any two of the listed values, for example 5-50, 5-45, 5-40, 5-35, 5-30, 5-25, 5-20, 5-15, 5-14, 5-13, 5-12, 5-11, 5-10, 5-9, 5-8, 5-7, 5-6, 6-50, 6-45, 6-40, 6-35, 6-30, 6-25, 6-20, 6-15, 6-14, 6-13, 6-12, 6-11, 6-10, 6-9, 6-8, 6-7, 7-50, 7-45, 7-40, 7-35, 7-30, 7-25, 7-20, 7-15, 7-14, 7-13, 7-12, 7-11, 7-10, 7-9, 7-8, 8-50, 8-45, 8-40, 8-35, 8-30, 8-25, 8-20, 8-15, 8-14, 8-13, 8-12, 8-11, 8-10, 8-9, 9-50, 9-45, 9-40, 9-35, 9-30, 9-25, 9-20, 9-15, 9-14, 9-13, 9-12, 9-11, 9-10, 10-50, 10-45, 10-40, 10-35, 10-30, 10-25, 10-20, 10-15, 10-14, 10-13, 10-12, or 10-11 nucleotides of the sequence of a first universal primer, an amplification primer, a sequencing primer, a complimentary sequence thereof, a partial sequence thereof, or a combination thereof.

In some embodiments, the cellular component-binding reagent specific oligonucleotide comprises a sequence complementary to a capture sequence of a barcode configured to capture the sequence of the cellular component-binding reagent specific oligonucleotide. In some embodiments, the barcode comprises a target-binding region which comprises a capture sequence. In some embodiments, the target-binding region comprises a poly(dT) region. In some embodiments, the sequence of the cellular component-binding reagent specific oligonucleotide complementary to the capture sequence comprises a poly(dA) region. In some embodiments, obtaining sequencing information of the plurality of labeled nucleic acids or a portion thereof comprises subjecting the labeled nucleic acids to one or more reactions to generate a set of nucleic acids for nucleic acid sequencing. In some embodiments, each of the barcodes comprises a cell label, a second universal primer, an amplification adaptor, a sequencing adaptor, or a combination thereof. In some embodiments, subjecting the labeled nucleic acids to the one or more reactions comprises subjecting the labeled nucleic acids to an amplification reaction, using the first universal primer, a first primer comprising the sequence of the first universal primer, the second universal primer, a second primer comprising the sequence of the second universal primer, or a combination thereof, to generate the set of nucleic acids for nucleic acid sequencing.

In some embodiments, the detectable moiety is not directly bound to, e.g., covalently or non-covalently directly bound to, the binding reagent oligonucleotide. In these embodiments, the detectable moiety may be part of a component that binds to the binding reagent oligonucleotide, e.g., via non-covalent binding. For example, the detectable label may be part of a label nucleic acid that hybridizes to the binding reagent oligonucleotide, e.g., to the identifier domain of the binding reagent oligonucleotide. In such instances, the label nucleic acid may vary in length, ranging in some instances from 5 to 100 nt in length, and include one or more detectable moieties bound thereto.

Figure 12:
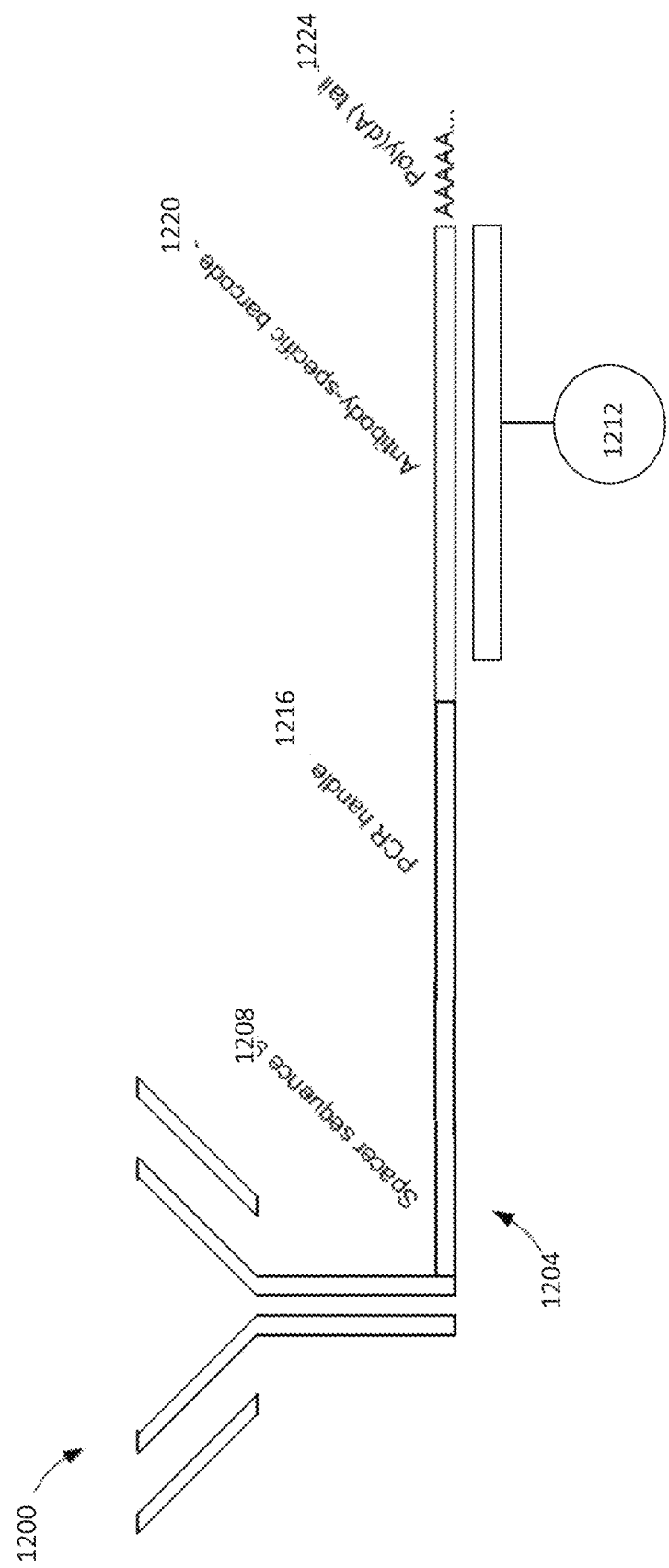
FIG. 12 shows a schematic illustration of a non-limiting exemplary protein binding reagent (an antibody illustrated here) associated with an oligonucleotide that is hybridized to a label nucleic acid comprising a detectable moiety (a fluorophore illustrated here).

FIG. 12 shows a schematic illustration of a non-limiting exemplary binding reagent oligonucleotide 1204 (antibody oligonucleotide illustrated here) that is associated with a binding reagent 1200 (antibody illustrated here). A spacer sequence 1208 (or a linker) can be situated between the binding reagent oligonucleotide 1204 and the binding reagent 1200. The spacer sequence 1208 can be, for example, 1, 2, 3, 4, 5, 6, 7, 8, 9, 10, 11, 12, 13, 14, 15, 16, 17, 18, 19, or 20, or more nucleotides. The binding reagent oligonucleotide 1204 can be an mRNA mimic. The binding reagent oligonucleotide 1204 can comprise a poly(dA) tail 1224. The poly(dA) tail 1224 can enable capture of the binding reagent oligonucleotide 1204. The binding reagent oligonucleotide 1204 can include a unique identifier sequence 1220 (such as an antibody-specific barcode or a sample indexing sequence). The antibody-specific barcode 1220 can be specific to each antibody species. In some embodiments, the antibody barcode 1220 can be the same for all or some of binding reagent oligonucleotides 1204. In some embodiments, the antibody barcode 1220 of different binding reagent oligonucleotides 1204 are different. The binding reagent oligonucleotide 1204 can include a PCR handle 1216 (e.g., a complete or partial Illumina R2 and/or P7 sequence) that can be used for amplification of the oligonucleotide sequence, e.g., as described above. As illustrated, hybridized to the identifier sequence 1220 is a label nucleic acid 1250. The label nucleic acid 1250 can comprise one or more fluorophores 1212 (e.g., a fluorescent moiety, a fluorescent tag), which are thereby associated with the binding reagent oligonucleotide, as the binding reagent oligonucleotide comprises the one or more fluorophores. In some embodiments, the binding reagent oligonucleotide 1204 comprises an alternative detectable moiety other than a fluorophore (e.g., an optical moiety, a luminescent moiety, an electrochemically active moiety, a nanoparticle).

Identifier Sequence

In some embodiments, a unique identifier sequence (e.g., an antibody-specific barcode sequence) is present in a binding reagent oligonucleotide. In some embodiments the unique identifier sequence (e.g., sample indexing sequence, cellular component-binding reagent specific oligonucleotide) is designed to have a Hamming distance greater than 3. In some embodiments, the Hamming distance of the unique identifier sequence can be, or be about, 1, 2, 3, 4, 5, 6, 7, 8, 9, 10, or a number or a range between any two of these values. In some embodiments, the unique identifier sequences has a GC content in the range of 40% to 60% and does not have a predicted secondary structure (e.g., hairpin). In some embodiments, the unique identifier sequence does not comprise any sequences predicted in silico to bind to the mouse and/or human transcripts. In some embodiments, the unique identifier sequence does not comprise any sequences predicted in silico to bind to Rhapsody and/or SCMK system primers. In some embodiments, the unique identifier sequence does not comprise homopolymers.

Alignment Sequence

In some embodiments, the binding reagent oligonucleotide comprises an alignment sequence adjacent to the poly(dA) tail. The alignment sequence can be 1 or more nucleotides in length. The alignment sequence can be 2 nucleotides in length. The alignment sequence can comprise a guanine, a cytosine, a thymine, a uracil, or a combination thereof. The alignment sequence can comprise a poly(dT) region, a poly(dG) region, a poly(dC) region, a poly(dU) region, or a combination thereof. In some embodiments, the alignment sequence is 5' to the poly(dA) region. Advantageously, in some embodiments, the presence of the alignment sequence enables the poly(A) tail of each of the binding reagent oligonucleotides to have the same length, leading to greater uniformity of performance. In some embodiments, the percentage of binding reagent oligonucleotides with an identical poly(dA) region length within a plurality of binding reagent oligonucleotides, each of which comprise an alignment sequence, can be, or be about, 80%, 90%, 91%, 93%, 95%, 97%, 99.9%, 99.9%, 99.99%, or 100%, or a number or a range between any two of these values. In some embodiments, the percentage of binding reagent oligonucleotides with an identical poly(dA) region length within the plurality of binding reagent oligonucleotides, each of which comprise an alignment sequence, can be at least, or be at most, 80%, 90%, 91%, 93%, 95%, 97%, 99.9%, 99.9%, 99.99%, or 100%.

The length of the alignment sequence can be different in different implementations. In some embodiments, the length of the alignment sequence can be, or can be about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a number or a range between any two of these values. In some embodiments, the length of the alignment sequence can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. The number of guanine(s), cytosine(s), thymine(s), or uracil(s) in the alignment sequence can be different in different implementations. The number of guanine(s), cytosine(s), thymine(s), or uracil (s) can be, or can be about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a number or a range between any two of these values. The number of guanine(s), cytosine(s), thymine(s), or uracil(s) can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. In some embodiments, the sample indexing oligonucleotide comprises an alignment sequence. In some embodiments, the cellular component-binding reagent specific oligonucleotide comprises an alignment sequence.

Binding Reagent Oligonucleotide Unique Molecular Label Sequence

In some embodiments, the oligonucleotide associated with a cellular component-binding reagent (e.g., antibody oligonucleotide ("AbOligo" or "AbO"), binding reagent oligonucleotide, cellular component-binding reagent specific oligonucleotides, sample indexing oligonucleotides) comprises a unique molecular label sequence (also referred to as a molecular index (MI), "molecular barcode," or Unique Molecular Identifier (UMI)). In some embodiments, binding reagent oligonucleotide species comprising molecule barcodes as described herein reduce bias by increasing sensitivity, decreasing relative standard error, or increasing sensitivity and/or reducing standard error. The molecule barcode can comprise a unique sequence, so that when multiple sample nucleic acids (which can be the same and/or different from each other) are associated one-to-one with molecule barcodes, different sample nucleic acids can be differentiated from each other by the molecule barcodes. As such, even if a sample comprises two nucleic acids having the same sequence, each of these two nucleic acids can be labeled with a different molecule barcode, so that nucleic acids in the population can be quantified, even after amplification. The molecule barcode can comprise a nucleic acid sequence of at least 5 nucleotides, for example at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides, including ranges between any two of the listed values, for example 5-50, 5-45, 5-40, 5-35, 5-30, 5-25, 5-20, 5-15, 5-14, 5-13, 5-12, 5-11, 5-10, 5-9, 5-8, 5-7, 5-6, 6-50, 6-45, 6-40, 6-35, 6-30, 6-25, 6-20, 6-15, 6-14, 6-13, 6-12, 6-11, 6-10, 6-9, 6-8, 6-7, 7-50, 7-45, 7-40, 7-35, 7-30, 7-25, 7-20, 7-15, 7-14, 7-13, 7-12, 7-11, 7-10, 7-9, 7-8, 8-50, 8-45, 8-40, 8-35, 8-30, 8-25, 8-20, 8-15, 8-14, 8-13, 8-12, 8-11, 8-10, 8-9, 9-50, 9-45, 9-40, 9-35, 9-30, 9-25, 9-20, 9-15, 9-14, 9-13, 9-12, 9-11, 9-10, 10-50, 10-45, 10-40, 10-35, 10-30, 10-25, 10-20, 10-15, 10-14, 10-13, 10-12, or 10-11 nucleotides. In some embodiments, the nucleic acid sequence of the molecule barcode comprises a unique sequence, for example, so that each unique oligonucleotide species in a composition comprises a different molecule barcode. In some embodiments, two or more unique oligonucleotide species can comprise the same molecule barcode, but still differ from each other. For example, if the unique oligonucleotide species include sample barcodes, each unique oligonucleotide species with a particular sample barcode can comprise a different molecule barcode. In some embodiments, a composition comprising unique oligonucleotide species comprises a molecule barcode diversity of at least 1000 different molecule barcodes, and thus at least 1000 unique oligonucleotide species. In some embodiments, a composition comprising unique oligonucleotide species comprises a molecule barcode diversity of at least 6,500 different molecule barcodes, and thus at least 6,500 unique oligonucleotide species. In some embodiments, a composition comprising unique oligonucleotide species comprises a molecule barcode diversity of at least 65,000 different molecule barcodes, and thus at least 65,000 unique oligonucleotide species.

In some embodiments, the unique molecular label sequence is positioned 5' of the unique identifier sequence without any intervening sequences between the unique molecular label sequence and the unique identifier sequence. In some embodiments, the unique molecular label sequence is positioned 5' of a spacer, which is positioned 5' of the unique identifier sequence, so that a spacer is between the unique molecular label sequence and the unique identifier sequence. In some embodiments, the unique identifier sequence is positioned 5' of the unique molecular label sequence without any intervening sequences between the unique identifier sequence and the unique molecular label sequence. In some embodiments, the unique identifier sequence is positioned 5' of a spacer, which is positioned 5' of the unique molecular label sequence, so that a spacer is between the unique identifier sequence and the unique molecular label sequence.

The unique molecular label sequence can comprise a nucleic acid sequence of at least 3 nucleotides, for example at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides, including ranges between any two of the listed values, for example 3-50, 3-45, 3-40, 3-35, 3-30, 3-25, 3-20, 3-15, 3-14, 3-13, 3-12, 3-11, 3-10, 3-9, 3-8, 3-7, 3-6, 3-5, 3-4, 4-50, 4-45, 4-40, 4-35, 4-30, 4-25, 4-20, 4-15, 4-14, 4-13, 4-12, 4-11, 4-10, 4-9, 4-8, 4-7, 4-6, 4-5, 5-50, 5-45, 5-40, 5-35, 5-30, 5-25, 5-20, 5-15, 5-14, 5-13, 5-12, 5-11, 5-10, 5-9, 5-8, 5-7, 5-6, 6-50, 6-45, 6-40, 6-35, 6-30, 6-25, 6-20, 6-15, 6-14, 6-13, 6-12, 6-11, 6-10, 6-9, 6-8, 6-7, 7-50, 7-45, 7-40, 7-35, 7-30, 7-25, 7-20, 7-15, 7-14, 7-13, 7-12, 7-11, 7-10, 7-9, 7-8, 8-50, 8-45, 8-40, 8-35, 8-30, 8-25, 8-20, 8-15, 8-14, 8-13, 8-12, 8-11, 8-10, 8-9, 9-50, 9-45, 9-40, 9-35, 9-30, 9-25, 9-20, 9-15, 9-14, 9-13, 9-12, 9-11, 9-10, 10-50, 10-45, 10-40, 10-35, 10-30, 10-25, 10-20, 10-15, 10-14, 10-13, 10-12, or 10-11 nucleotides. In some embodiments, the unique molecular label sequence is 2-20 nucleotides in length.

In some embodiments, the unique molecular label sequence of the binding reagent oligonucleotide comprises the sequence of at least three repeats of the doublets "VN" and/or "NV" (in which each "V" is any of A, C, or G, and in which "N" is any of A, G, C, or T), for example at least 3, 4, 5, 6, 7, 8, 9, 10, 11, 12, 13, 14, 15, 16, 17, 18, 19, or 20 repeats, including ranges between any two of the listed values. Examples of multiple repeats of the doublet "VN" include VN, VNVN, VNVNVN, and VNVNVNVN. It is noted that while the formulas "VN" and "NV" describe constraints on the base content, not every V or every N has to be the same or different. For example, if the molecule barcodes of unique oligonucleotide species in a composition comprised VNVNVN, one molecule barcode can comprise the sequence ACGGCA, while another molecule barcode can comprise the sequence ATACAT, while another molecule barcode could comprise the sequence ATACAC. It is noted that any number of repeats of the doublet "VN" would have a T content of no more than 50%. In some embodiments, at least 95% of the unique oligonucleotide species of a composition comprising at least 1000 unique oligonucleotide species comprise molecule barcodes comprising at least three repeats of the doublets "VN" and/or "NV," for example at least 3, 4, 5, 6, 7, 8, 9, 10, 11, 12, 13, 14, 15, 16, 17, 18, 19, or 20 repeats, including ranges between any two of the listed values. In some embodiments, at least 99% of the unique oligonucleotide species of a composition comprising at least 1000 unique oligonucleotide species comprise molecule barcodes comprising at least three repeats of the doublets "VN" and/or "NV," for example at least 3, 4, 5, 6, 7, 8, 9, 10, 11, 12, 13, 14, 15, 16, 17, 18, 19, or 20 repeats, including ranges between any two of the listed values. In some embodiments, at least 99.9% of the unique oligonucleotide species of a composition comprising at least 1000 unique oligonucleotide species comprise molecule barcodes comprising at least three repeats of the doublets "VN" and/or "NV," for example at least 3, 4, 5, 6, 7, 8, 9, 10, 11, 12, 13, 14, 15, 16, 17, 18, 19, or 20 repeats, including ranges between any two of the listed values. In some embodiments, at least 95% of the unique oligonucleotide species of a composition comprising at least 6500 unique oligonucleotide species comprise molecule barcodes comprising at least three repeats of the doublets "VN" and/or "NV," for example at least 3, 4, 5, 6, 7, 8, 9, 10, 11, 12, 13, 14, 15, 16, 17, 18, 19, or 20 repeats, including ranges between any two of the listed values. In some embodiments, at least 99% of the unique oligonucleotide species of a composition comprising at least 6500 unique oligonucleotide species comprise molecule barcodes comprising at least three repeats of the doublets "VN" and/or "NV," for example at least 3, 4, 5, 6, 7, 8, 9, 10, 11, 12, 13, 14, 15, 16, 17, 18, 19, or 20 repeats, including ranges between any two of the listed values. In some embodiments, at least 99.9% of the unique oligonucleotide species of a composition comprising at least 6500 unique oligonucleotide species comprise molecule barcodes comprising at least three repeats of the doublets "VN" and/or "NV," for example at least 3, 4, 5, 6, 7, 8, 9, 10, 11, 12, 13, 14, 15, 16, 17, 18, 19, or 20 repeats, including ranges between any two of the listed values. In some embodiments, at least 95% of the unique oligonucleotide species of a composition comprising at least 65,000 unique oligonucleotide species comprise molecule barcodes comprising at least three repeats of the doublets "VN" and/or "NV," for example at least 3, 4, 5, 6, 7, 8, 9, 10, 11, 12, 13, 14, 15, 16, 17, 18, 19, or 20 repeats, including ranges between any two of the listed values. In some embodiments, at least 99% of the unique oligonucleotide species of a of composition comprising at least 65,000 unique oligonucleotide species comprise molecule barcodes comprising at least three repeats of the doublets "VN" and/or "NV," for example at least 3, 4, 5, 6, 7, 8, 9, 10, 11, 12, 13, 14, 15, 16, 17, 18, 19, or 20 repeats, including ranges between any two of the listed values. In some embodiments, at least 99.9% of the unique oligonucleotide species of a composition comprising at least 65,000 unique oligonucleotide species comprise molecule barcodes comprising at least three repeats of the doublets "VN" and/or "NV," for example at least 3, 4, 5, 6, 7, 8, 9, 10, 11, 12, 13, 14, 15, 16, 17, 18, 19, or 20 repeats, including ranges between any two of the listed values. In some embodiments, the composition consists of or consists essentially of at least 1000, 6500, or 65,000 unique oligonucleotide species that each have a molecule barcode comprising the sequence VNVNVN. In some embodiments, the composition consists of or consists essentially of at least 1000, 6500, or 65,000 unique oligonucleotide species that each has a molecule barcode comprising the sequence VNVNVNVN. In some embodiments, at least 95%, 99%, or 99.9% of the barcode regions of the composition as described herein comprise at least three repeats of the doublets "VN" and/or "NV," as described herein. In some embodiments, unique molecular label sequences comprising repeated "doublets "VN" and/or "NV" can yield low bias, while providing a compromise between reducing bias and maintaining a relatively large quantity of available nucleotide sequences, so that relatively high diversity can be obtained in a relatively short sequence, while still minimizing bias. In some embodiments, unique molecular label sequences comprising repeated "doublets "VN" and/or "NV" can reduce bias by increasing sensitivity, decreasing relative standard error, or increasing sensitivity and reducing standard error. In some embodiments, unique molecular label sequences comprising repeated "doublets "VN" and/or "NV" improve informatics analysis by serving as a geomarker. In some embodiments, the repeated doublets "VN" and/or "NV" described herein reduce the incidence of homopolymers within the unique molecular label sequences. In some embodiments, the repeated doublets "VN" and/or "NV" described herein break up homopolymers.

In some embodiments, the sample indexing oligonucleotide comprises a first molecular label sequence. In some embodiments, the first molecular label sequences of at least two sample indexing oligonucleotides are different, and the sample indexing sequences of the at least two sample indexing oligonucleotides are identical. In some embodiments, the first molecular label sequences of at least two sample indexing oligonucleotides are different, and the sample indexing sequences of the at least two sample indexing oligonucleotides are different. In some embodiments, the cellular component-binding reagent specific oligonucleotide comprises a second molecular label sequence. In some embodiments, the second molecular label sequences of at least two cellular component-binding reagent specific oligonucleotides are different, and the unique identifier sequences of the at least two cellular component-binding reagent specific oligonucleotides are identical. In some embodiments, the second molecular label sequences of at least two cellular component-binding reagent specific oligonucleotides are different, and the unique identifier sequences of the at least two cellular component-binding reagent specific oligonucleotides are different. In some embodiments, the number of unique second molecular label sequences associated with the unique identifier sequence for the cellular component-binding reagent capable of specifically binding to the at least one cellular component target in the sequencing data indicates the number of copies of the at least one cellular component target in the one or more of the plurality of cells. In some embodiment, a combination (e.g., minimum, average, and maximum) of (1) the number of unique first molecular label sequences associated with the unique identifier sequence for the cellular component-binding reagent capable of specifically binding to the at least one cellular component target in the sequencing data and (2) the number of unique second molecular label sequences associated with the unique identifier sequence for the cellular component-binding reagent capable of specifically binding to the at least one cellular component target in the sequencing data indicates the number of copies of the at least one cellular component target in the one or more of the plurality of cells.

In some embodiments, the barcoded binding reagent oligonucleotides disclosed herein comprises two unique molecular label sequences: a molecular label sequence derived from the barcode and a molecular label sequence derived from a binding reagent oligonucleotide (e.g., the first molecular label sequence of a sample indexing oligonucleotide, the second molecular label sequence of a cellular component-binding reagent specific oligonucleotide). As used herein, "dual molecular indexing" refers to methods and compositions disclosed herein employing barcoded binding reagent oligonucleotides (or products thereof) that comprise a first unique molecular label sequence and second unique molecular label sequence (or complementary sequences thereof). In some embodiments, the methods of sample identification and of quantitative analysis of cellular component targets disclosed herein can comprise obtaining the sequence of information of the barcode molecular label sequence and/or the binding reagent oligonucleotide molecular label sequence. In some embodiments, the number of barcode molecular label sequences associated with the unique identifier sequence for the cellular component-binding reagent capable of specifically binding to the at least one cellular component target in the sequencing data indicates the number of copies of the at least one cellular component target in the one or more of the plurality of cells. In some embodiments, the number of binding reagent oligonucleotide molecular label sequences associated with the unique identifier sequence for the cellular component-binding reagent capable of specifically binding to the at least one cellular component target in the sequencing data indicates the number of copies of the at least one cellular component target in the one or more of the plurality of cells. In some embodiments, the number of both the binding reagent oligonucleotide molecular label sequences and barcode molecular label sequences associated with the unique identifier sequence for the cellular component-binding reagent capable of specifically binding to the at least one cellular component target in the sequencing data indicates the number of copies of the at least one cellular component target in the one or more of the plurality of cells.

Optical Barcode

In some embodiments, each cellular component-binding reagent specific oligonucleotide is associated with an optical barcode comprising one or more detectable moieties (such as 2, 3, 4, 5, 6, 7, 8, 9, 10, 20, 30, 40, 50, 60, 70, 80, 90, 100, or more). In some embodiments, each cellular component-binding reagent specific oligonucleotide is associated with an optical barcode comprising the first detectable moiety and second detectable moiety. In some embodiments, cellular component-binding reagents specifically binding the same cellular component target are associated with cellular component-binding reagent specific oligonucleotides with identical optical barcodes. In some embodiments, cellular component-binding reagents specifically binding the different cellular component targets are associated with cellular component-binding reagent specific oligonucleotides with different optical barcodes.

In some embodiments the binding reagent oligonucleotide comprises three or more detectable moieties. In some embodiments each of the detectable moieties are spectrally distinct. In some embodiments, each of a plurality of binding reagent oligonucleotides has a unique optical barcode. For example, the plurality of binding reagent oligonucleotides can include, include about, or include more than 1, 2, 3, 4, 5, 6, 7, 8, 9, 10, 100, 200, 300, 400, 500, 600, 700, 800, 900, $10^3$, $10^4$, $10^5$, $10^6$, $10^7$, $10^8$, $10^9$, $10^{10}$, $10^{11}$, $10^{12}$, or a number or a range between any two of these values, binding reagent oligonucleotides each with a unique optical barcode.

The cellular component binding reagent (e.g., a protein binding reagent) can be associated with two or more binding reagent oligonucleotides (e.g., cellular component-binding reagent specific oligonucleotides) with an identical detectable moiety (e.g., identical optical barcode). The cellular component binding reagent can be associated with two or more binding reagent oligonucleotides with different detectable moieties (e.g., different optical barcodes). The number of binding reagent oligonucleotides associated with the cellular component binding reagent can be different in different implementations. In some embodiments, the number of binding reagent oligonucleotides, whether having an identical optical barcodes (or moieties), or different optical barcodes (or moieties), can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values. In some embodiments, the number of binding reagent oligonucleotides with distinct optical barcodes (or moieties) can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, or 1000.

Association of Oligonucleotide with Cellular Component Binding Reagent

The binding reagent oligonucleotide can be associated with the cellular component binding reagent through various mechanisms. The binding reagent oligonucleotide can be conjugated with the cellular component binding reagent through various mechanisms. In some embodiments, the binding reagent oligonucleotide can be conjugated with the cellular component binding reagent covalently. In some embodiments, the binding reagent oligonucleotide can be conjugated with the cellular component binding reagent non-covalently. In some embodiments, the cellular component-binding reagent specific oligonucleotide is associated with the cellular component-binding reagent through a linker. In some embodiments, the binding reagent oligonucleotide is conjugated with the cellular component binding reagent through a linker. In some embodiments, the binding reagent oligonucleotide can comprise a linker. The linker can comprise a chemical group. The chemical group can be reversibly, or irreversibly, attached to the molecule of the cellular component binding reagent. The chemical group can be selected from the group consisting of a UV photo-cleavable group, a disulfide bond, a streptavidin, a biotin, an amine, and any combination thereof. The linker can comprise a carbon chain. The carbon chain can comprise, for example, 5-50 carbon atoms. The carbon chain can have different numbers of carbon atoms in different embodiments. In some embodiments, the number of carbon atoms in the carbon chain can be, or can be about, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or a number or a range between any two of these values. In some embodiments, the number of carbon atoms in the carbon chain can be at least, or can be at most, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, the carbon chain comprises 2-30 carbons. In some embodiments, the carbon chain comprises 12 carbons. In some embodiments, amino modifiers employed for binding reagent oligonucleotide can be conjugated to the cellular component binding reagent. In some embodiments, the linker comprises 5' amino modifier C6 (5AmMC6). In some embodiments, the linker comprises 5' amino modifier C12 (5AmMC12). In some embodiments, the linker comprises a derivative of 5AmMC12. In some embodiments, a longer linker achieves a higher efficiency of conjugation. In some embodiments, a longer linker achieves a higher efficiency of modification prior to conjugation. In some embodiments, increasing the distance between the functional amine and the DNA sequence yields a higher efficiency of conjugation. In some embodiments, increasing the distance between the functional amine and the DNA sequence yields a higher efficiency of modification prior to conjugation. In some embodiments, the use of 5AmMC12 as a linker yields a higher efficiency of modification (prior to conjugation) than the use of 5AmMC6 as a linker. In some embodiments the use of 5AmMC12 as a linker yields a higher efficiency of conjugation than the use of 5AmMC6 as a linker. In some embodiments, the binding reagent oligonucleotide comprises a spacer sequence and/or a linker.

In some embodiments, the cellular component-binding reagent specific oligonucleotide is non-covalently attached to the cellular component-binding reagent. In some embodiments, the cellular component-binding reagent specific oligonucleotide is configured to be detachable from the cellular component-binding reagent. In some embodiments, the binding reagent oligonucleotide can be detached from the binding reagent using chemical, optical or other means. In some embodiments, the methods comprise dissociating the cellular component-binding reagent specific oligonucleotide from the cellular component-binding reagent. In some embodiments, dissociating the cellular component-binding reagent specific oligonucleotide comprises detaching the cellular component-binding reagent specific oligonucleotide from the cellular component-binding reagent by UV photocleaving, chemical treatment, heating, enzyme treatment, or any combination thereof. In some embodiments, the dissociating occurs after barcoding the cellular component-binding reagent specific oligonucleotide. In some embodiments, the dissociating occurs before barcoding the cellular component-binding reagent specific oligonucleotide. In some embodiments, the cellular component-binding reagent specific oligonucleotide is configured to be non-detachable from the cellular component-binding reagent.

Cellular Component Binding Reagent Types

The compositions comprising cellular component binding reagents can comprise one or more additional cellular component binding reagents that (a) are not conjugated with a binding reagent oligonucleotide, which is also referred to herein as the binding reagent oligonucleotide-free cellular component binding reagent, and/or (b) are conjugated with a binding reagent oligonucleotide that does not comprise a detectable moiety. The number of additional cellular component binding reagents in the plurality of compositions can be different in different implementations. In some embodiments, the number of additional cellular component binding reagents can be, or be about, 1, 2, 3, 4, 5, 6, 7, 8, 9, 10, 20, 30, 40, 50, 60, 70, 80, 90, 100, or a number or a range between any two of these values. In some embodiments, the number of additional cellular component binding reagents can be at least, or be at most, 1, 2, 3, 4, 5, 6, 7, 8, 9, 10, 20, 30, 40, 50, 60, 70, 80, 90, or 100. The cellular component binding reagent and any of the additional cellular component binding reagents can be identical, in some embodiments. The plurality of compositions comprising cellular component binding reagents can comprise (a) cellular component binding reagents conjugated with a binding reagent oligonucleotide comprising a detectable moiety and (b) cellular component binding reagents conjugated with a binding reagent oligonucleotide not comprising a detectable moiety. The plurality of compositions comprising cellular component binding reagents can comprise (a) cellular component binding reagents conjugated with a binding reagent oligonucleotide comprising a detectable moiety and (b) cellular component binding reagents not conjugated with a binding reagent oligonucleotide. The plurality of compositions comprising cellular component binding reagents can comprise (a) cellular component binding reagents conjugated with a binding reagent oligonucleotide comprising a detectable moiety, (b) cellular component binding reagents not conjugated with a binding reagent oligonucleotide, and (c) cellular component binding reagents conjugated with a binding reagent oligonucleotide not comprising a detectable moiety.

In some embodiments, a mixture comprising cellular component binding reagent(s) that is conjugated with one or more binding reagent oligonucleotides comprising a detectable moiety and cellular component binding reagent(s) that is conjugated with binding reagent oligonucleotides not comprising a detectable moiety is provided. The mixture can be used in some embodiments of the methods disclosed herein, for example, to contact the sample(s) and/or cell(s). The ratio of (1) the number of a cellular component binding reagent conjugated with a binding reagent oligonucleotide comprising a detectable moiety and (2) the number of another cellular component binding reagent (e.g., the same cellular component binding reagent) conjugated with a binding reagent oligonucleotide not comprising a detectable moiety in the mixture can be different in different implementations. In some embodiments, the ratio can be, or be about, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, 1:10000, or a number or a range between any two of the values. In some embodiments, the ratio can be at least, or be at most, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, or 1:10000.

In some embodiments, the ratio can be, or be about, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values. In some embodiments, the ratio can be at least, or be at most, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1.

A cellular component binding reagent can be conjugated with a binding reagent oligonucleotide comprising a detectable moiety or can be conjugated with a binding reagent oligonucleotide not comprising a detectable moiety. In some embodiments, the percentage of the cellular component binding reagent conjugated with a binding reagent oligonucleotide comprising a detectable moiety in a mixture comprising the cellular component binding reagent that is conjugated with the binding reagent oligonucleotide comprising a detectable moiety and the cellular component binding reagent(s) that is conjugated with the binding reagent oligonucleotide not comprising a detectable moiety can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of the cellular component binding reagent conjugated with an oligonucleotide comprising a detectable moiety in a mixture can be at least, or be at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

Cellular Component Cocktails

In some embodiments, a cocktail of cellular component-binding reagents (e.g., an antibody cocktail) can be used to increase labeling sensitivity in the methods disclosed herein. Without being bound by any particular theory, it is believed that this may be because cellular component expression or protein expression can vary between cell types and cell states, making finding a universal cellular component binding reagent or antibody that labels all cell types challenging. For example, cocktail of cellular component binding reagents can be used to allow for more sensitive and efficient labeling of more sample types. The cocktail of cellular component binding reagents can include two or more different types of cellular component binding reagents, for example a wider range of cellular component binding reagents or antibodies. Cellular component binding reagents that label different cellular component targets can be pooled together to create a cocktail that sufficiently labels all cell types, or one or more cell types of interest.

In some embodiments, each of the plurality of compositions (e.g., sample indexing compositions) comprises a cellular component binding reagent. In some embodiments, a composition of the plurality of compositions comprises two or more cellular component binding reagents, wherein each of the two or more cellular component binding reagents is associated with a binding reagent oligonucleotide (e.g., a sample indexing oligonucleotide), wherein at least one of the two or more cellular component binding reagents is capable of specifically binding to at least one of the one or more cellular component targets. The sequences of the binding reagent oligonucleotides associated with the two or more cellular component binding reagents can be identical. The sequences of the binding reagent oligonucleotides associated with the two or more cellular component binding reagents can comprise different sequences. Each of the plurality of compositions can comprise the two or more cellular component binding reagents.

The number of different types of cellular component binding reagents (e.g., a CD147 antibody and a CD47 antibody) in a composition can be different in different implementations. A composition with two or more different types of cellular component binding reagents can be referred to herein as a cellular component binding reagent cocktail (e.g., a sample indexing composition cocktail). The number of different types of cellular component binding reagents in a cocktail can vary. In some embodiments, the number of different types of cellular component binding reagents in cocktail can be, or be about 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or a number or a range between any two of these values. In some embodiments, the number of different types of cellular component binding reagents in cocktail can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, or 100000. The different types of cellular component binding reagents can be conjugated to binding reagent oligonucleotides with the same or different sequences (e.g., sample indexing sequences).

Some or all of the cellular component binding reagents of a cocktail can each comprise an oligonucleotide (e.g., a sample indexing oligonucleotide) with a detectable moiety. Different cellular component binding reagents of a cocktail can comprise oligonucleotides with different detectable moieties (or detectable moieties that are spectrally distinct). The different detectable moieties can be used for cell sorting (or other methods disclosed herein). The oligonucleotide sequences can be used for sample indexing.

Association of Barcodes

The oligonucleotides associated with the cellular component binding reagents (e.g., antigen binding reagents or protein binding reagents) and/or the nucleic acid molecules may randomly associate with the oligonucleotide probes (e.g., barcodes, such as stochastic barcodes). The oligonucleotides associated with the cellular component binding reagents, referred to herein as binding reagent oligonucleotides, can be, or comprise oligonucleotides of the disclosure, such as an antibody oligonucleotide, a sample indexing oligonucleotide, a cell identification oligonucleotide, a control particle oligonucleotide, a control oligonucleotide, an interaction determination oligonucleotide, etc. Association can, for example, comprise hybridization of an oligonucleotide probe's target binding region to a complementary portion of the target nucleic acid molecule and/or the oligonucleotides of the protein binding reagents. For example, a oligo(dT) region of a barcode (e.g., a stochastic barcode) can interact with a poly(A) tail of a target nucleic acid molecule and/or a poly(A) tail of an oligonucleotide of a protein binding reagent. The assay conditions used for hybridization (e.g., buffer pH, ionic strength, temperature, etc.) can be chosen to promote formation of specific, stable hybrids.

The disclosure provides for methods of associating a molecular label with a target nucleic acid and/or an oligonucleotide associated with a cellular component binding reagent using reverse transcription. As a reverse transcriptase can use both RNA and DNA as template. For example, the oligonucleotide originally conjugated on the cellular component binding reagent can be either RNA or DNA bases, or both. A binding reagent oligonucleotide can be copied and linked (e.g., covalently linked) to a cell label and a barcode sequence (e.g., a molecular label) in addition to the sequence, or a portion thereof, of the binding reagent sequence. As another example, an mRNA molecule can be copied and linked (e.g., covalently linked) to a cell label and a barcode sequence (e.g., a molecular label) in addition to the sequence of the mRNA molecule, or a portion thereof.

In some embodiments, molecular labels can be added by ligation of an oligonucleotide probe target binding region and a portion of the target nucleic acid molecule and/or the oligonucleotides associated with (e.g., currently, or previously, associated with) with cellular component binding reagents. For example, the target binding region may comprise a nucleic acid sequence that can be capable of specific hybridization to a restriction site overhang (e.g., an EcoRI sticky-end overhang). The methods can further comprise treating the target nucleic acids and/or the oligonucleotides associated with cellular component binding reagents with a restriction enzyme (e.g., EcoRI) to create a restriction site overhang. A ligase (e.g., T4 DNA ligase) may be used to join the two fragments.

Determining the Number or Presence of Unique Molecular Label Sequences

In some embodiments, the methods disclosed herein comprise determining the number or presence of unique molecular label sequences for each unique identifier, each nucleic acid target molecule, and/or each binding reagent oligonucleotides (e.g., antibody oligonucleotides). For example, the sequencing reads can be used to determine the number of unique molecular label sequences for each unique identifier, each nucleic acid target molecule, and/or each binding reagent oligonucleotide. As another example, the sequencing reads can be used to determine the presence or absence of a molecular label sequence (such as a molecular label sequence associated with a target, a binding reagent oligonucleotide, an antibody oligonucleotide, a sample indexing oligonucleotide, a cell identification oligonucleotide, a control particle oligonucleotide, a control oligonucleotide, an interaction determination oligonucleotide, etc. in the sequencing reads).

In some embodiments, the number of unique molecular label sequences for each unique identifier, each nucleic acid target molecule, and/or each binding reagent oligonucleotide indicates the quantity of each cellular component target (e.g., an antigen target or a protein target) and/or each nucleic acid target molecule in the sample. In some embodiments, the quantity of a cellular component target and the quantity of its corresponding nucleic acid target molecules, e.g., mRNA molecules, can be compared to each other. In some embodiments, the ratio of the quantity of a cellular component target and the quantity of its corresponding nucleic acid target molecules, e.g., mRNA molecules, can be calculated. The cellular component targets can be, for example, cell surface protein markers. In some embodiments, the ratio between the protein level of a cell surface protein marker and the level of the mRNA of the cell surface protein marker is low.

The methods disclosed herein can be used for a variety of applications. For example, the methods disclosed herein can be used for proteome and/or transcriptome analysis of a sample. In some embodiments, the methods disclosed herein can be used to identify a cellular component target and/or a nucleic acid target, i.e., a biomarker, in a sample. In some embodiments, the cellular component target and the nucleic acid target correspond to each other, i.e., the nucleic acid target encodes the cellular component target. In some embodiments, the methods disclosed herein can be used to identify cellular component targets that have a desired ratio between the quantity of the cellular component target and the quantity of its corresponding nucleic acid target molecule in a sample, e.g., mRNA molecule. In some embodiments, the ratio is, or is about, 0.001, 0.01, 0.1, 1, 10, 100, 1000, or a number or a range between any two of the above values. In some embodiments, the ratio is at least, or is at most, 0.001, 0.01, 0.1, 1, 10, 100, or 1000. In some embodiments, the methods disclosed herein can be used to identify cellular component targets in a sample that the quantity of its corresponding nucleic acid target molecule in the sample is, or is about, 1000, 100, 10, 5, 2 1, 0, or a number or a range between any two of these values. In some embodiments, the methods disclosed herein can be used to identify cellular component targets in a sample that the quantity of its corresponding nucleic acid target molecule in the sample is more than, or less than, 1000, 100, 10, 5, 2 1, or 0.

Flow Cytometry

In some embodiments, the method comprises isolating, obtaining, and/or enriching cells of interest. Isolating, obtaining, and/or enriching cells of interest has been described in U.S. Patent Application Publication No. 2016/0244828, the content of which is incorporated herein by reference in its entirety. For example, the method comprises isolating, obtaining, and/or enriching cells of interest can be performed with a flow cytometer or flow cytometrically. In some embodiments, the flow cytometer utilizes fluorescence-activated cell sorting.

Flow cytometry is a valuable method for the analysis and isolation of cells. As such it has a wide range of diagnostic and therapeutic applications. Flow cytometry utilizes a fluid stream to linearly segregate cells such that they can pass, single file, through a detection apparatus. Individual cells can be distinguished according to their location in the fluid stream and the presence of detectable markers or moieties (such as fluorophores on oligonucleotides associated with cellular component binding reagents). Cells flow through the focused interrogation point where at least one laser directs a laser beam to a focused point within the channel. The sample fluid containing cells is hydrodynamically focused to a very small core diameter by flowing sheath fluid around the sample stream at a very high volumetric rate. The small core diameter can be fewer than 10, 20, 30, 40, 50, 60, 70, 80, 90, 100, 110, 120, 130, 140, 150, 160, 170, 180, 190, 200 micrometers, or a number or a range between any two of these values. The volumetric rate of the sheath fluid can be on the order of at least 10, 20, 30, 40, 50, 60, 70, 80, 90, 100, 200, 300, 400, 500, 600, 700, 800, 900, or 1000 times, or a number or a range between any two of these values, the volumetric rate of the sample. This results in very fast linear velocities for the focused cells on the order of meters per second. So each cell spends a very limited time in the excitation spot, for example fewer than 1, 2, 3, 4, 5, 6, 7, 8, 9, 10, 20, 30, 40, 50, 60, 70, 80, 90, 100 microseconds, or a number or a range between any two of these values. Once the cells pass the interrogation point the cells cannot be redirected to the interrogation point again because the linear flow velocity cannot be reversed.

Flow cytometers are analytical tools that enable the characterization of cells on the basis of optical parameters such as light scatter and fluorescence. In a flow cytometer, cells in a fluid suspension are passed by a detection region in which the cells are exposed to an excitation light, typically from one or more lasers, and the light scattering and fluorescence properties of the cells are measured. Cells or components thereof typically are labeled with fluorescent dyes to facilitate detection. A multiplicity of different cells or components can be simultaneously detected by using spectrally distinct fluorescent dyes to label the different cells or components. In some implementations, a multiplicity of photodetectors, one for each of the scatter parameters to be measured, and one for each of the distinct dyes to be detected are included in the analyzer. The data obtained comprise the signals measured for each of the light scatter parameters and the fluorescence emissions.

Isolation of biological cells has been achieved by adding a sorting or collection capability to flow cytometers. Cells in a segregated stream, detected as having one or more desired characteristics, are individually isolated from the sample stream by mechanical or electrical removal. This method of flow sorting has been used to sort cells of different types, to separate sperms bearing X and Y chromosomes for breeding, to sort chromosomes for genetic analysis, and to isolate particular organisms from complex biological populations.

A common flow sorting technique utilizes drop sorting in which a fluid stream containing linearly segregated cells is broken into drops and the drops containing cells of interest are electrically charged and deflected into a collection tube by passage through an electric field. Drop sorting systems are capable of forming drops at a rate of about 100, 500, 1000, 2000, 3000, 4000, 5000, 6000, 7500, 10000, 20000, 30000, 40000, 50000, 60000, 75000, 100000, 200000, 300000, 400000, 500000, 600000, 750000, 1000000 drops/second, or a number or a range between any two of these values, in a fluid stream that is passed through a nozzle having a diameter less than 1000, 750, 600, 500, 400, 300, 200, 100, 75, 60, 50, 40, 30, 20, 10, 5, 2, 1 micrometers, or a number or a range between any two of these values. Drop sorting requires that the drops break off from the stream at a fixed distance from the nozzle tip. The distance is normally on the order of a few millimeters from the nozzle tip and can be maintained for an unperturbed fluid stream by oscillating the nozzle tip at a predefined frequency.

The linearly segregated cells in the stream can be characterized as they pass through an observation point situated just below the nozzle tip. Once a cell is identified as meeting about 1, 2, 3, 4, 5, 6, 7, 8, 9, 10, 20, 30, 40, 50, 60, 75, 100, 200, 300, 400, 500, 600, 750 criteria, or a number or a range between any two of these values, or more than 1000 criteria, the time at which it will reach the drop break-off point and break from the stream in a drop can be predicted. Possibly, a brief charge is applied to the fluid stream just before the drop containing the selected cell breaks from the stream and then grounded immediately after the drop breaks off. The drop to be sorted maintains an electrical charge as it breaks off from the fluid stream, and all other drops are left uncharged. The charged drop is deflected sideways from the downward trajectory of the other drops by an electrical field and collected in a sample tube. The uncharged drops fall directly into a drain.

Cytometers can further comprise means for recording the measured data and analyzing the data. For example, data storage and analysis can be carried out using a computer connected to the detection electronics. For example, the data can be stored in tabular form, where each row corresponds to data for one cell, and the columns correspond to each of the measured parameters. The use of standard file formats, such as an "FCS" file format, for storing data from a flow cytometer facilitates analyzing data using separate programs and/or machines. Using current analysis methods, the data typically are displayed in 2-dimensional ("2D") plots for ease of visualization, but other methods can be used to visualize multidimensional data.

The parameters measured using a flow cytometer typically include the excitation light that is scattered by the cell along a mostly forward direction, referred to as forward scatter ("FSC"), the excitation light that is scattered by the cell in a mostly sideways direction, referred to as side scatter ("SSC"), and the light emitted from fluorescent molecules in one or more channels (range of frequencies) of the spectrum, referred to as FL1, FL2, etc., or by the fluorescent dye that is primarily detected in that channel. Different cell types can be identified by the scatter parameters and the fluorescence emissions resulting from labeling various cell proteins with dye-labeled antibodies.

Fluorescence-activated cell sorting or is a specialized type of flow cytometry. It provides a method for sorting a heterogeneous mixture of cells into two or more containers or wells of a microtiter plate, one cell at a time, based upon the specific light scattering and fluorescent characteristics of each cell. It records fluorescent signals from individual cells, and physically separates cells of particular interest. The acronym FACS is trademarked and owned by Becton Dickinson.

The cell suspension is placed near the center of a narrow, rapidly flowing stream of liquid. The flow is arranged so that on the average (Poisson distribution) there is a large separation between cells relative to their diameter. A vibrating mechanism causes the stream of cells to break into individual droplets. The system is adjusted so that there is a low probability of more than one cell being in a droplet. Just before the stream breaks into droplets the flow passes through one or more laser intersects where the fluorescent character of interest of each cell is measured. If a cell is to be collected, a charge is applied to the flow cell during the period of time one or more drops form and break off from the stream. These charged droplets then fall through an electrostatic deflection system that diverts droplets into target containers based upon the charge applied to the droplet.

Figure 8:
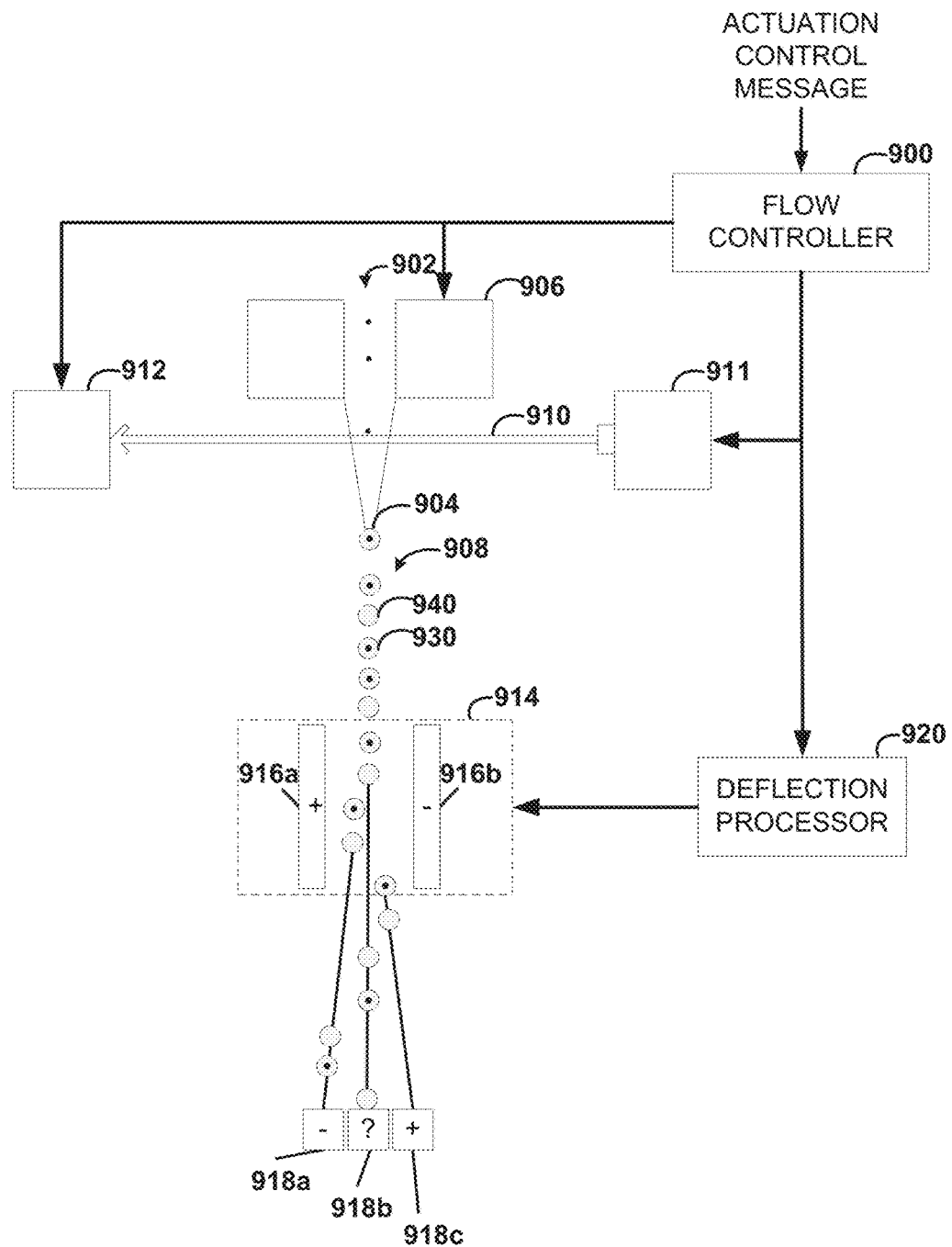
FIG. 8 is a non-limiting schematic illustration of a cell sorter system.

FIG. 8 shows a functional block diagram for one example of a sorting device, for example a flow cytometer, suitable to use for cell sorting. The sorting device illustrated in FIG. 8 can be referred to as stream-in-air sorting system. Cells in sample stream 802 are shown. The sample stream 802 passes through an orifice 804 of a nozzle 806. The sample stream 802, upon exiting the nozzle 806 forms a jet 808. A laser beam 810 is generated by a laser 811 to illuminate the cells that can be included in the jet 808. The light is detected by a detection station 812 to generate multiple signals that are processed to generate a multi-parameter event data point. The generated event data can be provided to a sample behavior analyzer. The providing can be direct, via communication intermediaries (e.g., network/cloud), via memory, or a hybrid configuration.

Based on the values of the multiple signals, prior to droplets leaving jet 808, they are positively charged, negatively charged, or left neutral. Some droplets will include a cell of the sample as shown by a droplet 830 while other droplets will not include a cell of the sample as shown by a droplet 840. Droplets pass through a deflection field 814. The deflection field 814 includes two oppositely charged deflection plates 816a and 816b. The deflection plates 816a and 816b are configured to steer charged droplets in the jet 808 to their respective collection vessels 818a, 818b, or 818c. As shown, vessel 818b collects negatively charged droplets because the positive deflection plate 816a will attract negatively charged droplets. Similarly, vessel 818c will collect positively charged droplets because the negatively charged deflection plate 816b will attract positively charged droplets. Each collection vessel can be a microtiter plate or a well of a microtiter plate.

In one collection scheme, the flow system identifies all cells of interest as they pass the detection station 812 based on the values of their signals, and then causes jet 808 to be charged or neutral at the instant the cell of interest leaves jet 808 as a droplet. In this way, cells of interest are caused to have the same charge. This allows collection of the cells in the same collection vessel, including the same or different wells of a multitier plate.

Non-limiting examples of the sorting device illustrated in FIG. 8 suitable to use for cell sorting include a BD FACSJazz™ cell sorter, a BD FACSseq™ cell sorter, or any other cell sorters including a Bio-Rad Laboratories, Inc. (Hercules, CA) S3e™ Cell Sorter, a Sony Biotechnology Inc. (San Jose, CA) SH800 cell sorter, a Beckman Coulter Inc. (Brea, CA) MoFlo™ XDP cell sorter.

In some embodiments, the methods utilize the tagging and staining of cell surface markers for cell sorting. In some embodiments, the methods utilize the tagging of cell surface markers for magnetic depletion of cells not of interest, interfering cells, and debris. In some embodiments, the methods include one or more of determining genotype of the patient based on the obtained sequence information; determining phenotype of the patient based on the obtained sequence information; determining one or more genetic mutation of the patient based on the sequence information; and predicting susceptibility of a patient to one or more diseases. At least one of the one or more diseases is cancer or a hereditary disease.

FACS can sort cells based on the tagging and staining of cell surface markers using antibodies that target detectable cell markers. The antibodies include monoclonal and polyclonal antibodies that are coupled to fluorophores. Detectable cell markers include cell surface markers on cells of interest. In some embodiments, magnetic depletion can be based on the tagging of cell surface markers with magnetic beads with antibodies, including monoclonal antibodies and polyclonal antibodies, conjugated to their surfaces targeting cells not of interest, interfering cells, and/or debris. Non-limiting examples of cells surface markers include CD surface markers, growth factor/cytokine, chemokine receptors, nuclear receptors, and other receptors. Examples of cell surface markers include, but are not limited to, ALCAM; CD166; ASGR1; BCAM; BSG; CD147; CD14; CD19; CD2; CD200; CD127 BV421; CD25 BB515; CD161 PE; CD45RA PerCP-Cy™5.5; CD15S AF647; CD4 APC-H; CD4; CD25; CD127; CD45RA; CD15S; CD161; CD3; EpCAM; CD44; and Her2/Neu. Examples of growth factors/cytokines, chemokine receptors include ACVR 1B; ALK4; ACVR2A; ACVR2B; BMPR1A; BMPR2; CSF1R; MCSFR; CSF2RB; EGFR; EPHA2; EPHA4; EPHB2; EPHB4; and ERBB2. Examples of nuclear receptors include androgen receptor; CAR; ER Alpha; ER Beta; ESRRA; ESRRB; ESRRG; FXR; Glucocorticoid Receptor; LXR-a; LXR-b; PPARA; PPARD; PPARG; PXR; SXR; Estrogen Receptor Beta; Progesterone Receptor; RARA; RARB; RARG; RORA; RXRA; RXRB; THRA; THRB; and Vitamin D3 Receptor. Examples of other receptors include AGER; APP; CLEC12A; MICL; CTLA4; FOLR1; FZD1; FRIZZLED-1; KLRB1A; LRPAP1; NCR3; NKP30; OLR1; PROCR; PTPN1; SOX9; SCARB2; TACSTD2; TREM1; TREM2; TREML1; and VDR.

Partitioning

In some embodiments, partitioning the plurality of cells comprises partitioning the plurality of cells associated with the plurality of cellular component-binding reagents and a plurality of barcoding particles comprising the barcoding particle to the plurality of partitions, wherein the partition of the plurality of partitions comprises the single cell from the plurality of cells associated with the cellular component-binding reagent and the barcoding particle. In some embodiments, the methods comprise prior to extending barcodes: partitioning the cells of plurality of cells associated with cellular component-binding reagents to a plurality of partitions, wherein a partition of the plurality of partitions comprises a single cell from the cells associated with the cellular component-binding reagents; in the partition comprising the single cell, contacting a barcoding particle with the cellular component-binding reagent specific oligonucleotides, wherein the barcoding particle comprises the plurality of barcodes, and wherein two barcodes of the plurality of barcodes comprise different molecular label sequences. The partition provide for a single cell composition, and may be defined in a number of different ways, such as a microwell, a droplet, etc. In some embodiments, at least one barcode of the plurality of barcodes is immobilized on the particle, partially immobilized on the particle, enclosed in the particle, partially enclosed in the particle, or a combination thereof. In some embodiments, the barcoding particle is disruptable. In some embodiments, the particle comprises a bead. In some embodiments, the barcoding particle is a solid bead, a semi-permeable bead, a hydrogel bead, or a combination thereof. In some embodiments, the partition is a well or a droplet.

Next Generation Sequencing

In certain embodiments, the methods provided further include subjecting a prepared expression library to an NGS protocol. The protocol may be carried out on any suitable NGS sequencing platform. NGS sequencing platforms of interest include, but are not limited to, a sequencing platform provided by Illumina® (e.g., the HiSeq™, MiSeq™ and/or NextSeq™ sequencing systems); Ion Torrent™ (e.g., the Ion PGM™ and/or Ion Proton™ sequencing systems); Pacific Biosciences (e.g., the PACBIO RS II Sequel sequencing system); Life Technologies™ (e.g., a SOLiD sequencing system); Oxford Nanopore (e.g., Minion), Roche (e.g., the 454 GS FLX+ and/or GS Junior sequencing systems); or any other sequencing platform of interest. The NGS protocol will vary depending on the particular NGS sequencing system employed. Detailed protocols for sequencing, e.g., which may include further amplification (e.g., solid-phase amplification), sequencing the amplicons, and analyzing the sequencing data are available from the manufacturer of the NGS sequencing system employed.

Cell Membrane Permeability

In some embodiments, at least one of the plurality of cellular component-binding reagents comprises a cell membrane-permeable cellular component-binding reagent, wherein contacting the plurality of cellular component-binding reagents with the plurality of cells comprises contacting the cell membrane-permeable cellular component-binding reagent with the plurality of cells, whereby the cell membrane-permeable cellular component-binding reagent is internalized into the cells of the plurality of cells. Cell membrane-permeable cellular component-binding reagents (such as barcoded antibodies) and their uses (such as sample indexing of cells) have been described in U.S. Provisional Patent Application 62/723,958, the content of which is incorporated herein by reference in its entirety.

In some embodiments, the cell membrane-permeable cellular component-binding reagent is internalized into the cells. The cell membrane-permeable cellular component-binding reagent can be internalized into the cells by diffusion through the cell membranes of the cells. The method can comprise permeabilizing cell membranes of the cells. Permeabilizing the cell membranes of the cells can comprise permeabilizing the cell membranes of the cells using a detergent. The cell membrane-permeable reagent can be internalized into the cells via one or more membrane transporter proteins of the one or more cells.

In some embodiments, the cell membrane-permeable reagent is associated with the cell membranes of the one or more cells. For example, the cell membrane-permeable reagent can be a lipid (or a hydrophobic molecule) that can be inserted into the cell membrane.

In some embodiments, the cell membrane-permeable cellular component-binding reagent comprises an organic molecule, a peptide, a lipid, or a combination thereof. The organic molecule can comprise a cell-membrane permeable organic molecule. The organic molecule can comprise a dye. The organic molecule can comprise a fluorescent dye. The organic molecule can comprise a ring structure. The ring structure can comprise, for example, 5-50 carbon atoms. The organic molecule can comprise a carbon chain. The lipid can comprise a carbon chain. The carbon chain can comprise, for example, 5-50 carbon atoms. The organic molecule can be converted into a second organic molecule after being internalized into the one or more cells. The organic molecule can be acetoxymethyl calcein (calcein AM), and wherein the second organic molecule is calcein.

The ring structure can have different numbers of carbon atoms in different embodiments. In some embodiments, the number of carbon atoms in the ring structure can be, or can be about, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or a number or a range between any two of these values. In some embodiments, the number of carbon atoms in the ring structure can be at least, or can be at most, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The carbon chain (of an organic molecule or a lipid, for example) can have different numbers of carbon atoms in different embodiments. In some embodiments, the number of carbon atoms in the carbon chain can be, or can be about, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or a number or a range between any two of these values. In some embodiments, the number of carbon atoms in the carbon chain can be at least, or can be at most, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

In some embodiments, the peptide can comprise a cell membrane-permeable peptide. The peptide can be, for example, 5-30 amino acids in length. The length of the peptide can be different in different embodiments. In some embodiments, the length of the peptide can be, or can be about, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, or a number or a range between any two of these values. In some embodiments, the length of the peptide can be at least, or can be at most, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100. The cell membrane-permeable reagent can insert into the cell membranes of the one or more cells. The cell membrane-permeable reagent can comprise a lipid.

Detectable Moieties

In some embodiments, the detectable moiety comprises an optical moiety, a luminescent moiety, an electrochemically active moiety, a nanoparticle, or a combination thereof. In some embodiments, the luminescent moiety comprises a chemiluminescent moiety, an electroluminescent moiety, a photoluminescent moiety, or a combination thereof. In some embodiments, the photoluminescent moiety comprises a fluorescent moiety, a phosphorescent moiety, or a combination thereof. In some embodiments, the fluorescent moiety comprises a fluorescent dye. In some embodiments, the nanoparticle comprises a quantum dot. In some embodiments, the methods comprise performing a reaction to convert the detectable moiety precursor into the detectable moiety. In some embodiments, performing a reaction to convert the detectable moiety precursor into the detectable moiety comprises contacting the detectable moiety precursor with a substrate. In some such embodiments, contacting the detectable moiety precursor with a substrate yields a detectable byproduct of a reaction between the two molecules.

In some embodiments, the detectable moiety of the cellular component-binding reagent specific oligonucleotide is unique to the cellular component-binding reagent specific oligonucleotide. In some embodiments, the detectable moieties of two cellular component-binding reagent specific oligonucleotides are identical. In some embodiments, the cellular component-binding reagent specific oligonucleotide comprises a second detectable moiety. In some embodiments, the second detectable moiety of the cellular component-binding reagent specific oligonucleotide is unique to the cellular component-binding reagent specific oligonucleotide. In some embodiments, the combination of the detectable moiety and the second detectable moiety of the cellular component-binding reagent specific oligonucleotide is unique to the cellular component-binding reagent specific oligonucleotide. In some embodiments, the first detectable moiety and second detectable moiety are spectrally-distinct optical moieties. Spectrally-distinct optical moieties include optical moieties with distinguishable emission spectra even if their emission spectral may overlap.

In some embodiments, detectable labels, moieties, or markers can be detectable based on, for example, fluorescence emission, absorbance, fluorescence polarization, fluorescence lifetime, fluorescence wavelength, absorbance wavelength, Stokes shift, light scatter, mass, molecular mass, redox, acoustic, Raman, magnetism, radio frequency, enzymatic reactions (including chemiluminescence and electro-chemiluminescence) or combinations thereof. For example, the label may be a fluorophore, a chromophore, an enzyme, an enzyme substrate, a catalyst, a redox label, a radio label, an acoustic label, a Raman (SERS) tag, a mass tag, an isotope tag (e.g., isotopically pure rare earth element), a magnetic particle, a microparticle, a nanoparticle, an oligonucleotide, or any combination thereof. In some embodiments, the label is a fluorophore (i.e., a fluorescent label, fluorescent dye, etc.). Fluorophores of interest may include but are not limited to dyes suitable for use in analytical applications (e.g., flow cytometry, imaging, etc.), such as an acridine dye, anthraquinone dyes, arylmethane dyes, diarylmethane dyes (e.g., diphenyl methane dyes), chlorophyll containing dyes, triarylmethane dyes (e.g., triphenylmethane dyes), azo dyes, diazonium dyes, nitro dyes, nitroso dyes, phthalocyanine dyes, cyanine dyes, asymmetric cyanine dyes, quinon-imine dyes, azine dyes, eurhodin dyes, safranin dyes, indamins, indophenol dyes, fluorine dyes, oxazine dye, oxazone dyes, thiazine dyes, thiazole dyes, xanthene dyes, fluorene dyes, pyronin dyes, fluorine dyes, rhodamine dyes, phenanthridine dyes, as well as dyes combining two or more of the aforementioned dyes (e.g., in tandem), polymeric dyes having one or more monomeric dye units and mixtures of two or more of the aforementioned dyes thereof. A large number of dyes are commercially available from a variety of sources, such as, for example, Molecular Probes (Eugene, OR), Dyomics GmbH (Jena, Germany), Sigma-Aldrich (St. Louis, MO), Sirigen, Inc. (Santa Barbara, CA) and Exciton (Dayton, OH). For example, the fluorophore may include 4-acetamido-4'-isothiocyanatostilbene-2,2'disulfonic acid; acridine and derivatives such as acridine, acridine orange, acridine yellow, acridine red, and acridine isothiocyanate; allophycocyanin, phycoerythrin, peridinin-chlorophyll protein, 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy3.5, Cy5, Cy5.5, and Cy7; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2' 7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; dye-conjugated polymers (i.e., polymer-attached dyes) such as fluorescein isothiocyanate-dextran as well as dyes combining two or more dyes (e.g., in tandem), polymeric dyes having one or more monomeric dye units and mixtures of two or more of the aforementioned dyes or combinations thereof.

The detectable moiety can be selected from a group of spectrally-distinct detectable moieties. Spectrally-distinct detectable moieties include detectable moieties with distinguishable emission spectra even if their emission spectral may overlap. Non-limiting examples of detectable moieties include Xanthene derivatives: fluorescein, rhodamine, Oregon green, eosin, and Texas red; Cyanine derivatives: cyanine, indocarbocyanine, oxacarbocyanine, thiacarbocyanine, and merocyanine; Squaraine derivatives and ring-substituted squaraines, including Seta, SeTau, and Square dyes; Naphthalene derivatives (dansyl and prodan derivatives); Coumarin derivatives; oxadiazole derivatives: pyridyloxazole, nitrobenzoxadiazole and benzoxadiazole; Anthracene derivatives: anthraquinones, including DRAQ5, DRAQ7 and CyTRAK Orange; Pyrene derivatives: cascade blue; Oxazine derivatives: Nile red, Nile blue, cresyl violet, oxazine 170; Acridine derivatives: proflavin, acridine orange, acridine yellow; Arylmethine derivatives: auramine, crystal violet, malachite green; and Tetrapyrrole derivatives: porphin, phthalocyanine, bilirubin. Other non-limiting examples of detectable moieties include Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhodamine B, Texas Red, Allophycocyanin (APC), APC-Cy7 conjugates, Hoechst 33342, DAPI, Hoechst 33258, SYTOX Blue, Chromomycin A3, Mithramycin, YOYO-1, Ethidium Bromide, Acridine Orange, SYTOX Green, TOTO-1, TO-PRO-1, TO-PRO: Cyanine Monomer, Thiazole Orange, CyTRAK Orange, Propidium Iodide (PI), LDS 751, 7-AAD, SYTOX Orange, TOTO-3, TO-PRO-3, DRAQ5, DRAQ7, Indo-1, Fluo-3, Fluo-4, DCFH, DHR, and SNARF.

In some embodiments, fluorophores of interest may include, but are not limited to, dyes suitable for use in analytical applications (e.g., flow cytometry, imaging, etc.), such as an acridine dye, anthraquinone dyes, arylmethane dyes, diarylmethane dyes (e.g., diphenyl methane dyes), chlorophyll containing dyes, triarylmethane dyes (e.g., triphenylmethane dyes), azo dyes, diazonium dyes, nitro dyes, nitroso dyes, phthalocyanine dyes, cyanine dyes, asymmetric cyanine dyes, quinon-imine dyes, azine dyes, eurhodin dyes, safranin dyes, indamins, indophenol dyes, fluorine dyes, oxazine dye, oxazone dyes, thiazine dyes, thiazole dyes, xanthene dyes, fluorene dyes, pyronin dyes, fluorine dyes, rhodamine dyes, phenanthridine dyes, as well as dyes combining two or more dyes (e.g., in tandem) as well as polymeric dyes having one or more monomeric dye units, as well as mixtures of two or more dyes thereof. For example, the fluorophore may be 4-acetamido-4'-isothiocyanatostilbene-2,2'disulfonic acid; acridine and derivatives such as acridine, acridine orange, acrindine yellow, acridine red, and acridine isothiocyanate; allophycocyanin, phycoerythrin, peridinin-chlorophyll protein, 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy5, Cy5.5, and Cy7; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo) benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; dye-conjugated polymers (i.e., polymer-attached dyes) such as fluorescein isothiocyanate-dextran as well as dyes combining two or more of the aforementioned dyes (e.g., in tandem), polymeric dyes having one or more monomeric dye units and mixtures of two or more of the aforementioned dyes thereof.

The group of spectrally distinct detectable moieties can, for example, include five different fluorophores, five different chromophores, a combination of five fluorophores and chromophores, a combination of four different fluorophores and a non-fluorophore, a combination of four chromophores and a non-chromophore, or a combination of four fluorophores and chromophores and a non-fluorophore non-chromophore. In some embodiments, the detectable moieties can be one of 1, 2, 3, 4, 5, 6, 7, 8, 9, 10, 20, 30, 40, 50, 60, 70, 80, 90, 100, 1000, 2000, 3000, 4000, 5000, 6000, 7000, 8000, 9000, 10000, or a number or a range between any two of these values, of spectrally-distinct moieties.

The excitation wavelength of the detectable moieties can vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 nanometers, or a number or a range between any two of these values. The emission wavelength of the detectable moieties can also vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 nanometers, or a number or a range between any two of these values.

The molecular weights of the detectable moieties can vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 Daltons (Da), or a number or a range between any two of these values. The molecular weights of the detectable moieties can also vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 kilo Daltons (kDa), or a number or a range between any two of these values.

In some instances, the fluorophore (i.e., dye) is a fluorescent polymeric dye. Fluorescent polymeric dyes that find use in the subject methods and systems can vary. In some instances of the method, the polymeric dye includes a conjugated polymer.

Conjugated polymers (CPs) are characterized by a delocalized electronic structure which includes a backbone of alternating unsaturated bonds (e.g., double and/or triple bonds) and saturated (e.g., single bonds) bonds, where π-electrons can move from one bond to the other. As such, the conjugated backbone may impart an extended linear structure on the polymeric dye, with limited bond angles between repeat units of the polymer. For example, proteins and nucleic acids, although also polymeric, in some cases do not form extended-rod structures but rather fold into higher-order three-dimensional shapes. In addition, CPs may form "rigid-rod" polymer backbones and experience a limited twist (e.g., torsion) angle between monomer repeat units along the polymer backbone chain. In some instances, the polymeric dye includes a CP that has a rigid rod structure. As summarized above, the structural characteristics of the polymeric dyes can have an effect on the fluorescence properties of the molecules.

Any convenient polymeric dye may be utilized in the subject methods and systems. In some instances, a polymeric dye is a multichromophore that has a structure capable of harvesting light to amplify the fluorescent output of a fluorophore. In some instances, the polymeric dye is capable of harvesting light and efficiently converting it to emitted light at a longer wavelength. In some embodiments, the polymeric dye has a light-harvesting multichromophore system that can efficiently transfer energy to nearby luminescent species (e.g., a "signaling chromophore"). Mechanisms for energy transfer include, for example, resonant energy transfer (e.g., Forster (or fluorescence) resonance energy transfer, FRET), quantum charge exchange (Dexter energy transfer) and the like. In some instances, these energy transfer mechanisms are relatively short range; that is, close proximity of the light harvesting multichromophore system to the signaling chromophore provides for efficient energy transfer. Under conditions for efficient energy transfer, amplification of the emission from the signaling chromophore occurs when the number of individual chromophores in the light harvesting multichromophore system is large; that is, the emission from the signaling chromophore is more intense when the incident light (the "excitation light") is at a wavelength which is absorbed by the light harvesting multichromophore system than when the signaling chromophore is directly excited by the pump light.

The multichromophore may be a conjugated polymer. Conjugated polymers (CPs) are characterized by a delocalized electronic structure and can be used as highly responsive optical reporters for chemical and biological targets. Because the effective conjugation length is substantially shorter than the length of the polymer chain, the backbone contains a large number of conjugated segments in close proximity. Thus, conjugated polymers are efficient for light harvesting and enable optical amplification via energy transfer.

In some instances the polymer may be used as a direct fluorescent reporter, for example fluorescent polymers having high extinction coefficients, high brightness, etc. In some instances, the polymer may be used as a strong chromophore where the color or optical density is used as an indicator.

Polymeric dyes of interest include, but are not limited to, those dyes described by Gaylord et al. in US Publication Nos. 20040142344, 20080293164, 20080064042, 20100136702, 20110256549, 20120028828, 20120252986, 20130190193 and 20160025735 the disclosures of which are herein incorporated by reference in their entirety; and Gaylord et al., J. Am. Chem. Soc., 2001, 123 (26), pp 6417-6418; Feng et al., Chem. Soc. Rev., 2010, 39, 2411-2419; and Traina et al., J. Am. Chem. Soc., 2011, 133 (32), pp 12600-12607, the disclosures of which are herein incorporated by reference in their entirety.

In some embodiments, the polymeric dye includes a conjugated polymer including a plurality of first optically active units forming a conjugated system, having a first absorption wavelength (e.g., as described herein) at which the first optically active units absorbs light to form an excited state. The conjugated polymer (CP) may be polycationic, polyanionic and/or a charge-neutral conjugated polymer.

The CPs may be water soluble for use in biological samples. Any convenient substituent groups may be included in the polymeric dyes to provide for increased water-solubility, such as a hydrophilic substituent group, e.g., a hydrophilic polymer, or a charged substituent group, e.g., groups that are positively or negatively charged in an aqueous solution, e.g., under physiological conditions. Any convenient water-soluble groups (WSGs) may be utilized in the subject light harvesting multichromophores. The term "water-soluble group" refers to a functional group that is well solvated in aqueous environments and that imparts improved water solubility to the molecules to which it is attached. In some embodiments, a WSG increases the solubility of the multichromophore in a predominantly aqueous solution (e.g., as described herein), as compared to a multichromophore which lacks the WSG. The water soluble groups may be any convenient hydrophilic group that is well solvated in aqueous environments. In some embodiments, the hydrophilic water soluble group is charged, e.g., positively or negatively charged or zwitterionic. In some embodiments, the hydrophilic water soluble group is a neutral hydrophilic group. In some embodiments, the WSG is a hydrophilic polymer, e.g., a polyethylene glycol, a cellulose, a chitosan, or a derivative thereof.

As used herein, the terms "polyethylene oxide", "PEO", "polyethylene glycol" and "PEG" are used interchangeably and refer to a polymer including a chain described by the formula —($CH_2$—$CH_2$—O—)$_n$— or a derivative thereof. In some embodiments, "n" is 5000 or less, such as 1000 or less, 500 or less, 200 or less, 100 or less, 50 or less, 40 or less, 30 or less, 20 or less, 15 or less, such as 5 to 15, or 10 to 15. It is understood that the PEG polymer may be of any convenient length and may include a variety of terminal groups, including but not limited to, alkyl, aryl, hydroxyl, amino, acyl, acyloxy, and amido terminal groups. Functionalized PEGs that may be adapted for use in the subject multichromophores include those PEGs described by S. Zalipsky in "Functionalized poly(ethylene glycol) for preparation of biologically relevant conjugates", Bioconjugate Chemistry 1995, 6 (2), 150-165. Water soluble groups of interest include, but are not limited to, carboxylate, phosphonate, phosphate, sulfonate, sulfate, sulfinate, ester, polyethylene glycols (PEG) and modified PEGs, hydroxyl, amine, ammonium, guanidinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —$SO_3$M', —$PO_3$M', —$NR_3^+$, Y', ($CH_2CH_2O$)$_p$R and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —($CH_2CH_2O$)$_{yy}$$CH_2CH_2XR^{yy}$, —($CH_2CH_2O$)$_{yy}$$CH_2CH_2X$—, —X($CH_2CH_2O$)$_{yy}$$CH_2CH_2$—, glycol, and polyethylene glycol, wherein yy is selected from 1 to 1000, X is selected from 0, S, and $NR^{ZZ}$, and $R^{ZZ}$ and $R^{YY}$ are independently selected from H and C1-3 alkyl.

The polymeric dye may have any convenient length. In some embodiments, the particular number of monomeric repeat units or segments of the polymeric dye may fall within the range of 2 to 500,000, such as 2 to 100,000, 2 to 30,000, 2 to 10,000, 2 to 3,000 or 2 to 1,000 units or segments, or such as 100 to 100,000, 200 to 100,000, or 500 to 50,000 units or segments. In some embodiments, the number of monomeric repeat units or segments of the polymeric dye is within the range of 2 to 1000 units or segments, such as from 2 to 750 units or segments, such as from 2 to 500 units or segments, such as from 2 to 250 units or segment, such as from 2 to 150 units or segment, such as from 2 to 100 units or segments, such as from 2 to 75 units or segments, such as from 2 to 50 units or segments and including from 2 to 25 units or segments.

The polymeric dyes may be of any convenient molecular weight (MW). In some embodiments, the MW of the polymeric dye may be expressed as an average molecular weight. In some instances, the polymeric dye has an average molecular weight of from 500 to 500,000, such as from 1,000 to 100,000, from 2,000 to 100,000, from 10,000 to 100,000 or even an average molecular weight of from 50,000 to 100,000. In some embodiments, the polymeric dye has an average molecular weight of 70,000.

In some embodiments, the polymeric dye includes the following structure:

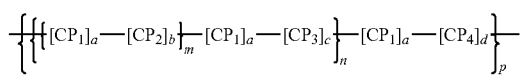

wherein $CP_1$, $CP_2$, $CP_3$ and $CP_4$ are independently a conjugated polymer segment or an oligomeric structure, wherein one or more of $CP_1$, $CP_2$, $CP_3$ and $CP_4$ are bandgap-modifying π-conjugated repeat units.

In some embodiments, the conjugated polymer is a polyfluorene conjugated polymer, a polyphenylene vinylene conjugated polymer, a polyphenylene ether conjugated polymer, a polyphenylene polymer, among other types of conjugated polymers.

In some instances, the polymeric dye includes the following structure:

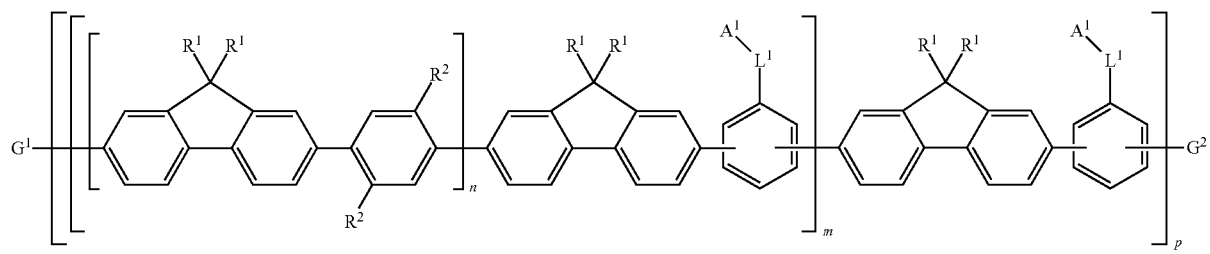

wherein each $R^1$ is independently a solubilizing group or a linker-dye; $L^1$ and $L^2$ are optional linkers; each $R^2$ is independently H or an aryl substituent; each $A^1$ and $A^2$ is independently H, an aryl substituent or a fluorophore; $G^1$ and $G^2$ are each independently selected from the group consisting of a terminal group, a πconjugated segment, a linker and a linked specific binding member; each n and each m are independently 0 or an integer from 1 to 10,000; and p is an integer from 1 to 100,000. Solubilizing groups of interest include, but is not limited to a water-soluble functional group such as a hydrophilic polymer (e.g., polyalkylene oxide, cellulose, chitosan, etc.), as well as alkyl, aryl and heterocycle groups further substituted with a hydrophilic group such as a polyalkylene oxide (e.g., polyethylglycol including a PEG of 2-20 units), an ammonium, a sulphonium, a phosphonium, as well has a charged (positively, negatively or zwitterionic) hydrophilic water soluble group and the like.

In some embodiments, the polymeric dye includes, as part of the polymeric backbone, a conjugated segment having one of the following structures:

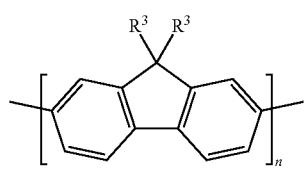

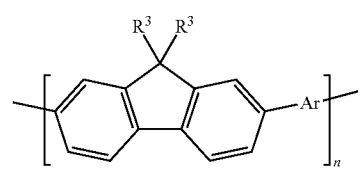

where each $R^3$ is independently an optionally substituted water-soluble functional group such as a hydrophilic polymer (e.g., polyalkylene oxide, cellulose, chitosan, etc.) or an alkyl or aryl group further substituted with a hydrophilic group such as a polyalkylene oxide (e.g., polyethylglycol including a PEG of 2-20 units), an ammonium, a sulphonium, a phosphonium, as well has a charged (positively, negatively or zwitterionic) hydrophilic water soluble group; Ar is an optionally substituted aryl or heteroaryl group; and n is 1 to 10000. In some embodiments, R3 is an optionally substituted alkyl group. In some embodiments, $R^3$ is an optionally substituted aryl group. In some embodiments, $R^3$ is substituted with a polyethyleneglycol, a dye, a chemoselective functional group or a specific binding moiety. In some embodiments, Ar is substituted with a polyethyleneglycol, a dye, a chemoselective functional group or a specific binding moiety.

In some embodiments, the polymeric dye includes the following structure:

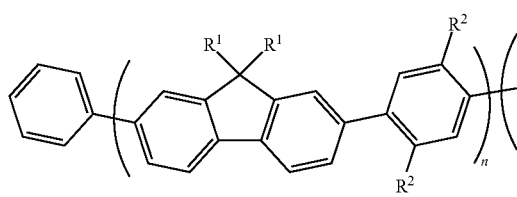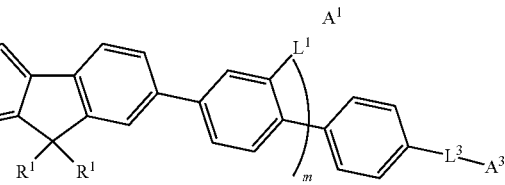

wherein each $R^1$ is a solubilizing group or a linker dye group; each $R^2$ is independently H or an aryl substituent; $L_1$ and $L_2$ are optional linkers; each A1 and A3 are independently H, a fluorophore, a functional group or a specific binding moiety (e.g., an antibody); and n and m are each independently 0 to 10000, wherein n+m>1.

The polymeric dye may have one or more desirable spectroscopic properties, such as a particular absorption maximum wavelength, a particular emission maximum wavelength, extinction coefficient, quantum yield, and the like (see e.g., Chattopadhyay et al., "Brilliant violet fluorophores: A new class of ultrabright fluorescent compounds for immunofluorescence experiments." Cytometry Part A, 81A (6), 456-466, 2012).

In some embodiments, the polymeric dye has an absorption curve between 280 and 850 nm. In some embodiments, the polymeric dye has an absorption maximum in the range 280 and 850 nm. In some embodiments, the polymeric dye absorbs incident light having a wavelength in the range between 280 and 850 nm, where specific examples of absorption maxima of interest include, but are not limited to: 348 nm, 355 nm, 405 nm, 407 nm, 445 nm, 488 nm, 640 nm and 652 nm. In some embodiments, the polymeric dye has an absorption maximum wavelength in a range selected from the group consisting of 280-310 nm, 305-325 nm, 320-350 nm, 340-375 nm, 370-425 nm, 400-450 nm, 440-500 nm, 475-550 nm, 525-625 nm, 625-675 nm and 650-750 nm. In some embodiments, the polymeric dye has an absorption maximum wavelength of 348 nm. In some embodiments, the polymeric dye has an absorption maximum wavelength of 355 nm. In some embodiments, the polymeric dye has an absorption maximum wavelength of 405 nm. In some embodiments, the polymeric dye has an absorption maximum wavelength of 407 nm. In some embodiments, the polymeric dye has an absorption maximum wavelength of 445 nm. In some embodiments, the polymeric dye has an absorption maximum wavelength of 488 nm. In some embodiments, the polymeric dye has an absorption maximum wavelength of 640 nm. In some embodiments, the polymeric dye has an absorption maximum wavelength of 652 nm.

In some embodiments, the polymeric dye has an emission maximum wavelength ranging from 400 to 850 nm, such as 415 to 800 nm, where specific examples of emission maxima of interest include, but are not limited to: 395 nm, 421 nm, 445 nm, 448 nm, 452 nm, 478 nm, 480 nm, 485 nm, 491 nm, 496 nm, 500 nm, 510 nm, 515 nm, 519 nm, 520 nm, 563 nm, 570 nm, 578 nm, 602 nm, 612 nm, 650 nm, 661 nm, 667 nm, 668 nm, 678 nm, 695 nm, 702 nm, 711 nm, 719 nm, 737 nm, 785 nm, 786 nm, 805 nm. In some embodiments, the polymeric dye has an emission maximum wavelength in a range selected from the group consisting of 380-400 nm, 410-430 nm, 470-490 nm, 490-510 nm, 500-520 nm, 560-580 nm, 570-595 nm, 590-610 nm, 610-650 nm, 640-660 nm, 650-700 nm, 700-720 nm, 710-750 nm, 740-780 nm and 775-795 nm. In some embodiments, the polymeric dye has an emission maximum of 395 nm. In some embodiments, the polymeric dye has an emission maximum wavelength of 421 nm. In some embodiments, the polymeric dye has an emission maximum wavelength of 478 nm. In some embodiments, the polymeric dye has an emission maximum wavelength of 480 nm. In some embodiments, the polymeric dye has an emission maximum wavelength of 485 nm. In some embodiments, the polymeric dye has an emission maximum wavelength of 496 nm. In some embodiments, the polymeric dye has an emission maximum wavelength of 510 nm. In some embodiments, the polymeric dye has an emission maximum wavelength of 570 nm. In some embodiments, the polymeric dye has an emission maximum wavelength of 602 nm. In some embodiments, the polymeric dye has an emission maximum wavelength of 650 nm. In some embodiments, the polymeric dye has an emission maximum wavelength of 711 nm. In some embodiments, the polymeric dye has an emission maximum wavelength of 737 nm. In some embodiments, the polymeric dye has an emission maximum wavelength of 750 nm. In some embodiments, the polymeric dye has an emission maximum wavelength of 786 nm. In some embodiments, the polymeric dye has an emission maximum wavelength of 421 nm±5 nm. In some embodiments, the polymeric dye has an emission maximum wavelength of 510 nm±5 nm. In some embodiments, the polymeric dye has an emission maximum wavelength of 570 nm±5 nm. In some embodiments, the polymeric dye has an emission maximum wavelength of 602 nm±5 nm. In some embodiments, the polymeric dye has an emission maximum wavelength of 650 nm±5 nm. In some embodiments, the polymeric dye has an emission maximum wavelength of 711 nm±5 nm. In some embodiments, the polymeric dye has an emission maximum wavelength of 786 nm±5 nm. In some embodiments, the polymeric dye has an emission maximum selected from the group consisting of 421 nm, 510 nm, 570 nm, 602 nm, 650 nm, 711 nm and 786 nm.

In some embodiments, the polymeric dye has an extinction coefficient of $1 \times 10^6$ cm$^{-1}$M$^{-1}$ or more, such as $2 \times 10^6$ cm$^{-1}$M$^{-1}$ or more, $2.5 \times 10^6$ cm$^{-1}$M$^{-1}$ or more, $3 \times 10^6$ cm$^{-1}$M$^{-1}$ or more, $4 \times 10^6$ cm$^{-1}$M$^{-1}$ or more, $5 \times 10^6$ cm$^{-1}$M$^{-1}$ or more, $6 \times 10^6$ cm$^{-1}$M$^{-1}$ or more, $7 \times 10^6$ cm$^{-1}$M$^{-1}$ or more, or $8 \times 10^6$ cm$^{-1}$M$^{-1}$ or more. In some embodiments, the polymeric dye has a quantum yield of 0.05 or more, such as 0.1 or more, 0.15 or more, 0.2 or more, 0.25 or more, 0.3 or more, 0.35 or more, 0.4 or more, 0.45 or more, 0.5 or more, 0.6 or more, 0.7 or more, 0.8 or more, 0.9 or more, 0.95 or more, 0.99 or more and including 0.999 or more. For example, the quantum yield of polymeric dyes of interest may range from 0.05 to 1, such as from 0.1 to 0.95, such as from 0.15 to 0.9, such as from 0.2 to 0.85, such as from 0.25 to 0.75, such as from 0.3 to 0.7 and including a quantum yield of from 0.4 to 0.6. In some embodiments, the polymeric dye has a quantum yield of 0.1 or more. In some embodiments, the polymeric dye has a quantum yield of 0.3 or more. In some embodiments, the polymeric dye has a quantum yield of 0.5 or more. In some embodiments, the polymeric dye has a quantum yield of 0.6 or more. In some embodiments, the polymeric dye has a quantum yield of 0.7 or more. In some embodiments, the polymeric dye has a quantum yield of 0.8 or more. In some embodiments, the polymeric dye has a quantum yield of 0.9 or more. In some embodiments, the polymeric dye has a quantum yield of 0.95 or more. In some embodiments, the polymeric dye has an extinction coefficient of $1\times10^6$ or more and a quantum yield of 0.3 or more. In some embodiments, the polymeric dye has an extinction coefficient of $2\times106$ or more and a quantum yield of 0.5 or more.

Methods

Disclosed herein are a variety of different methods which may employ oligonucleotide comprising cellular component-binding reagents having detectable moieties associated therewith. Disclosed herein are methods of quantitative analysis of a plurality of cellular component targets of cells of interest. Disclosed herein include methods of obtaining cells of interest from the plurality of cells based on the detectable moieties of the cellular component-binding reagent specific oligonucleotides associated with the cellular component-binding reagents (or lack thereof). In some embodiments, obtaining the cells of interest comprises obtaining the cells of interest flow cytometrically based on the fluorescent moieties, or the phosphorescent moieties, of the cellular component-binding reagent specific oligonucleotides associated with the cellular component-binding reagents (or lack thereof). In some embodiments, one or more experiments can be performed on a plurality of cells using the detectable moieties of the cellular component-binding reagent specific oligonucleotides associated with the cellular component-binding reagents, or lack thereof, to obtain an experiment result. In some embodiments, cells of interest are selected from cells associated with the cellular component-binding reagents based on the experiment result. Also disclosed herein are methods comprising an analysis of the experiment result of the cells and the number of copies of each of the cellular component targets of the cells associated with the cellular component-binding reagents (e.g., correlating the experiment result of the cells and the number of copies of each of the cellular component targets of the cells associated with the cellular component-binding reagents). In some embodiments there are provided oligonucleotides associated with a cellular component-binding reagent comprising one or more detectable moieties for use in methods of determining protein expression and gene expression simultaneously and for sample indexing. Disclosed herein include methods of determining whether a cellular constituent in a sample comprises a cellular component target of interest. Aspects of the methods include: producing a detectably labeled sample comprising a cellular component-binding reagent, wherein the cellular component-binding reagent is associated with a cellular component-binding reagent specific oligonucleotide associated with a detectable moiety and comprising an identifier sequence for the cellular component-binding reagent that the cellular component-binding reagent specific oligonucleotide is associated therewith, and wherein the cellular component-binding reagent is capable of specifically binding to the cellular component target of interest; and assaying cellular constituents of the detectably labeled sample for the detectable moiety to determine whether a cellular constituent in a cellular sample comprises the cellular component target of interest. Embodiments of such methods further include separating cellular constituents that comprise the cellular component target of interest from other constituents of the cellular sample. In some instances the methods further comprise isolating a cellular constituent that comprises the cellular component target of interest into a single cell sample, e.g., in a partition. In some instances, the methods further comprise producing barcoded identifier sequences from the single cell sample. In some instances, the methods further comprise sequencing the barcoded identifier sequences to obtain sequence information for the single cell sample. In some instances, the methods further comprise quantitating the cellular component target of interest for the cellular constituent of the single cell sample from the sequence information. In some instances, the methods further comprise transcriptome analysis of the cellular constituents of the cellular sample that comprise the cellular component target of interest. These methods are now reviewed in greater detail.

Methods of Quantitative Analysis of Cellular Component Targets

In some embodiments, the methods disclosed herein can be used for quantitative analysis of a plurality of cellular component targets (for example, protein targets) in a sample using the compositions disclosed herein and oligonucleotide probes that can associate a barcode sequence (e.g., a molecular label sequence) to the oligonucleotides of the cellular component binding reagents (e.g., protein binding reagents). The oligonucleotides of the cellular component binding reagents can be, or comprise, an antibody oligonucleotide, a sample indexing oligonucleotide, a cell identification oligonucleotide, a control particle oligonucleotide, a control oligonucleotide, an interaction determination oligonucleotide, etc. In some embodiments, the sample can be a single cell, a plurality of cells, a tissue sample, a tumor sample, a blood sample, or the like. In some embodiments, the sample can comprise a mixture of cell types, such as normal cells, tumor cells, blood cells, B cells, T cells, maternal cells, fetal cells, etc., or a mixture of cells from different subjects.

In some embodiments, the sample can comprise a plurality of single cells separated into individual compartments, such as microwells in a microwell array.

In some embodiments, the binding target of the plurality of cellular component target (i.e., the cellular component target) can be, or comprise, a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof. In some embodiments, the cellular component target is a protein target. In some embodiments, the plurality of cellular component targets comprises a cell-surface protein, a cell marker, a B-cell receptor, a T-cell receptor, an antibody, a major histocompatibility complex, a tumor antigen, a receptor, or any combination thereof. In some embodiments, the plurality of cellular component targets can comprise intracellular cellular components. In some embodiments, the plurality of cellular components can be at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 70%, at least 80%, at least 90%, at least 95%, at least 98%, at least 99%, or more, of all the encoded cellular components in an organism. In some embodiments, the plurality of cellular component targets can comprise at least 2, at least 3, at least 4, at least 5, at least 10, at least 20, at least 30, at least 40, at least 50, at least 100, at least 1000, at least 10000, or more different cellular component targets.

In some embodiments, the plurality of cellular component binding reagents is contacted with the sample for specific binding with the plurality of cellular component targets.

Unbound cellular component binding reagents can be removed, for example, by washing. In embodiments where the sample comprises cells, any cellular component binding reagents not specifically bound to the cells can be removed.

In some instances, cells from a population of cells can be separated (e.g., isolated) into wells of a substrate of the disclosure. The population of cells can be diluted prior to separating. The population of cells can be diluted such that at least 1%, 5%, 10%, 15%, 20%, 25%, 30%, 35%, 40%, 45%, 50%, 55%, 60%, 65%, 70%, 75%, 80%, 85%, 90%, 95% or 100%, of wells of the substrate receive a single cell. The population of cells can be diluted such that at most 1%, 5%, 10%, 15%, 20%, 25%, 30%, 35%, 40%, 45%, 50%, 55%, 60%, 65%, 70%, 75%, 80%, 85%, 90%, 95%, or 100%, of wells of the substrate receive a single cell. The population of cells can be diluted such that the number of cells in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100%, of the number of wells on the substrate. The population of cells can be diluted such that the number of cells in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100%, of the number of wells on the substrate. In some instances, the population of cells is diluted such that the number of cell is about 10% of the number of wells in the substrate.

Distribution of single cells into wells of the substrate can follow a Poisson distribution. For example, there can be at least a 0.1%, 0.5%, 1%, 2%, 3%, 4%, 5%, 6%, 7%, 8%, 9%, or 10%, or more probability that a well of the substrate has more than one cell. There can be at least a 0.1%, 0.5%, 1%, 2%, 3%, 4%, 5%, 6%, 7%, 8%, 9%, or 10%, or more probability that a well of the substrate has more than one cell. Distribution of single cells into wells of the substrate can be random. Distribution of single cells into wells of the substrate can be non-random. The cells can be separated such that a well of the substrate receives only one cell.

In some embodiments, the cellular component binding reagents can be additionally conjugated with fluorescent molecules to enable flow sorting of cells into individual compartments.

In some embodiments, the methods disclosed herein provide contacting a plurality of compositions with the sample for specific binding with the plurality of cellular component targets. It would be appreciated that the conditions used may allow specific binding of the cellular component binding reagents, e.g., antibodies, to the cellular component targets. Following the contacting step, unbound compositions can be removed. For example, in embodiments where the sample comprises cells, and the compositions specifically bind to cellular component targets are cell-surface cellular components, such as cell-surface proteins, unbound compositions can be removed by washing the cells with buffer such that only compositions that specifically bind to the cellular component targets remain with the cells.

In some embodiments, the methods disclosed herein can comprise associating an oligonucleotide (e.g., a barcode, or a stochastic barcode), including a barcode sequence (such as a molecular label), a cell label, a sample label, etc., or any combination thereof, to the plurality of oligonucleotides associated with the cellular component binding reagents. For example, a plurality of oligonucleotide probes comprising a barcode can be used to hybridize to the plurality of oligonucleotides of the compositions.

In some embodiments, the plurality of oligonucleotide probes can be immobilized on solid supports. The solid supports can be free floating, e.g., beads in a solution. The solid supports can be embedded in a semi-solid or solid array. In some embodiments, the plurality of oligonucleotide probes may not be immobilized on solid supports. When the plurality of oligonucleotide probes are in close proximity to the plurality associated with oligonucleotides of the cellular component binding reagents, the plurality of oligonucleotides of the cellular component binding reagents can hybridize to the oligonucleotide probes. The oligonucleotide probes can be contacted at a non-depletable ratio such that each distinct oligonucleotide of the cellular component binding reagents can associate with oligonucleotide probes having different barcode sequences (e.g., molecular labels) of the disclosure.

In some embodiments, the methods disclosed herein provide detaching the oligonucleotides from the cellular component binding reagents that are specifically bound to the cellular component targets. Detachment can be performed in a variety of ways to separate the chemical group from the cellular component binding reagent, such as UV photocleaving, chemical treatment (e.g., dithiothreitol treatment), heating, enzyme treatment, or any combination thereof. Detaching the oligonucleotide from the cellular component binding reagent can be performed either before, after, or during the step of hybridizing the plurality of oligonucleotide probes to the plurality of oligonucleotides of the compositions.

Methods of Simultaneous Quantitative Analysis of Cellular Component and Nucleic Acid Targets In some embodiments, the methods disclosed herein can be used for simultaneous quantitative analysis of a plurality of cellular component targets (e.g., protein targets) and a plurality of nucleic acid target molecules in a sample using the compositions disclosed herein and oligonucleotide probes that can associate a barcode sequence (e.g., a molecular label sequence) to both the oligonucleotides of the cellular component binding reagents and nucleic acid target molecules. Other methods of simultaneous quantitative analysis of a plurality of cellular component targets and a plurality of nucleic acid target molecules are described in U.S. Patent Application Publication No. US2018/0088112 and U.S. Patent Application Publication No. US2018/0346970; the content of each is incorporated herein by reference in its entirety. In some embodiments, the sample can be a single cell, a plurality of cells, a tissue sample, a tumor sample, a blood sample, or the like. In some embodiments, the sample can comprise a mixture of cell types, such as normal cells, tumor cells, blood cells, B cells, T cells, maternal cells, fetal cells, or a mixture of cells from different subjects.

In some embodiments, the sample can comprise a plurality of single cells separated into individual compartments, such as microwells in a microwell array.

In some embodiments, the plurality of cellular component targets comprises a cell-surface protein, a cell marker, a B-cell receptor, a T-cell receptor, an antibody, a major histocompatibility complex, a tumor antigen, a receptor, or any combination thereof. In some embodiments, the plurality of cellular component targets can comprise intracellular cellular components. In some embodiments, the plurality of cellular components can be, or be about, 1%, 2%, 3%, 4%, 5%, 6%, 7%, 8%, 9%, 10%, 20%, 30%, 40%, 50%, 60%, 70%, 80%, 90%, 95%, 98%, 99%, or a number or a range between any two of these values, of all the cellular components, such as expressed proteins, in an organism, or one or more cells of the organism. In some embodiments, the plurality of cellular components can be at least, or be at most, 1%, 2%, 3%, 4%, 5%, 6%, 7%, 8%, 9%, 10%, 20%, 30%, 40%, 50%, 60%, 70%, 80%, 90%, 95%, 98%, or 99%, of all the cellular components, such as proteins could be expressed, in an organism, or one or more cells of the organism. In some embodiments, the plurality of cellular component targets can comprise, or comprise about, 2, 3, 4, 5, 10, 20, 30, 40, 50, 100, 1000, 10000, or a number or a range between any two of these values, different cellular component targets. In some embodiments, the plurality of cellular component targets can comprise at least, or comprise at most, 2, 3, 4, 5, 10, 20, 30, 40, 50, 100, 1000, or 10000, different cellular component targets.

In some embodiments, the plurality of cellular component binding reagents is contacted with the sample for specific binding with the plurality of cellular component targets. Unbound cellular component binding reagents can be removed, for example, by washing. In embodiments where the sample comprises cells, any cellular component binding reagents not specifically bound to the cells can be removed.

In some instances, cells from a population of cells can be separated (e.g., isolated) into wells of a substrate of the disclosure. The population of cells can be diluted prior to separating. The population of cells can be diluted such that at least 1%, 5%, 10%, 15%, 20%, 25%, 30%, 35%, 40%, 45%, 50%, 55%, 60%, 65%, 70%, 75%, 80%, 85%, 90%, 95%, or 100% of wells of the substrate receive a single cell. The population of cells can be diluted such that at most 1%, 5%, 10%, 15%, 20%, 25%, 30%, 35%, 40%, 45%, 50%, 55%, 60%, 65%, 70%, 75%, 80%, 85%, 90%, 95%, or 100% of wells of the substrate receive a single cell. The population of cells can be diluted such that the number of cells in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100% of the number of wells on the substrate. The population of cells can be diluted such that the number of cells in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100% of the number of wells on the substrate. In some instances, the population of cells is diluted such that the number of cells is about 10% of the number of wells in the substrate.

Distribution of single cells into wells of the substrate can follow a Poisson distribution. For example, there can be at least a 0.1%, 0.5%, 1%, 2%, 3%, 4%, 5%, 6%, 7%, 8%, 9%, or 10%, or more probability that a well of the substrate has more than one cell. There can be at least a 0.1%, 0.5%, 1%, 2%, 3%, 4%, 5%, 6%, 7%, 8%, 9%, or 10%, or more probability that a well of the substrate has more than one cell. Distribution of single cells into wells of the substrate can be random. Distribution of single cells into wells of the substrate can be non-random. The cells can be separated such that a well of the substrate receives only one cell.

In some embodiments, the cellular component binding reagents can be additionally conjugated with fluorescent molecules to enable flow sorting of cells into individual compartments.

In some embodiments, the methods disclosed herein provide contacting a plurality of compositions with the sample for specific binding with the plurality of cellular component targets. It would be appreciated that the conditions used may allow specific binding of the cellular component binding reagents, e.g., antibodies, to the cellular component targets. Following the contacting step, unbound compositions can be removed. For example, in embodiments where the sample comprises cells, and the compositions specifically bind to cellular component targets are on the cell surface, such as cell-surface proteins, unbound compositions can be removed by washing the cells with buffer such that only compositions that specifically bind to the cellular component targets remain with the cells.

In some embodiments, the methods disclosed herein can provide releasing the plurality of nucleic acid target molecules from the sample, e.g., cells. For example, the cells can be lysed to release the plurality of nucleic acid target molecules. Cell lysis may be accomplished by any of a variety of means, for example, by chemical treatment, osmotic shock, thermal treatment, mechanical treatment, optical treatment, or any combination thereof. Cells may be lysed by addition of a cell lysis buffer comprising a detergent (e.g., SDS, Li dodecyl sulfate, Triton X-100, Tween-20, or NP-40), an organic solvent (e.g., methanol or acetone), or digestive enzymes (e.g., proteinase K, pepsin, or trypsin), or any combination thereof.

It would be appreciated by one of ordinary skill in the art that the plurality of nucleic acid molecules can comprise a variety of nucleic acid molecules. In some embodiments, the plurality of nucleic acid molecules can comprise, DNA molecules, RNA molecules, genomic DNA molecules, mRNA molecules, rRNA molecules, siRNA molecules, or a combination thereof, and can be double-stranded or single-stranded. In some embodiments, the plurality of nucleic acid molecules comprise, or comprise about, 100, 1000, 10000, 20000, 30000, 40000, 50000, 100000, 1000000, or a number or a range between any two of these values, species. In some embodiments, the plurality of nucleic acid molecules comprises at least, or comprise at most, 100, 1000, 10000, 20000, 30000, 40000, 50000, 100000, or 1000000, species. In some embodiments, the plurality of nucleic acid molecules can be from a sample, such as a single cell, or a plurality of cells. In some embodiments, the plurality of nucleic acid molecules can be pooled from a plurality of samples, such as a plurality of single cells.

In some embodiments, the methods disclosed herein can comprise associating a barcode (e.g., a stochastic barcode), which can include a barcode sequence (such as a molecular label), a cell label, a sample label, etc., or any combination thereof, to the plurality of nucleic acid target molecules and the plurality of oligonucleotides of the cellular component binding reagents. For example, a plurality of oligonucleotide probes comprising a stochastic barcode can be used to hybridize to the plurality of nucleic acid target molecules and the plurality of oligonucleotides of the compositions.

In some embodiments, the plurality of oligonucleotide probes can be immobilized on solid supports. The solid supports can be free floating, e.g., beads in a solution. The solid supports can be embedded in a semi-solid or solid array. In some embodiments, the plurality of oligonucleotide probes may not be immobilized on solid supports. When the plurality of oligonucleotide probes are in close proximity to the plurality of nucleic acid target molecules and the plurality of oligonucleotides of the cellular component binding reagents, the plurality of nucleic acid target molecules and the plurality of oligonucleotides of the cellular component binding reagents can hybridize to the oligonucleotide probes. The oligonucleotide probes can be contacted at a non-depletable ratio such that each distinct nucleic acid target molecules and oligonucleotides of the cellular component binding reagents can associate with oligonucleotide probes having different barcode sequences (e.g., molecular labels) of the disclosure.

In some embodiments, the methods disclosed herein provide detaching the oligonucleotides from the cellular component binding reagents that are specifically bound to the cellular component targets. Detachment can be performed in a variety of ways to separate the chemical group from the cellular component binding reagent, such as UV photocleaving, chemical treatment (e.g., dithiothreitol treatment), heating, enzyme treatment, or any combination thereof. Detaching the oligonucleotide from the cellular component binding reagent can be performed either before, after, or during the step of hybridizing the plurality of oligonucleotide probes to the plurality of nucleic acid target molecules and the plurality of oligonucleotides of the compositions.

Simultaneous Quantitative Analysis of Protein and Nucleic Acid Targets

Figure 6:
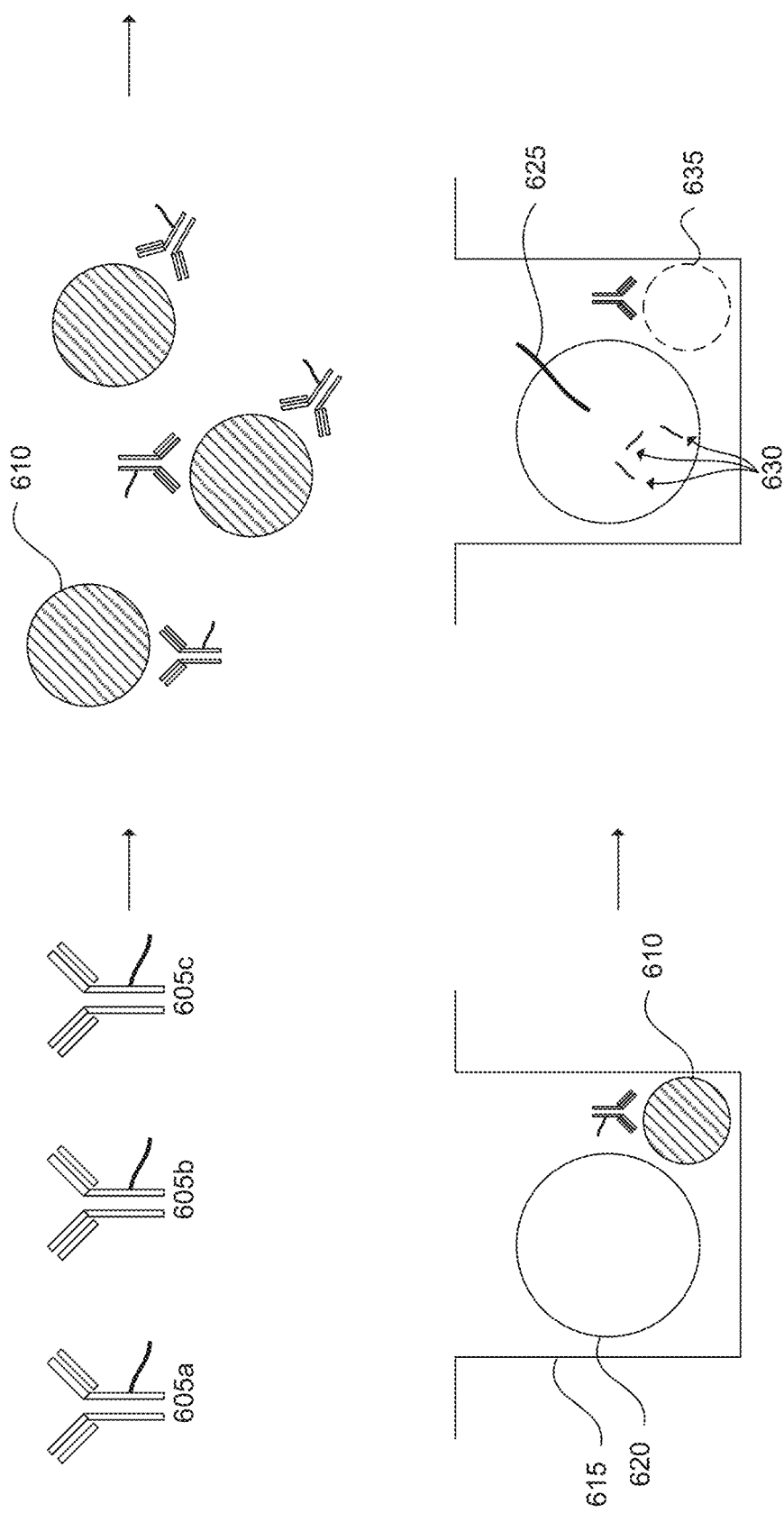
FIG. 6 shows a schematic illustration of an exemplary workflow of using oligonucleotide-associated antibodies to determine cellular component expression (e.g., protein expression) and gene expression simultaneously in a high throughput manner.

In some embodiments, the methods disclosed herein also can be used for simultaneous quantitative analysis of multiple types of target molecules, for example protein and nucleic acid targets. For example, the target molecules can be, or comprise, cellular components. FIG. 6 shows a schematic illustration of an exemplary method of simultaneous quantitative analysis of both nucleic acid targets and other cellular component targets (e.g., proteins) in single cells. In some embodiments, a plurality of compositions 605, 605*b*, 605*c*, etc., each comprising a cellular component binding reagent, such as an antibody, is provided. Different cellular component binding reagents, such as antibodies, which bind to different cellular component targets are conjugated with different unique identifiers. Next, the cellular component binding reagents can be incubated with a sample containing a plurality of cells 610. The different cellular component binding reagents can specifically bind to cellular components on the cell surface, such as a cell marker, a B-cell receptor, a T-cell receptor, an antibody, a major histocompatibility complex, a tumor antigen, a receptor, or any combination thereof. Unbound cellular component binding reagents can be removed, e.g., by washing the cells with a buffer. The cells with the cellular component binding reagents can be then separated into a plurality of compartments, such as a microwell array, wherein a single compartment 615 is sized to fit a single cell and a single bead 620. Each bead can comprise a plurality of oligonucleotide probes, which can comprise a cell label that is common to all oligonucleotide probes on a bead, and barcode sequences (e.g., molecular label sequences). In some embodiments, each oligonucleotide probe can comprise a target binding region, for example, a poly(dT) sequence. The oligonucleotides 625 conjugated to the cellular component binding reagent can be detached from the cellular component binding reagent using chemical, optical or other means. The cell can be lysed 635 to release nucleic acids within the cell, such as genomic DNA or cellular mRNA 630. Cellular mRNA 630, oligonucleotides 625 or both can be captured by the oligonucleotide probes on bead 620, for example, by hybridizing to the poly(dT) sequence. A reverse transcriptase can be used to extend the oligonucleotide probes hybridized to the cellular mRNA 630 and the oligonucleotides 625 using the cellular mRNA 630 and the oligonucleotides 625 as templates. The extension products produced by the reverse transcriptase can be subject to amplification and sequencing. Sequencing reads can be subject to demultiplexing of sequences or identifies of cell labels, barcodes (e.g., molecular labels), genes, cellular component binding reagent specific oligonucleotides (e.g., antibody specific oligonucleotides), etc., which can give rise to a digital representation of cellular components and gene expression of each single cell in the sample.

Sample Indexing Using Oligonucleotide-Conjugated Cellular Component Binding Reagent Disclosed herein include methods for sample identification. In some embodiments, the method comprises: contacting one or more cells from each of a plurality of samples with a sample indexing composition of a plurality of sample indexing compositions, wherein each of the one or more cells comprises one or more cellular component targets, wherein each of the plurality of sample indexing compositions comprises a cellular component binding reagent associated with a sample indexing oligonucleotide, wherein the cellular component binding reagent is capable of specifically binding to at least one of the one or more cellular component targets, wherein the sample indexing oligonucleotide comprises a sample indexing sequence, and wherein sample indexing sequences of at least two sample indexing compositions of the plurality of sample indexing compositions comprise different sequences; removing unbound sample indexing compositions of the plurality of sample indexing compositions; barcoding (e.g., stochastically barcoding) the sample indexing oligonucleotides using a plurality of barcodes (e.g., stochastic barcodes) to create a plurality of barcoded sample indexing oligonucleotides; obtaining sequencing data of the plurality of barcoded sample indexing oligonucleotides; and identifying sample origin of at least one cell of the one or more cells based on the sample indexing sequence of at least one barcoded sample indexing oligonucleotide of the plurality of barcoded sample indexing oligonucleotides.

In some embodiments, barcoding the sample indexing oligonucleotides using the plurality of barcodes comprises: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

An oligonucleotide-conjugated with an antibody, an oligonucleotide for conjugation with an antibody, or an oligonucleotide previously conjugated with an antibody is referred to herein as an antibody oligonucleotide ("AbOligo"). Antibody oligonucleotides in the context of sample indexing are referred to herein as sample indexing oligonucleotides. An antibody conjugated with an antibody oligonucleotide is referred to herein as a hot antibody or an oligonucleotide antibody. An antibody not conjugated with an antibody oligonucleotide is referred to herein as a cold antibody or an oligonucleotide free antibody. An oligonucleotide-conjugated with a binding reagent (e.g., a protein binding reagent), an oligonucleotide for conjugation with a binding reagent, or an oligonucleotide previously conjugated with a binding reagent is referred to herein as a reagent oligonucleotide. Reagent oligonucleotides in the context of sample indexing are referred to herein as sample indexing oligonucleotides. A binding reagent conjugated with an antibody oligonucleotide is referred to herein as a hot binding reagent or an oligonucleotide binding reagent. A binding reagent not conjugated with an antibody oligonucleotide is referred to herein as a cold binding reagent or an oligonucleotide free binding reagent.

Figure 7:
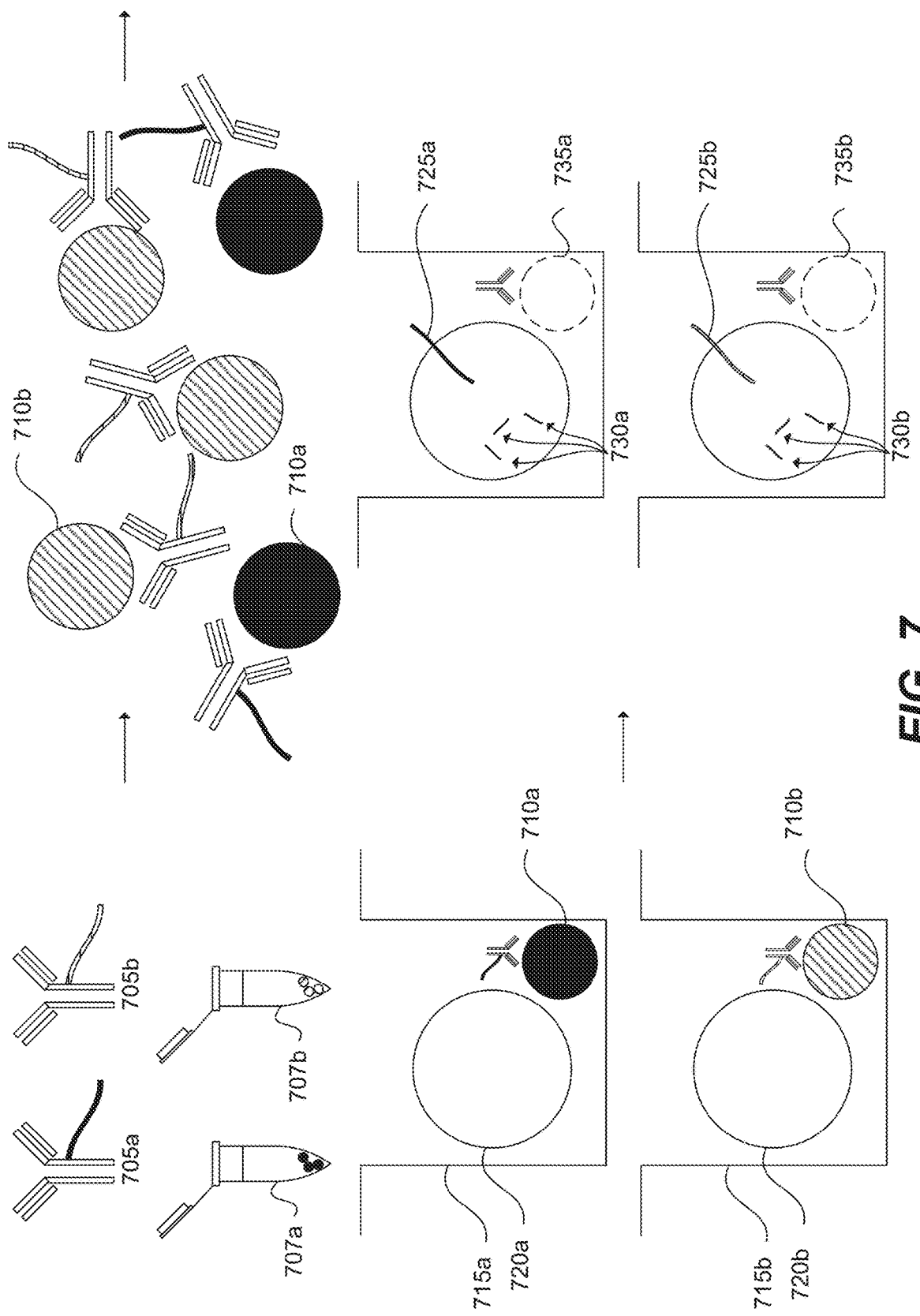
FIG. 7 shows a schematic illustration of an exemplary workflow of using oligonucleotide-associated antibodies for sample indexing.

FIG. 7 shows a schematic illustration of an exemplary workflow using oligonucleotide-associated cellular component binding reagents for sample indexing. In some embodiments, a plurality of compositions 705a, 705b, etc., each comprising a binding reagent is provided. The binding reagent can be a protein binding reagent, such as an antibody. The cellular component binding reagent can comprise an antibody, a tetramer, an aptamer, a protein scaffold, or a combination thereof. The binding reagents of the plurality of compositions 705a, 705b can bind to an identical cellular component target. For example, the binding reagents of the plurality of compositions 705, 705b can be identical (except for the sample indexing oligonucleotides associated with the binding reagents).

Different compositions can include binding reagents conjugated with sample indexing oligonucleotides with different sample indexing sequences. The number of different compositions can be different in different implementations. In some embodiments, the number of different compositions can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values. In some embodiments, the number of different compositions can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000.

In some embodiments, the sample indexing oligonucleotides of binding reagents in one composition can include an identical sample indexing sequence. The sample indexing oligonucleotides of binding reagents in one composition may not be identical. In some embodiments, the percentage of sample indexing oligonucleotides of binding reagents in one composition with an identical sample indexing sequence can be, or be about, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or a number or a range between any two of these values. In some embodiments, the percentage of sample indexing oligonucleotides of binding reagents in one composition with an identical sample indexing sequence can be at least, or be at most, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9%.

The compositions 705a and 705b can be used to label samples of different samples. For example, the sample indexing oligonucleotides of the cellular component binding reagent in the composition 705a can have one sample indexing sequence and can be used to label cells 710a, shown as black circles, in a sample 707a, such as a sample of a patient. The sample indexing oligonucleotides of the cellular component binding reagents in the composition 705b can have another sample indexing sequence and can be used to label cells 710b, shown as hatched circles, in a sample 707b, such as a sample of another patient or another sample of the same patient. The cellular component binding reagents can specifically bind to cellular component targets or proteins on the cell surface, such as a cell marker, a B-cell receptor, a T-cell receptor, an antibody, a major histocompatibility complex, a tumor antigen, a receptor, or any combination thereof. Unbound cellular component binding reagents can be removed, e.g., by washing the cells with a buffer.

The cells with the cellular component binding reagents can be then separated into a plurality of compartments, such as a microwell array, wherein a single compartment 715a, 715b is sized to fit a single cell 710a and a single bead 720a or a single cell 710b and a single bead 720b. Each bead 720a, 720b can comprise a plurality of oligonucleotide probes, which can comprise a cell label that is common to all oligonucleotide probes on a bead, and molecular label sequences. In some embodiments, each oligonucleotide probe can comprise a target binding region, for example, a poly(dT) sequence. The sample indexing oligonucleotides 725a conjugated to the cellular component binding reagent of the composition 705a can be configured to be (or can be) detachable or non-detachable from the cellular component binding reagent. The sample indexing oligonucleotides 725a conjugated to the cellular component binding reagent of the composition 705a can be detached from the cellular component binding reagent using chemical, optical or other means. The sample indexing oligonucleotides 725b conjugated to the cellular component binding reagent of the composition 705b can be configured to be (or can be) detachable or non-detachable from the cellular component binding reagent. The sample indexing oligonucleotides 725b conjugated to the cellular component binding reagent of the composition 705b can be detached from the cellular component binding reagent using chemical, optical or other means.

The cell 710a can be lysed to release nucleic acids within the cell 710a, such as genomic DNA or cellular mRNA 730a. The lysed cell 735a is shown as a dotted circle. Cellular mRNA 730a, sample indexing oligonucleotides 725a, or both can be captured by the oligonucleotide probes on bead 720a, for example, by hybridizing to the poly(dT) sequence. A reverse transcriptase can be used to extend the oligonucleotide probes hybridized to the cellular mRNA 730a and the oligonucleotides 725a using the cellular mRNA 730a and the oligonucleotides 725a as templates. The extension products produced by the reverse transcriptase can be subject to amplification and sequencing.

Similarly, the cell 710b can be lysed to release nucleic acids within the cell 710b, such as genomic DNA or cellular mRNA 730b. The lysed cell 735b is shown as a dotted circle. Cellular mRNA 730b, sample indexing oligonucleotides 725b, or both can be captured by the oligonucleotide probes on bead 720b, for example, by hybridizing to the poly(dT) sequence. A reverse transcriptase can be used to extend the oligonucleotide probes hybridized to the cellular mRNA 730b and the oligonucleotides 725b using the cellular mRNA 730b and the oligonucleotides 725b as templates. The extension products produced by the reverse transcriptase can be subject to amplification and sequencing.

Sequencing reads can be subject to demultiplexing of cell labels, molecular labels, gene identities, and sample identities (e.g., in terms of sample indexing sequences of sample indexing oligonucleotides 725a and 725b). Demultiplexing of cell labels, molecular labels, and gene identities can give rise to a digital representation of gene expression of each single cell in the sample. Demultiplexing of cell labels, molecular labels, and sample identities, using sample indexing sequences of sample indexing oligonucleotides, can be used to determine a sample origin.

In some embodiments, cellular component binding reagents against cellular component binding reagents on the cell surface can be conjugated to a library of unique sample indexing oligonucleotides to allow cells to retain sample identity. For example, antibodies against cell surface markers can be conjugated to a library of unique sample indexing oligonucleotides to allow cells to retain sample identity. This will enable multiple samples to be loaded onto the same Rhapsody™ cartridge as information pertaining sample source is retained throughout library preparation and sequencing. Sample indexing can allow multiple samples to be run together in a single experiment, simplifying and shortening experiment time, and eliminating batch effect.

Disclosed herein include methods for sample identification. In some embodiments, the method comprise: contacting one or more cells from each of a plurality of samples with a sample indexing composition of a plurality of sample indexing compositions, wherein each of the one or more cells comprises one or more cellular component targets, wherein each of the plurality of sample indexing compositions comprises a cellular component binding reagent associated with a sample indexing oligonucleotide, wherein the cellular component binding reagent is capable of specifically binding to at least one of the one or more cellular component targets, wherein the sample indexing oligonucleotide comprises a sample indexing sequence, and wherein sample indexing sequences of at least two sample indexing compositions of the plurality of sample indexing compositions comprise different sequences; removing unbound sample indexing compositions of the plurality of sample indexing compositions. The method can include barcoding (e.g., stochastically barcoding) the sample indexing oligonucleotides using a plurality of barcodes (e.g., stochastic barcodes) to create a plurality of barcoded sample indexing oligonucleotides; obtaining sequencing data of the plurality of barcoded sample indexing oligonucleotides; and identifying sample origin of at least one cell of the one or more cells based on the sample indexing sequence of at least one barcoded sample indexing oligonucleotide of the plurality of barcoded sample indexing oligonucleotides.

In some embodiments, the method for sample identification comprises: contacting one or more cells from each of a plurality of samples with a sample indexing composition of a plurality of sample indexing compositions, wherein each of the one or more cells comprises one or more cellular component targets, wherein each of the plurality of sample indexing compositions comprises a cellular component binding reagent associated with a sample indexing oligonucleotide, wherein the cellular component binding reagent is capable of specifically binding to at least one of the one or more cellular component targets, wherein the sample indexing oligonucleotide comprises a sample indexing sequence, and wherein sample indexing sequences of at least two sample indexing compositions of the plurality of sample indexing compositions comprise different sequences; removing unbound sample indexing compositions of the plurality of sample indexing compositions; and identifying sample origin of at least one cell of the one or more cells based on the sample indexing sequence of at least one sample indexing oligonucleotide of the plurality of sample indexing compositions.

In some embodiments, identifying the sample origin of the at least one cell comprises: barcoding (e.g., stochastically barcoding) sample indexing oligonucleotides of the plurality of sample indexing compositions using a plurality of barcodes (e.g., stochastic barcodes) to create a plurality of barcoded sample indexing oligonucleotides; obtaining sequencing data of the plurality of barcoded sample indexing oligonucleotides; and identifying the sample origin of the cell based on the sample indexing sequence of at least one barcoded sample indexing oligonucleotide of the plurality of barcoded sample indexing oligonucleotides. In some embodiments, barcoding the sample indexing oligonucleotides using the plurality of barcodes to create the plurality of barcoded sample indexing oligonucleotides comprises stochastically barcoding the sample indexing oligonucleotides using a plurality of stochastic barcodes to create a plurality of stochastically barcoded sample indexing oligonucleotides.

In some embodiments, identifying the sample origin of the at least one cell can comprise identifying the presence or absence of the sample indexing sequence of at least one sample indexing oligonucleotide of the plurality of sample indexing compositions. Identifying the presence or absence of the sample indexing sequence can comprise: replicating the at least one sample indexing oligonucleotide to generate a plurality of replicated sample indexing oligonucleotides; obtaining sequencing data of the plurality of replicated sample indexing oligonucleotides; and identifying the sample origin of the cell based on the sample indexing sequence of a replicated sample indexing oligonucleotide of the plurality of sample indexing oligonucleotides that correspond to the least one barcoded sample indexing oligonucleotide in the sequencing data.

In some embodiments, replicating the at least one sample indexing oligonucleotide to generate the plurality of replicated sample indexing oligonucleotides comprises: prior to replicating the at least one barcoded sample indexing oligonucleotide, ligating a replicating adaptor to the at least one barcoded sample indexing oligonucleotide. Replicating the at least one barcoded sample indexing oligonucleotide can comprise replicating the at least one barcoded sample indexing oligonucleotide using the replicating adaptor ligated to the at least one barcoded sample indexing oligonucleotide to generate the plurality of replicated sample indexing oligonucleotides.

In some embodiments, replicating the at least one sample indexing oligonucleotide to generate the plurality of replicated sample indexing oligonucleotides comprises: prior to replicating the at least one barcoded sample indexing oligonucleotide, contacting a capture probe with the at least one sample indexing oligonucleotide to generate a capture probe hybridized to the sample indexing oligonucleotide; and extending the capture probe hybridized to the sample indexing oligonucleotide to generate a sample indexing oligonucleotide associated with the capture probe. Replicating the at least one sample indexing oligonucleotide can comprise replicating the sample indexing oligonucleotide associated with the capture probe to generate the plurality of replicated sample indexing oligonucleotides.

Cell Overloading and Multiplet Identification

Also disclosed herein include methods, kits and systems for identifying cell overloading and multiplet. Such methods, kits and systems can be used in, or in combination with, any suitable methods, kits and systems disclosed herein, for example the methods, kits and systems for measuring cellular component expression level (such as protein expression level) using cellular component binding reagents associated with oligonucleotides.

Using current cell-loading technology, when about 20000 cells are loaded into a microwell cartridge or array with ~60000 microwells, the number of microwells or droplets with two or more cells (referred to as doublets or multiplets) can be minimal. However, when the number of cells loaded increases, the number of microwells or droplets with multiple cells can increase significantly. For example, when about 50000 cells are loaded into about 60000 microwells of a microwell cartridge or array, the percentage of microwells with multiple cells can be quite high, such as 11-14%. Such loading of high number of cells into microwells can be referred to as cell overloading. However, if the cells are divided into a number of groups (e.g., 5), and cells in each group are labeled with sample indexing oligonucleotides with distinct sample indexing sequences, a cell label (e.g., a cell label of a barcode, such as a stochastic barcode) associated with two or more sample indexing sequences can be identified in sequencing data and removed from subsequent processing. In some embodiments, the cells are divided into a large number of groups (e.g., 10000), and cells in each group are labeled with sample indexing oligonucleotides with distinct sample indexing sequences, a sample label associated with two or more sample indexing sequences can be identified in sequencing data and removed from subsequent processing. In some embodiments, different cells are labeled with cell identification oligonucleotides with distinct cell identification sequences, a cell identification sequence associated with two or more cell identification oligonucleotides can be identified in sequencing data and removed from subsequent processing. Such higher number of cells can be loaded into microwells relative to the number of microwells in a microwell cartridge or array.

Disclosed herein include methods for sample identification. In some embodiments, the method comprises: contacting a first plurality of cells and a second plurality of cells with two sample indexing compositions respectively, wherein each of the first plurality of cells and each of the second plurality of cells comprise one or more cellular components, wherein each of the two sample indexing compositions comprises a cellular component binding reagent associated with a sample indexing oligonucleotide, wherein the cellular component binding reagent is capable of specifically binding to at least one of the one or more cellular components, wherein the sample indexing oligonucleotide comprises a sample indexing sequence, and wherein sample indexing sequences of the two sample indexing compositions comprise different sequences; barcoding the sample indexing oligonucleotides using a plurality of barcodes to create a plurality of barcoded sample indexing oligonucleotides, wherein each of the plurality of barcodes comprises a cell label sequence, a barcode sequence (e.g., a molecular label sequence), and a target-binding region, wherein the barcode sequences of at least two barcodes of the plurality of barcodes comprise different sequences, and wherein at least two barcodes of the plurality of barcodes comprise an identical cell label sequence; obtaining sequencing data of the plurality of barcoded sample indexing oligonucleotides; and identifying one or more cell label sequences that is each associated with two or more sample indexing sequences in the sequencing data obtained; and removing the sequencing data associated with the one or more cell label sequences that is each associated with two or more sample indexing sequences from the sequencing data obtained and/or excluding the sequencing data associated with the one or more cell label sequences that is each associated with two or more sample indexing sequences from subsequent analysis (e.g., single cell mRNA profiling, or whole transcriptome analysis). In some embodiments, the sample indexing oligonucleotide comprises a barcode sequence (e.g., a molecular label sequence), a binding site for a universal primer, or a combination thereof.

For example, the method can be used to load 50000 or more cells (compared to 10000-20000 cells) using sample indexing. Sample indexing can use oligonucleotide-conjugated cellular component binding reagents (e.g., antibodies) or cellular component binding reagents against a cellular component (e.g., a universal protein marker) to label cells from different samples with a unique sample index. When two or more cells from different samples, two or more cells from different populations of cells of a sample, or two or more cells of a sample, are captured in the same microwell or droplet, the combined "cell" (or contents of the two or more cells) can be associated with sample indexing oligonucleotides with different sample indexing sequences (or cell identification oligonucleotides with different cell identification sequences). The number of different populations of cells can be different in different implementations. In some embodiments, the number of different populations can be, or be about, 2, 3, 4, 5, 6, 7, 8, 9, 10, 20, 30, 40, 50, 60, 70, 80, 90, 100, or a number or a range between any two of these values. In some embodiments, the number of different populations can be at least, or be at most, 2, 3, 4, 5, 6, 7, 8, 9, 10, 20, 30, 40, 50, 60, 70, 80, 90, or 100. The number, or the average number, of cells in each population can be different in different implementations. In some embodiments, the number, or the average number, of cells in each population can be, or be about, 1, 2, 3, 4, 5, 6, 7, 8, 9, 10, 20, 30, 40, 50, 60, 70, 80, 90, 100, or a number or a range between any two of these values. In some embodiments, the number, or the average number, of cells in each population can be at least, or be at most, 1, 2, 3, 4, 5, 6, 7, 8, 9, 10, 20, 30, 40, 50, 60, 70, 80, 90, or 100. When the number, or the average number, of cells in each population is sufficiently small (e.g., equal to, or fewer than, 50, 25, 10, 5, 4, 3, 2, or 1 cells per population), the sample indexing composition for cell overloading and multiplet identification can be referred to as cell identification compositions.

Cells of a sample can be divided into multiple populations by aliquoting the cells of the sample into the multiple populations. A "cell" associated with more than one sample indexing sequence in the sequencing data can be identified as a "multiplet" based on two or more sample indexing sequences associated with one cell label sequence (e.g., a cell label sequence of a barcode, such as a stochastic barcode) in the sequencing data. The sequencing data of a combined "cell" is also referred to herein as a multiplet. A multiplet can be a doublet, a triplet, a quartet, a quintet, a sextet, a septet, an octet, a nonet, or any combination thereof. A multiplet can be any n-plet. In some embodiments, n is, or is about, 2, 3, 4, 5, 6, 7, 8, 9, 10, 11, 12, 13, 14, 15, 16, 17, 18, 19, 20, or a range between any two of these values. In some embodiments, n is at least, or is at most, 2, 3, 4, 5, 6, 7, 8, 9, 10, 11, 12, 13, 14, 15, 16, 17, 18, 19, or 20.

When determining expression profiles of single cells, two cells may be identified as one cell and the expression profiles of the two cells may be identified as the expression profile for one cell (referred to as a doublet expression profile). For example, when determining expression profiles of two cells using barcoding (e.g., stochastic barcoding), the mRNA molecules of the two cells may be associated with barcodes having the same cell label. As another example, two cells may be associated with one particle (e.g., a bead). The particle can include barcodes with the same cell label. After lysing the cells, the mRNA molecules in the two cells can be associated with the barcodes of the particle, thus the same cell label. Doublet expression profiles can skew the interpretation of the expression profiles.

A doublet can refer to a combined "cell" associated with two sample indexing oligonucleotides with different sample indexing sequences. A doublet can also refer to a combined "cell" associated with sample indexing oligonucleotides with two sample indexing sequences. A doublet can occur when two cells associated with two sample indexing oligonucleotides of different sequences (or two or more cells associated with sample indexing oligonucleotides with two different sample indexing sequences) are captured in the same microwell or droplet, the combined "cell" can be associated with two sample indexing oligonucleotides with different sample indexing sequences. A triplet can refer to a combined "cell" associated with three sample indexing oligonucleotides all with different sample indexing sequences, or a combined "cell" associated with sample indexing oligonucleotides with three different sample indexing sequences. A quartet can refer to a combined "cell" associated with four sample indexing oligonucleotides all with different sample indexing sequences, or a combined "cell" associated with sample indexing oligonucleotides with four different sample indexing sequences. A quintet can refer to a combined "cell" associated with five sample indexing oligonucleotides all with different sample indexing sequences, or a combined "cell" associated with sample indexing oligonucleotides with five different sample indexing sequences. A sextet can refer to a combined "cell" associated with six sample indexing oligonucleotides all with different sample indexing sequences, or a combined "cell" associated with sample indexing oligonucleotides with six different sample indexing sequences. A septet can refer to a combined "cell" associated with seven sample indexing oligonucleotides all with different sample indexing sequences, or a combined "cell" associated with sample indexing oligonucleotides with seven different sample indexing sequences. A octet can refer to a combined "cell" associated with eight sample indexing oligonucleotides all with different sample indexing sequences, or a combined "cell" associated with sample indexing oligonucleotides with eight different sample indexing sequences. A nonet can refer to a combined "cell" associated with nine sample indexing oligonucleotides all with different sample indexing sequences, or a combined "cell" associated with sample indexing oligonucleotides with nine different sample indexing sequences. A multiplet can occur when two or more cells associated with two or more sample indexing oligonucleotides of different sequences (or two or more cells associated with sample indexing oligonucleotides with two or more different sample indexing sequences) are captured in the same microwell or droplet, the combined "cell" can be associated with sample indexing oligonucleotides with two or more different sample indexing sequences.

As another example, the method can be used for multiplet identification, whether in the context of sample overloading or in the context of loading cells onto microwells of a microwell array or generating droplets containing cells. When two or more cells are loaded into one microwell, the resulting data from the combined "cell" (or contents of the two or more cells) is a multiplet with aberrant gene expression profile. By using sample indexing, one can recognize some of these multiplets by looking for cell labels that are each associated with or assigned to two or more sample indexing oligonucleotides with different sample indexing sequences (or sample indexing oligonucleotides with two or more sample indexing sequences). With sample indexing sequence, the methods disclosed herein can be used for multiplet identification (whether in the context of sample overloading or not, or in the context of loading cells onto microwells of a microwell array or generating droplets containing cells). In some embodiments, the method comprises: contacting a first plurality of cells and a second plurality of cells with two sample indexing compositions respectively, wherein each of the first plurality of cells and each of the second plurality of cells comprise one or more cellular components, wherein each of the two sample indexing compositions comprises a cellular component binding reagent associated with a sample indexing oligonucleotide, wherein the cellular component binding reagent is capable of specifically binding to at least one of the one or more cellular components, wherein the sample indexing oligonucleotide comprises a sample indexing sequence, and wherein sample indexing sequences of the two sample indexing compositions comprise different sequences; barcoding the sample indexing oligonucleotides using a plurality of barcodes to create a plurality of barcoded sample indexing oligonucleotides, wherein each of the plurality of barcodes comprises a cell label sequence, a barcode sequence (e.g., a molecular label sequence), and a target-binding region, wherein barcode sequences of at least two barcodes of the plurality of barcodes comprise different sequences, and wherein at least two barcodes of the plurality of barcodes comprise an identical cell label sequence; obtaining sequencing data of the plurality of barcoded sample indexing oligonucleotides; and identifying one or more multiplet cell label sequences that is each associated with two or more sample indexing sequences in the sequencing data obtained.

The number of cells that can be loaded onto microwells of a microwell cartridge or into droplets generated using a microfluidics device can be limited by the multiplet rate. Loading more cells can result in more multiplets, which can be hard to identify and create noise in the single cell data. With sample indexing, the method can be used to more accurately label or identify multiplets and remove the multiplets from the sequencing data or subsequent analysis. Being able to identify multiplets with higher confidence can increase user tolerance for the multiplet rate and load more cells onto each microwell cartridge or generating droplets with at least one cell each.

In some embodiments, contacting the first plurality of cells and the second plurality of cells with the two sample indexing compositions respectively comprises: contacting the first plurality of cells with a first sample indexing compositions of the two sample indexing compositions; and contacting the first plurality of cells with a second sample indexing compositions of the two sample indexing compositions. The number of pluralities of cells and the number of pluralities of sample indexing compositions can be different in different implementations. In some embodiments, the number of pluralities of cells and/or sample indexing compositions can be, or be about, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number of pluralities of cells and/or sample indexing compositions can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000. The number of cells can be different in different implementations. In some embodiments, the number, or the average number, of cells can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number, or the average number, or cells can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000.

In some embodiments, the method comprises: removing unbound sample indexing compositions of the two sample indexing compositions. Removing the unbound sample indexing compositions can comprise washing cells of the first plurality of cells and the second plurality of cells with a washing buffer. Removing the unbound sample indexing compositions can comprise selecting cells bound to at least one cellular component binding reagent of the two sample indexing compositions using flow cytometry. In some embodiments, the method comprises: lysing the one or more cells from each of the plurality of samples.

In some embodiments, the sample indexing oligonucleotide is configured to be (or can be) detachable or non-detachable from the cellular component binding reagent. The method can comprise detaching the sample indexing oligonucleotide from the cellular component binding reagent. Detaching the sample indexing oligonucleotide can comprise detaching the sample indexing oligonucleotide from the cellular component binding reagent by UV photocleaving, chemical treatment (e.g., using reducing reagent, such as dithiothreitol), heating, enzyme treatment, or any combination thereof.

In some embodiments, barcoding the sample indexing oligonucleotides using the plurality of barcodes comprises: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

In some embodiments, the method comprises: amplifying the plurality of barcoded sample indexing oligonucleotides to produce a plurality of amplicons. Amplifying the plurality of barcoded sample indexing oligonucleotides can comprise amplifying, using polymerase chain reaction (PCR), at least a portion of barcode sequence (e.g., the molecular label sequence) and at least a portion of the sample indexing oligonucleotide. In some embodiments, obtaining the sequencing data of the plurality of barcoded sample indexing oligonucleotides can comprise obtaining sequencing data of the plurality of amplicons. Obtaining the sequencing data comprises sequencing at least a portion of the barcode sequence and at least a portion of the sample indexing oligonucleotide. In some embodiments, identifying the sample origin of the at least one cell comprises identifying sample origin of the plurality of barcoded targets based on the sample indexing sequence of the at least one barcoded sample indexing oligonucleotide.

In some embodiments, barcoding the sample indexing oligonucleotides using the plurality of barcodes to create the plurality of barcoded sample indexing oligonucleotides comprises stochastically barcoding the sample indexing oligonucleotides using a plurality of stochastic barcodes to create a plurality of stochastically barcoded sample indexing oligonucleotides.

In some embodiments, the method includes: barcoding a plurality of targets of the cell using the plurality of barcodes to create a plurality of barcoded targets, wherein each of the plurality of barcodes comprises a cell label sequence, and wherein at least two barcodes of the plurality of barcodes comprise an identical cell label sequence; and obtaining sequencing data of the barcoded targets. Barcoding the plurality of targets using the plurality of barcodes to create the plurality of barcoded targets can include: contacting copies of the targets with target-binding regions of the barcodes; and reverse transcribing the plurality targets using the plurality of barcodes to create a plurality of reverse transcribed targets.

In some embodiments, the method comprises: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using a plurality of stochastic barcodes to create a plurality of stochastically barcoded targets.

In some embodiments, the method for cell identification comprise: contacting a first plurality of one or more cells and a second plurality of one or more cells with two cell identification compositions respectively, wherein each of the first plurality of one or more cells and each of the second plurality of one or more cells comprise one or more cellular components, wherein each of the two cell identification compositions comprises a cellular component binding reagent associated with a cell identification oligonucleotide, wherein the cellular component binding reagent is capable of specifically binding to at least one of the one or more cellular components, wherein the cell identification oligonucleotide comprises a cell identification sequence, and wherein cell identification sequences of the two cell identification compositions comprise different sequences; barcoding the cell identification oligonucleotides using a plurality of barcodes to create a plurality of barcoded cell identification oligonucleotides, wherein each of the plurality of barcodes comprises a cell label sequence, a barcode sequence (e.g., a molecular label sequence), and a target-binding region, wherein the barcode sequences of at least two barcodes of the plurality of barcodes comprise different sequences, and wherein at least two barcodes of the plurality of barcodes comprise an identical cell label sequence; obtaining sequencing data of the plurality of barcoded cell identification oligonucleotides; and identifying one or more cell label sequences that is each associated with two or more cell identification sequences in the sequencing data obtained; and removing the sequencing data associated with the one or more cell label sequences that is each associated with two or more cell identification sequences from the sequencing data obtained and/or excluding the sequencing data associated with the one or more cell label sequences that is each associated with two or more cell identification sequences from subsequent analysis (e.g., single cell mRNA profiling, or whole transcriptome analysis). In some embodiments, the cell identification oligonucleotide comprises a barcode sequence (e.g., a molecular label sequence), a binding site for a universal primer, or a combination thereof.

A multiplet (e.g., a doublet, triplet, etc.) can occur when two or more cells associated with two or more cell identification oligonucleotides of different sequences (or two or more cells associated with cell identification oligonucleotides with two or more different cell identification sequences) are captured in the same microwell or droplet, the combined "cell" can be associated with cell identification oligonucleotides with two or more different cell identification sequences.

Cell identification compositions can be used for multiplet identification, whether in the context of cell overloading or in the context of loading cells onto microwells of a microwell array or generating droplets containing cells. When two or more cells are loaded into one microwell, the resulting data from the combined "cell" (or contents of the two or more cells) is a multiplet with aberrant gene expression profile. By using cell identification, one can recognize some of these multiplets by looking for cell labels (e.g., cell labels of barcodes, such as stochastic barcodes) that are each associated with or assigned to two or more cell identification oligonucleotides with different cell identification sequences (or cell identification oligonucleotides with two or more cell identification sequences). With cell identification sequence, the methods disclosed herein can be used for multiplet identification (whether in the context of sample overloading or not, or in the context of loading cells onto microwells of a microwell array or generating droplets containing cells). In some embodiments, the method comprises: contacting a first plurality of one or more cells and a second plurality of one or more cells with two cell identification compositions respectively, wherein each of the first plurality of one or more cells and each of the second plurality of one or more cells comprise one or more cellular components, wherein each of the two cell identification compositions comprises a cellular component binding reagent associated with a cell identification oligonucleotide, wherein the cellular component binding reagent is capable of specifically binding to at least one of the one or more cellular components, wherein the cell identification oligonucleotide comprises a cell identification sequence, and wherein cell identification sequences of the two cell identification compositions comprise different sequences; barcoding the cell identification oligonucleotides using a plurality of barcodes to create a plurality of barcoded cell identification oligonucleotides, wherein each of the plurality of barcodes comprises a cell label sequence, a barcode sequence (e.g., a molecular label sequence), and a target-binding region, wherein barcode sequences of at least two barcodes of the plurality of barcodes comprise different sequences, and wherein at least two barcodes of the plurality of barcodes comprise an identical cell label sequence; obtaining sequencing data of the plurality of barcoded cell identification oligonucleotides; and identifying one or more multiplet cell label sequences that is each associated with two or more cell identification sequences in the sequencing data obtained.

The number of cells that can be loaded onto microwells of a microwell cartridge or into droplets generated using a microfluidics device can be limited by the multiplet rate. Loading more cells can result in more multiplets, which can be hard to identify and create noise in the single cell data. With cell identification, the method can be used to more accurately label or identify multiplets and remove the multiplets from the sequencing data or subsequent analysis. Being able to identify multiplets with higher confidence can increase user tolerance for the multiplet rate and load more cells onto each microwell cartridge or generating droplets with at least one cell each.

In some embodiments, contacting the first plurality of one or more cells and the second plurality of one or more cells with the two cell identification compositions respectively comprises: contacting the first plurality of one or more cells with a first cell identification compositions of the two cell identification compositions; and contacting the first plurality of one or more cells with a second cell identification compositions of the two cell identification compositions. The number of pluralities of cell identification compositions can be different in different implementations. In some embodiments, the number of cell identification compositions can be, or be about, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number of cell identification compositions can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000. The number, or average number, of cells in each plurality of one or more cells can be different in different implementations. In some embodiments, the number, or average number, of cells in each plurality of one or more cells can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number, or average number, of cells in each plurality of one or more cells can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000.

In some embodiments, the method comprises: removing unbound cell identification compositions of the two cell identification compositions. Removing the unbound cell identification compositions can comprise washing cells of the first plurality of one or more cells and the second plurality of one or more cells with a washing buffer. Removing the unbound cell identification compositions can comprise selecting cells bound to at least one cellular component binding reagent of the two cell identification compositions using flow cytometry. In some embodiments, the method comprises: lysing the one or more cells from each of the plurality of samples.

In some embodiments, the cell identification oligonucleotide is configured to be (or can be) detachable or non-detachable from the cellular component binding reagent. The method can comprise detaching the cell identification oligonucleotide from the cellular component binding reagent. Detaching the cell identification oligonucleotide can comprise detaching the cell identification oligonucleotide from the cellular component binding reagent by UV photocleaving, chemical treatment (e.g., using reducing reagent, such as dithiothreitol), heating, enzyme treatment, or any combination thereof.

In some embodiments, barcoding the cell identification oligonucleotides using the plurality of barcodes comprises: contacting the plurality of barcodes with the cell identification oligonucleotides to generate barcodes hybridized to the cell identification oligonucleotides; and extending the barcodes hybridized to the cell identification oligonucleotides to generate the plurality of barcoded cell identification oligonucleotides. Extending the barcodes can comprise extending the barcodes using a DNA polymerase to generate the plurality of barcoded cell identification oligonucleotides. Extending the barcodes can comprise extending the barcodes using a reverse transcriptase to generate the plurality of barcoded cell identification oligonucleotides.

In some embodiments, the method comprises: amplifying the plurality of barcoded cell identification oligonucleotides to produce a plurality of amplicons. Amplifying the plurality of barcoded cell identification oligonucleotides can comprise amplifying, using polymerase chain reaction (PCR), at least a portion of barcode sequence (e.g., the molecular label sequence) and at least a portion of the cell identification oligonucleotide. In some embodiments, obtaining the sequencing data of the plurality of barcoded cell identification oligonucleotides can comprise obtaining sequencing data of the plurality of amplicons. Obtaining the sequencing data comprises sequencing at least a portion of the barcode sequence and at least a portion of the cell identification oligonucleotide. In some embodiments, identifying the sample origin of the at least one cell comprises identifying sample origin of the plurality of barcoded targets based on the cell identification sequence of the at least one barcoded cell identification oligonucleotide.

In some embodiments, barcoding the cell identification oligonucleotides using the plurality of barcodes to create the plurality of barcoded cell identification oligonucleotides comprises stochastically barcoding the cell identification oligonucleotides using a plurality of stochastic barcodes to create a plurality of stochastically barcoded cell identification oligonucleotides.

Quantitative Analysis of a Plurality of Cellular Component Targets of Cells of Interest Disclosed herein include methods of quantitative analysis of a plurality of cellular component targets of cells of interest. In some embodiments, the method comprises: contacting a plurality of cellular component-binding reagents with a plurality of cells of a sample, each cell comprising cellular component targets of a plurality of cellular component targets, for specific binding with the plurality of cellular component targets, wherein each of the plurality of cellular component-binding reagents is associated with a cellular component-binding reagent specific oligonucleotide comprising a detectable moiety and an identifier sequence for the cellular component-binding reagent that the cellular component-binding reagent specific oligonucleotide is associated therewith, and wherein the cellular component-binding reagent is capable of specifically binding to a cellular component target of the plurality of cellular component targets, thereby generating cells of the plurality of cells each associated with cellular component-binding reagents. The method can comprise obtaining cells of interest from the plurality of cells based on the detectable moieties of the cellular component-binding reagent specific oligonucleotides associated with the cellular component-binding reagents, or lack thereof. The method can comprise contacting a plurality of barcodes with the cellular component-binding reagent specific oligonucleotides, or products thereof, associated with the cellular component-binding reagents associated with the cells of interest obtained, wherein each of the plurality of barcodes comprises a target binding region and a molecular label sequence to generate barcodes hybridized to the cellular component-binding reagent specific oligonucleotides, or products thereof. The method can comprise extending the barcodes hybridized to the cellular component-binding reagent specific oligonucleotides to produce a plurality of labeled nucleic acids, wherein each of the labeled nucleic acid comprises an identifier sequence, or a complementary sequence thereof, and a molecular label sequence, or a complementary sequence thereof; The method can comprise obtaining sequence information of the plurality of labeled nucleic acids, complementary sequences thereof, portions thereof, or a combination thereof, to determine the number of copies of each of the cellular component targets of the cellular component-binding reagents associated with each of the cells of interest.

In some embodiments, the plurality of cells comprises T cells, B cells, tumor cells, myeloid cells, blood cells, normal cells, fetal cells, maternal cells, or a mixture thereof. In some embodiments, the plurality of cellular component targets comprises a cell-surface protein, an intracellular protein, a cell marker, a B-cell receptor, a T-cell receptor, an antibody, a major histocompatibility complex, a tumor antigen, a receptor, or a combination thereof. In some embodiments, the methods comprise after contacting the plurality of cellular component-binding reagents with the plurality of cells, removing one or more cellular component-binding reagents of the plurality of cellular component-binding reagents that are not contacted with the plurality of cells. In some embodiments, removing the one or more cellular component-binding reagents not contacted with the plurality of cells comprises: removing the one or more cellular component-binding reagents not contacted with the respective at least one of the plurality of cellular component targets.

In some embodiments, obtaining the cells of interest comprises obtaining the cells of interest based on the detectable moieties (e.g., fluorescent moieties, phosphorescent moieties) of the cellular component-binding reagent specific oligonucleotides associated with the cellular component-binding reagents, or lack thereof. In some embodiments, obtaining the cells of interest comprises obtaining the cells of interest flow cytometrically based on the detectable moieties of the cellular component-binding reagent specific oligonucleotides associated with the cellular component-binding reagents, or lack thereof. In some embodiments, obtaining the cells of interest flow cytometrically based on the detectable moieties of the cellular component-binding reagent specific oligonucleotides associated with the cellular component-binding reagents, or lack thereof, increases the concentration of cells of interest by, by about, by at least 10%, 20%, 30%, 40%, 50%, 60%, 70%, 80%, 90%, 100%, 110%, 120%, 130%, 140%, 150%, 160%, 170%, 180%, 190%, 200%, 300%, 400%, 500%, 600%, 700%, 800%, 900%, 1000% or a number or range between any two of these values. In some embodiments, obtaining the cells of interest flow cytometrically based on the detectable moieties of the cellular component-binding reagent specific oligonucleotides associated with the cellular component-binding reagents, or lack thereof, improves the efficiency of analysis (e.g., single cell analysis, including obtaining sequencing data of cells of interest of a sample, not all cells of a sample) by, by about, by at least, 2-folds, 3-folds, 4-folds, 5-folds, 6-folds, 7-folds, 8-folds, 9-folds, 10-folds, 20-folds, 30-folds, 40-folds, 50-folds, 60-folds, 70-folds, 80-folds, 90-folds, 100-folds, 120-folds, 130-folds, 140-folds, 150-folds, 160-folds, 170-folds, 180-folds, 190-folds, 200-folds, 300-folds, 400-folds, 500-folds, 600-folds, 700-folds, or a number or a range between any two of these values. In some embodiments, the concentration of the cell of interest in the sample is increased by at least, or at least about 2-folds, 3-folds, 4-folds, 5-folds, 6-folds, 7-folds, 8-folds, 9-folds, 10-folds, 50-folds, 100-folds, 250-folds, 500-folds, 750-folds, 1000-folds, 5000-folds, 10000-folds, 50000-folds, 100000-folds, 500000-folds, 1000000-folds, or a number or a range between any two of these values, after obtaining the cells of interest flow cytometrically based on the detectable moieties of the cellular component-binding reagent specific oligonucleotides associated with the cellular component-binding reagents, or lack thereof. In some embodiments, the concentration of the cell of interest in the sample is increased by, or by about, 2-folds, 3-folds, 4-folds, 5-folds, 6-folds, 7-folds, 8-folds, 9-folds, 10-folds, 50-folds, 100-folds, 250-folds, 500-folds, 750-folds, 1000-folds, 5000-folds, 10000-folds, 50000-folds, 100000-folds, 500000-folds, 1000000-folds, or a number or a range between any these two values, after obtaining the cells of interest flow cytometrically based on the detectable moieties of the cellular component-binding reagent specific oligonucleotides associated with the cellular component-binding reagents, or lack thereof.

In some embodiments, obtaining the cells of interest flow cytometrically based on the detectable moieties of the cellular component-binding reagent specific oligonucleotides associated with the cellular component-binding reagents, or lack thereof, enriches the sample (e.g., depletes cells not of interest, interfering cells, and debris). According to some embodiments, depletion of cells not of interest, interfering cells, and debris can remove at least 1%, 2%, 3%, 4%, 5%, 6%, 7%, 8%, 9%, 10%, 20%, 30%, 40%, 50%, 60%, 70%, 80%, 90%, 95%, 99%, 99.5%, 99.9%, or a number or a range between any two of these values, of the cells not of interest, interfering cells, and/or debris originally present in the sample. In some embodiments, at least 10%, 20%, 30%, 40%, 50%, 60%, 70%, 80%, 90%, 91%, 92%, 93%, 94%, 95%, 96%, 97%, 98%, 99%, 99.5%, 99.9%, 99.95%, 99.99%, 99.995%, 99.999%, or a number or a range between any two of these values, of the solid mass in the sample after depletion is the cells of interest. In some embodiments, 10%, 20%, 30%, 40%, 50%, 60%, 70%, 80%, 90%, 91%, 92%, 93%, 94%, 95%, 96%, 97%, 98%, 99%, 99.5%, 99.9%, 99.95%, 99.99%, 99.995%, 99.999%, or a number or a range between any two of these values, of the solid mass in the sample after depletion is the cells of interest.

The methods disclosed herein can be applicable to samples with low concentration of cells of interest, for example samples with cells of interest. Cells of interest can be rare. In some embodiments, cells of interest are cells that account for less than 0.0001%, 0.0005%, 0.001%, 0.005%, 0.01%, 0.1%, 0.5%, 1%, 2%, 3%, 4%, 5%, 6%, 7%, 8%, 9%, 10%, or a number or a range between any two of these values, of the total number of cells in a sample. In some embodiments, the sample is a fluid sample having no more than 1, 2, 3, 4, 5, 6, 7, 8, 9, 10, 15, 20, 25, 50, 100, 250, 500, 1000, or a number or a range between any two of these values, cells of interest per milliliter of the sample. The fluid sample can comprise, or be, blood (e.g., whole blood, serum, or plasma), urine, saliva, cerebrospinal fluid, pleural fluid, amniotic fluid, semen, or any combination thereof. In some embodiments, cells of interest are, or are about 1 in 10, $10^2$, $10^3$, $10^4$, $10^5$, $10^6$, $10^7$, $10^8$, $10^9$, $10^{10}$, $10^{11}$, $10^{12}$, $10^{13}$, $10^{15}$, $10^{20}$, or a number or a range between any two of these values, of total cells in the sample or per milliliter of the fluid sample. The size of cells of interest can vary. For example, the diameter of the cells of interest can be about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 micrometers, or a number or a range between any two of these values.

As used herein, the term "cells of interest" refer to cells being studied. Because cells of interest can be rare and the concentration of cells of interest in the sample can be low, the enrichment of cells of interest can be advantageous in order to speed up the isolation of cells of interest using, for example, the detectable moieties of the cellular component-binding reagent specific oligonucleotides associated with the cellular component-binding reagents, or lack thereof. In some embodiments, cells of interest can also be enriched using focusing, such as acoustic focusing, and magnetic depletion of cells not of interest and interfering cells and debris. Non-limiting examples of cells of interest in samples include cells expressing a malignant phenotype; tumor cells, such as tumor cells which have been shed from tumor into blood or other bodily fluids or bone marrow; benign tumor cells; cancer cells; cancer cells in peripheral blood; thyroid cancer cells; breast cancer cells; circulating tumor cells ("CTCs"); leukemia cells; cancer stem cells; single cells from different cell cycle phases (G0/G1, S, G2); sperms bearing X and Y chromosomes; stem cells; fetal or adult stem cells; multipotent stem cells; nucleated red blood cells ("NRBC") in Thalassemia patients; fetal cells, such as fetal cells in maternal peripheral blood; fetal nucleated red blood cells ("FNRBC") in the maternal circulation; and cells characterized by CD71, CD8, CD34, or CD133. Other examples of cells of interest include, but are not limited to, the following cells: circulating endothelial cells; cells infected with a virus, such as cells infected by HIV, cells transfected with a gene of interest; and aberrant subtypes of T-cells or B-cells present in the peripheral blood of subjects afflicted with autoimmune or autoreactive disorders; activated lymphocytes; antigen presenting cells such as monocytes and dendritic cells; pathogenic or parasitic organisms, cells containing intracellular parasites; and cells or microorganisms in dilute fluids like urine.

In some embodiments, the sample comprises a tissue section, or cells thereof. The type of the sample is not limited. For example, the sample can be, or comprise, a clinical sample, a biological sample, an environmental sample, or a combination thereof. For example, the sample can include one or more of a biological fluid, tissue and cell from a patient. In some embodiments, the sample can include blood, urine, cerebrospinal fluid, pleural fluid, amniotic fluid, semen, saliva, bone marrow, a biopsy sample, or a combination thereof. Samples can comprise cells from a mixed cancer cell sample.

The methods, compositions, kits, devices, and systems disclosed herein may be used for a variety of applications in basic research, biomedical research, environmental testing, and clinical diagnostics. Examples of potential applications for the disclosed methods of quantitative analysis of a plurality of cellular component targets of cells of interest include, but are not limited to, genotyping, gene expression profiling, detection and identification of rare cells, diagnosis of a disease or condition, determining prognosis for a disease or condition, determining a course of treatment for a disease (e.g., determining if a patient may respond to a therapy) or condition, and monitoring the response to treatment for a disease or condition, and understanding biological development processes. In some embodiments, the methods, devices, and systems of the disclosure can be used for characterizing circulating tumor cells (CTCs). The methods, devices, and systems of the disclosure can be used for detecting the expression profile in circulating tumor cells from an enriched blood sample. The method can comprise obtaining a biological sample containing a mixed population of cells from an individual suspected of having target rare cells, contacting said sample (which may be enriched) to the devices and systems of the disclosure such that a single cell is in a single well. The sample can be subjected to methods for removal of red blood cells and/or dead cells from blood. The sample can be contacted with beads of the disclosure such that a single bead is in a single well with a single cell. The cell can be lysed. The bead can comprise a stochastic label that can bind to a specific location genes in the cell and/or mRNAs of the cell. The molecules from the CTC associated with solid support can be subjected to the molecular biology methods of the disclosure, including reverse transcription, amplification, and sequencing. Cells can be clustered based on the gene expression profile of the cells, thereby identifying rare cells (e.g., CTCs) and subpopulations of rare cells (e.g., CTCs) based on their genotypes. The methods can be used for identifying and characterizing subpopulations (subgroups) of circulating tumor cells (CTCs) in a population of CTCs or a sample, quantifying subgroups of CTCs in the population of CTCs or the sample, diagnosing and monitoring of cancer, treatment and prognosis, in particular for solid tumors, and using the identified CTC subgroups as biomarkers for diagnosis, prognosis and therapeutic treatment. In one example, the methods of the disclosure (e.g., immunological methods of the disclosure) can be used to characterize tumor infiltrating lymphocytes in a tumor, monitoring clinical response of a patient with a tumor before and after treatment, and determining the minimal residual disease (e.g., left over cancer cells) after treatment.

Analyzing a Plurality of Cellular Component Targets in a Sample

Disclosed herein include methods of analyzing a plurality of cellular component targets in a sample. In some embodiments, the method comprises: contacting a plurality of cellular component-binding reagents with a plurality of cells of a sample, each cell comprising cellular component targets of a plurality of cellular component targets, for specific binding with the plurality of cellular component targets, wherein each of the plurality of cellular component-binding reagents is associated with a cellular component-binding reagent specific oligonucleotide comprising a detectable moiety, or a precursor thereof, and an identifier sequence for the cellular component-binding reagent that the cellular component-binding reagent specific oligonucleotide is associated therewith, and wherein the cellular component-binding reagent is capable of specifically binding to a cellular component target of the plurality of cellular component targets, thereby generating cells of the plurality of cells each associated with the cellular component-binding reagents. The method can comprise performing an experiment on the plurality of cells using the moieties of the cellular component-binding reagent specific oligonucleotides associated with the cellular component-binding reagents, or lack thereof, to obtain an experiment result. The method can comprise contacting a plurality of barcodes with the cellular component-binding reagent specific oligonucleotides, or products thereof, associated with the cellular component-binding reagents associated with the cells, wherein each of the plurality of barcodes comprises a target binding region and a molecular label sequence to generate barcodes hybridized to the cellular component-binding reagent specific oligonucleotides, or products thereof. The method can comprise extending the barcodes hybridized to the cellular component-binding reagent specific oligonucleotides to produce a plurality of labeled nucleic acids, wherein each of the labeled nucleic acid comprises an identifier sequence, or a complementary sequence thereof, and a molecular label sequence, or a complementary sequence thereof. The method can comprise obtaining sequence information of the plurality of labeled nucleic acids, complementary sequences thereof, portions thereof, or a combination thereof, to determine the number of copies of each of the cellular component targets of the cellular component-binding reagents associated with the cells generated. The method can comprise performing an analysis of the experiment result of the cells and the number of copies of each of the cellular component targets of the cells associated with the cellular component-binding reagents. In some embodiments, performing the analysis comprises correlating the experiment result of the cells and the number of copies of each of the cellular component targets of the cells associated with the cellular component-binding reagents. The method can comprise performing an analysis of the number of copies of each of the cellular component targets of the cells associated with the cellular component-binding reagents based on the experiment result of the cells. The method can comprise performing an analysis of the number of copies of each of the cellular component targets of the cells associated with the cellular component-binding reagents based on the experiment result of the cells.

Disclosed herein include methods of analyzing a plurality of cellular component targets in a sample. In some embodiments, the method comprises: contacting a plurality of cellular component-binding reagents with a plurality of cells of a sample, each cell comprising cellular component targets of a plurality of cellular component targets, for specific binding with the plurality of cellular component targets, wherein each of the plurality of cellular component-binding reagents is associated with a cellular component-binding reagent specific oligonucleotide comprising a detectable moiety, or a precursor thereof, and an identifier sequence for the cellular component-binding reagent that the cellular component-binding reagent specific oligonucleotide is associated therewith, and wherein the cellular component-binding reagent is capable of specifically binding to a cellular component target of the plurality of cellular component targets, thereby generating cells of the plurality of cells each associated with the cellular component-binding reagents. The method can comprise performing an experiment on the plurality of cells using the moieties of the cellular component-binding reagent specific oligonucleotides associated with the cellular component-binding reagents, or lack thereof, to obtain an experiment result. The method can comprise selecting cells of interest from the cells associated with the cellular component-binding reagents based on the experiment result. The method can comprise contacting a plurality of barcodes with the cellular component-binding reagent specific oligonucleotides, or products thereof, associated with the cellular component-binding reagents associated with the cells of interest, wherein each of the plurality of barcodes comprises a target binding region and a molecular label sequence to generate barcodes hybridized to the cellular component-binding reagent specific oligonucleotides, or products thereof. The method can comprise extending the barcodes hybridized to the cellular component-binding reagent specific oligonucleotides to produce a plurality of labeled nucleic acids, wherein each of the labeled nucleic acid comprises an identifier sequence, or a complementary sequence thereof, and a molecular label sequence, or a complementary sequence thereof. The method can comprise obtaining sequence information of the plurality of labeled nucleic acids, complementary sequences thereof, portions thereof, or a combination thereof, to determine the number of copies of each of the cellular component targets of the cellular component-binding reagents associated with the cells of interest.

In some embodiments, performing the experiment comprises performing a microscopy observation of the cells associated with the cellular component-binding reagents using the detectable moieties of the cellular component-binding reagent specific oligonucleotides associated with the cellular component-binding reagents, or lack thereof. In some embodiments, performing the microscopy observation comprises imaging the cells associated with the cellular component-binding reagents using the detectable moieties of the cellular component-binding reagent specific oligonucleotides associated with the cellular component-binding reagents, or lack thereof. In some embodiments, imaging the cells comprises live imaging the cells associated with the cellular component-binding reagents using the detectable moieties of the cellular component-binding reagent specific oligonucleotides associated with the cellular component-binding reagents, or lack thereof.

In some embodiments, the sample is imaged. In some embodiments, the imaged sample comprises cells associated with cellular component-binding reagents associated with a cellular component-binding reagent specific oligonucleotide comprising a detectable moiety. An image of specifically bound cellular component-binding reagents associated with a cellular component-binding reagent specific oligonucleotide may be generated by, for example, fluorescent imaging. In some embodiments, imaging comprises live imaging. Imaging can comprise microscopy such as bright field imaging, oblique illumination, dark field imaging, dispersion staining, phase contrast, differential interference contrast, interference reflection microscopy, fluorescence, confocal, electron microscopy, transmission electron microscopy, scanning electron microscopy, and single plane illumination, or any combination thereof. Imaging can comprise the use of a negative stain (e.g., nigrosin, ammonium molybdate, uranyl acetate, uranyl formate, phosphotungstic acid, osmium tetroxide). Imaging can comprise the use of heavy metals (e.g., gold, osmium) that can scatter electrons.

Imaging can comprise imaging a portion of the sample (e.g., slide/array). Imaging can comprise imaging at least 10, 20, 30, 40, 50, 60, 70, 80, 90, or 100% of the sample. Imaging can comprise imaging at most 10, 20, 30, 40, 50, 60, 70, 80, 90, or 100% of the sample. Imaging can be done in discrete steps (e.g., the image may not need to be contiguous). Imaging can comprise taking at least 1, 2, 3, 4, 5, 6, 7, 8, 9, or 10 or more different images. Imaging can comprise taking at most 1, 2, 3, 4, 5, 6, 7, 8, 9, or 10 or more different images.

Cells associated with cellular component-binding reagents disclosed herein can be placed on a substrate on a known way and can be imaged. The image can be used to determine the relative level of the cellular component targets of interest based on the intensity of the detectable signal (e.g., fluorescent signal). Scanning laser fluorescence microscopes or readers can be used to acquire digital images of the emitted light from substrate (e.g., microarray). A focused light source (usually a laser) can be scanned across the substrate causing cells associated with cellular component-binding reagents disclosed herein to emit an optical signal, such as fluorescence. The fluorophore-specific fluorescence data can be collected and measured during the scanning operation, and then an image of the substrate can be reconstructed via appropriate algorithms, software and computer hardware. The substrate can be imaged with a confocal laser scanner. The scanner can scan the substrate to produce one image for each detectable moiety used by sequentially scanning the substrate with a laser of a proper wavelength for the particular detectable moiety. Each detectable moiety can have a known excitation spectra and a known emission spectra. The scanner can include a beam splitter which reflects a laser beam towards an objective lens which, in turn, focuses the beam at the surface of slide to cause fluorescence spherical emission. A portion of the emission can travel back through the lens and the beam splitter. After traveling through the beam splitter, the fluorescence beam can be reflected by a mirror, travels through an emission filter, a focusing detector lens and a central pinhole.

By correlating the image showing the locations of the cellular component target with an image of the sample, the spatial barcode of the cellular component target may be generated. The data from the substrate scan can be correlated to the image of the un-lysed sample on the substrate. The data can be overlaid thereby generating a map. The disclosure also provides for methods for estimating the number and position of cellular component targets with cellular component-binding reagents associated with a cellular component-binding reagent specific oligonucleotide comprising a detectable moiety and/or stochastic barcoding and digital counting. The data obtained from the methods of the disclosure can be visualized on a map. The data obtained from the methods of the disclosure can be visualized on a map of the microwell array (e.g., such that the results of each sample can be traced to a location in the microwell array). A map of the number and location of cellular component targets from a sample can be constructed using information generated using the methods described herein. The map can be used to locate a physical location of a cellular component target. The map can be used to identify the location of multiple cellular component targets. The multiple cellular component targets can be the same species of target, or the multiple targets can be multiple different targets. The map can be generated from data from a single sample. The map can be constructed using data from multiple samples, thereby generating a combined map. The map can be constructed with data from tens, hundreds, and/or thousands of samples. A map constructed from multiple samples can show a distribution of digital counts of targets associated with regions common to the multiple samples.

The data analysis and correlation can be useful for determining the presence and/or absence of a specific cell type (e.g., rare cell, cancer cell, bacterial cell). The data correlation can be useful for determining the relative ratios of target nucleic acids and/or cellular component targets in distinct locations either within a cell, or within a sample. The methods and compositions disclosed herein can be companion diagnostics for a medical professional (e.g., a pathologist) wherein a subject can be diagnosed by visually looking at a pathology image and correlating the image to genetic expression (e.g., identification of expression of oncogenes). The methods and compositions can be useful for identifying a cell from a population of cells, and determining the genetic heterogeneity of the cells within a sample. The methods and compositions can be useful for determining the genotype of a sample.

In some embodiments, performing the experiment comprises any immunoassay wherein cellular component targets are specifically bound by cellular component-binding reagents disclosed herein. A variety of immunoassay techniques, including competitive and non-competitive immunoassays, can be used. Immunoassays contemplated for use in the experiment encompasses techniques including, without limitation, flow cytometry, FACS, enzyme immunoassays (EIA), such as enzyme multiplied immunoassay technique (EMIT), enzyme-linked immunosorbent assay (ELISA), IgM antibody capture ELISA (MAC ELISA) and microparticle enzyme immunoassay (META), furthermore capillary electrophoresis immunoassays (CEIA), radio-immunoassays (RIA), immunoradiometric assays (IRMA), fluorescence polarization immunoassays (FPIA) and chemiluminescence assays (CL). If desired, such immunoassays can be automated. Immunoassays can also be used in conjunction with laser induced fluorescence. Further description of many of the methods above and additional immunoassay can be found in, e.g., Sambrook et al. (supra). In some embodiments, the cellular component-binding reagents disclosed herein comprise a primary antibody (e.g., an antibody that specifically binds to a cellular component target directly). In some embodiments, the cellular component-binding reagents disclosed herein comprise a secondary antibody (e.g., an antibody that specifically binds to a cellular component target indirectly, such as via binding to a primary antibody).

In some embodiments, performing an experiment comprises a qualitative and/or semi-quantitative immunoassay, such as, for example, immunoblotting or ELISA. In some embodiments, qualitative and semi-quantitative immunoassays provide information regarding the relative quantity of a cellular component target but fail to provide information regarding absolute the quantity of the cellular component target. Disclosed herein are methods of quantitative analysis of a plurality of cellular component targets using a qualitative and/or semi-quantitative immunoassay. In some embodiments, the methods comprise generating a titration curve, wherein several titration controls within the immunoassay (e.g., control lanes of a western blot or control wells of an ELISA) comprise a known concentration of cellular component target. These titration controls can be contacted with the cellular component-binding reagents disclosed herein for specific binding with the plurality of cellular component targets. Next, for each of these titration controls, the quantity of the detectable moiety of the cellular component-binding reagent specific oligonucleotide can be determined (e.g., by fluorescence analysis) as disclosed herein and the binding reagent oligonucleotide can be barcoded and sequenced as disclosed herein to determine the number of copies of each of the cellular component targets. Employing the relationship between the signal of the detectable moiety of the binding reagent oligonucleotide and the number of copies of each of the cellular component target at a variety of concentrations, one can develop a titration curve that will enable quantification of cellular targets in experimental immunoassay samples based on the signal of the detectable moiety of the binding reagent oligonucleotide. In alternative embodiments, a titration curve is not developed for the immunoassay, and each immunoassay sample (e.g., western blot lane, immunoblot spot (sections of a PVDF or nitrocellulose membrane), ELISA well) is subjected to the barcoding and sequencing of binding reagent oligonucleotides as disclosed herein to derive the number of copies of the cellular component target.

In some embodiments, performing the experiment comprises immunohistochemistry (e.g., "immunological staining"). Disclosed herein include methods of quantitative analysis of a plurality of cellular component targets of immunologically stained cells. In some embodiments, the method comprises contacting a sample (e.g., a tissue section) with the cellular component-binding reagents disclosed herein for specific binding with the plurality of cellular component targets on and/or within the tissue section. The tissue can be subjected to immunohistochemical analysis in order to obtain its morphological information and/or any other identifying features (such as presence or absence of rare cells). In some embodiments, a microscopy observation (e.g, fluorescence microscopy) of the tissue section is performed using the detectable moieties of the cellular component-binding reagent specific oligonucleotides associated with the cellular component-binding reagents, or lack thereof. In some embodiments, one or more portions of the tissue section identified by the microscopy observation as comprising cellular component targets of interest are excised, the binding reagent oligonucleotides are isolated, and are then contacted with a plurality of barcodes, wherein each of the plurality of barcodes comprises a target binding region and a molecular label sequence to generate barcodes hybridized to the cellular component-binding reagent specific oligonucleotides, or products thereof, followed by extending the barcodes hybridized to the cellular component-binding reagent specific oligonucleotides to produce a plurality of labeled nucleic acids, wherein each of the labeled nucleic acid comprises an identifier sequence, or a complementary sequence thereof, and a molecular label sequence, or a complementary sequence thereof, followed by obtaining sequence information of the plurality of labeled nucleic acids, complementary sequences thereof, portions thereof, or a combination thereof, to determine the number of copies of each of the cellular component targets of the cellular component-binding reagents associated with the cells of interest. Thus, the methods disclosed herein can determine the number and/or position of cellular component targets within immunologically stained cells (e.g., a tissue section).

Quantitative Analysis of a Plurality of Cellular Component Targets in Samples

Disclosed herein include methods of quantitative analysis of a plurality of cellular component targets in samples. In some embodiments, the method comprises: contacting a plurality of cellular component-binding reagents with a plurality of cellular component targets of a first sample and a second sample for specific binding with the plurality of cellular component targets, wherein each of the plurality of cellular component-binding reagents is associated with a cellular component-binding reagent specific oligonucleotide comprising a detectable moiety, or a precursor thereof, and a identifier sequence for the cellular component-binding reagent that the cellular component-binding reagent specific oligonucleotide is associated therewith, and wherein the cellular component-binding reagent is capable of specifically binding to a cellular component target of the plurality of cellular component targets, thereby generating cellular component targets of the plurality of cellular component targets associated with cellular component-binding reagents. The method can comprise determining a first quantity of the detectable moiety of the cellular component-binding reagent specific oligonucleotide associated with the cellular component-binding reagent associated with each of the plurality of cellular component targets in the first sample. The method can comprise contacting a plurality of barcodes with the cellular component-binding reagent specific oligonucleotides, or products thereof, associated with the cellular component-binding reagents associated with the cellular component targets of the first sample, wherein each of the plurality of barcodes comprises a target binding region and a molecular label sequence to generate barcodes hybridized to the cellular component-binding reagent specific oligonucleotides, or products thereof. The method can comprise extending the barcodes hybridized to the cellular component-binding reagent specific oligonucleotides, or products thereof, associated with the cellular component-binding reagents associated with the cellular component targets of the first sample to produce a plurality of labeled nucleic acids, wherein each of the labeled nucleic acid comprises an identifier sequence, or a complementary sequence thereof, and a molecular label sequence, or a complementary sequence thereof. The method can comprise obtaining sequence information of the plurality of labeled nucleic acids, complementary sequences thereof, portions thereof, or a combination thereof, to determine the number of copies of each of the cellular component targets of the first sample. The method can comprise determining a second quantity of the detectable moiety of the cellular component-binding reagent specific oligonucleotide associated with the cellular component-binding reagent associated with each of the plurality of cellular component targets in the second sample. The method can comprise determining the number of copies of each of the cellular component targets of the second sample based on (1) the first quantity of the detectable moiety of the cellular component-binding reagent specific oligonucleotide associated with the cellular component-binding reagent associated with each of the plurality of cellular component targets in the first sample, (2) the number of copies of each of the cellular component targets of the first sample determined, and (3) the second quantity of the detectable moiety of the cellular component-binding reagent specific oligonucleotide associated with the cellular component-binding reagent associated with each of the plurality of cellular component targets in the second sample. The method can comprise generating a standard curve of the correspondence between (1) the first quantity of the detectable moiety of the cellular component-binding reagent specific oligonucleotide associated with the cellular component-binding reagent associated with each of the plurality of cellular component targets in the first sample, and (2) the number of copies of each of the cellular component targets of the first sample determined; and using the standard curve to determine the number of copies of each of the cellular component targets of the second sample from (3) the second quantity of the detectable moiety of the cellular component-binding reagent specific oligonucleotide associated with the cellular component-binding reagent associated with each of the plurality of cellular component targets in the second sample.

In some embodiments, the number of copies of each of the cellular component targets of the second sample is inversely proportional to the first quantity of the moiety of the cellular component-binding reagent specific oligonucleotide associated with the cellular component-binding reagent associated with each of the plurality of cellular component targets in the first sample. In some embodiments, the number of copies of each of the cellular component targets of the second sample is directly proportional to the number of copies of each of the cellular component targets of the first sample determined. In some embodiments, the number of copies of each of the cellular component targets of the second sample is directly proportional to the second quantity of the moiety of the cellular component-binding reagent specific oligonucleotide associated with the cellular component-binding reagent associated with each of the plurality of cellular component targets in the second sampled.

In some embodiments, contacting a plurality of cellular component-binding reagents with a plurality of cellular component targets of a first sample and a second sample for specific binding with the plurality of cellular component targets comprises contacting intact cells of a first sample and a second sample with the plurality of cellular component-binding reagents. In some embodiments, contacting a plurality of cellular component-binding reagents with a plurality of cellular component targets of a first sample and a second sample for specific binding with the plurality of cellular component targets comprises contacting lysed cell contents of a first sample and a second sample with the plurality of cellular component-binding reagents. In some embodiments, contacting a plurality of cellular component-binding reagents with a plurality of cellular component targets of a first sample and a second sample for specific binding with the plurality of cellular component targets comprises contacting tissue sections of a first sample and a second sample with the plurality of cellular component-binding reagents.

In some embodiments, determining the quantity of the detectable moiety of the cellular component-binding reagent specific oligonucleotide comprises performing a microscopy observation (e.g., imaging) of the cells associated with the cellular component-binding reagents using the detectable moieties of the cellular component-binding reagent specific oligonucleotides associated with the cellular component-binding reagents. In some embodiments, determining the quantity of the detectable moiety of the cellular component-binding reagent specific oligonucleotide comprises performing flow cytometric analysis (e.g., with a fluorescence-based flow cytometry device) of the cells associated with the cellular component-binding reagents using the detectable moieties of the cellular component-binding reagent specific oligonucleotides associated with the cellular component-binding reagents.

Methods of Determining Whether a Cellular Constituent in a Sample Comprises a Cellular Component Target of Interest Disclosed herein include methods of determining whether a cellular constituent in a sample comprises a cellular component target of interest. Aspects of the methods of such embodiments include: producing a detectably labeled sample comprising a cellular component-binding reagent, wherein the cellular component-binding reagent is associated with a cellular component-binding reagent specific oligonucleotide associated with a detectable moiety and comprises an identifier sequence for the cellular component-binding reagent with which the cellular component-binding reagent specific oligonucleotide is associated, and wherein the cellular component-binding reagent is capable of specifically binding to the cellular component target of interest; and assaying cellular constituents of the detectably labeled sample for the detectable moiety to determine whether a cellular constituent in a cellular sample comprises the cellular component target of interest.

In such embodiments, the detectably labeled sample comprises a cellular component-binding reagent, wherein the cellular component-binding reagent is associated with a cellular component-binding reagent specific oligonucleotide associated with a detectable moiety and comprises an identifier sequence for the cellular component-binding reagent with which the cellular component-binding reagent specific oligonucleotide is associated, and wherein the cellular component-binding reagent is capable of specifically binding to the cellular component target of interest. The cellular component-binding reagent that is associated with a cellular component-binding reagent specific oligonucleotide associated with a detectable moiety may be any of such reagents as described above. According, the cellular component-binding reagent specific oligonucleotide may comprise the detectable moiety, e.g., as illustrated in FIG. 9. Alternatively, the cellular component-binding reagent specific oligonucleotide may be non-covalently bound to a label component, e.g., mediator, comprising the detectable moiety, such as a nucleic acid label that hybridizes to the cellular component-binding reagent specific oligonucleotide, such as the identifier sequence thereof, e.g., as illustrated in FIG. 12. The detectably labeled sample may be prepared using any convenient protocol, such as those described above. Where the cellular component-binding reagent is associated with the detectable moiety via a non-covalent binding mediator, such as a label nucleic acid, the non-covalent binding mediator may be bound to the oligonucleotide either before or after the oligonucleotide comprising cellular component-binding reagent is combined with the sample to produce the detectably labeled sample.

Following preparation of the detectably labeled sample, the methods may include assaying cellular constituents of the detectably labeled sample for the detectable moiety to determine whether a cellular constituent in a cellular sample comprises the cellular component target of interest. Assaying may be carried out using any convenient protocol, where in some instances the assaying comprises assessing cellular constituents of the detectably labeled sample and, for those constituents from which a signal of the detectable moiety is detected, determining that those cellular constituents comprise the cellular component target of interest, e.g., marker, such as described above. While any convenient protocol may be employed, in some instances the protocol is a cytometric protocol, such as flow cytometric protocol, e.g., as described above. In some instances, the methods may further comprise counting cellular constituents that comprise the cellular component target of interest. For example, the number of cellular constituents in a given detectably labeled sample that include the cellular component target of interest may be determined.

In some instances, methods of these embodiments may further comprise separating cellular constituents that comprise the cellular component target of interest from other constituents of the cellular sample. Separating may be accomplished using any convenient protocol. In some instances, separating comprises flow cytometrically sorting, e.g., as described above.

Where desired, the method may further include isolating a cellular constituent that comprises the cellular component target of interest into a single cell sample. Such isolating may be accomplished using any convenient protocol, such as but not limited to the partitioning protocols described above. As such, identified cells may be placed into a physical container, e.g., configured to hold a single cell, such as a microwell. Identified cells may be placed into a single droplet, e.g., configured to hold a single cell.

Where desired, the methods may further include producing barcoded identifier sequences from the single cell sample. Barcoded identifier sequences may be produced according to any convenient protocol, such as those protocols described above. As such, barcode identifier sequences may be produced by combining barcode nucleic acids with the oligonucleotides associated with the cellular component-binding reagent and processing to produce barcoded identifier sequences therefrom, e.g., by employing a protocol such as described above.

The produced barcoded identifier sequences may be further processed as desired. For example, the barcoded identifier sequences may be sequenced to obtain sequence information. Any convenient sequencing protocol may be employed, including Next Generation Sequence (NGS) sequencing protocols, e.g., as described above. The obtained sequence information may be employed for a variety of different purposes. For example, the obtained sequence information may be employed to quantitate the cellular component target of interest for the cellular constituent of the single cell sample, e.g., as described above. Where desired, the methods may also include sequence analysis of nucleic acids of the single cell, such as sequence analysis of the mRNAs of the single cell, including analysis of the transcriptome or a portion thereof of the single cell. Analysis of the transcriptome or portion thereof may be performed using any convenient protocol, such as those described above.

The above methods may be employed to determine whether a cellular constituent in a sample comprises a single cellular component target of interest, or two or more distinct cellular component targets of interest. While the number of distinct cellular component targets of interest that may be assayed by the methods may vary, in some instances the number may range from one to ten, such as two to five, e.g., three to four. Cellular constituents may be assayed for one or more cellular component targets of interest using suitable populations/cocktails of cellular component-binding reagents, e.g., as described above. In some instances, the population/cocktail employed in such methods includes one or more oligonucleotide comprising cellular component-binding reagents in which the oligonucleotide is not associated with a detectable moiety. In such embodiments, the number of such oligonucleotide comprising cellular component-binding reagents that lack a detectable moiety may vary, ranging in some instances from 1 to 500, such as 3 to 300, including 5 to 100, e.g., 10 to 50. Oligonucleotide comprising cellular component-binding reagents that lack a detectable moiety may be employed in embodiments where one desires to assess one or more cellular component targets of interest that are not employed to distinguish, e.g., sort, certain cellular constituents from other cellular constituents in a sample. In some instances, the number of oligonucleotide-comprising cellular component-binding reagents that lack a detectable moiety exceeds the number that include a detectable moiety.

Use of cellular component-binding reagents associated with oligonucleotides associated with detectable moieties provides for a number of advantages in cell sorting/nucleic acid analysis workflows. For example, in traditional methods of cell sorting, labeled antibodies are employed in conjunction with oligonucleotide-associated antibodies. Specifically, labeled antibodies may be employed in a first sorting step to enrich for one or more populations of interest. The resultant enriched population of cells may then be contacted with oligonucleotide associated antibodies for further analysis. In such instances, a given cellular component target may be employed for both sorting and subsequent analysis. When this occurs, users separately design and prepare a fluorescent antibody panel and an oligo-conjugated antibody panel to be stained concurrently or sequentially. When there are overlapping clones in both panels, the fluorophore-conjugated antibodies and the oligo-conjugated antibodies will compete for available epitopes and signal from both detection methods may be decreased. Methods as described above mitigate this issue by associated a detectable moiety with the oligonucleotide of the cellular component-binding reagent, so that the same reagent oligonucleotide comprising cellular component-binding reagent may be employed for both sorting and other analysis.

Figure 13:
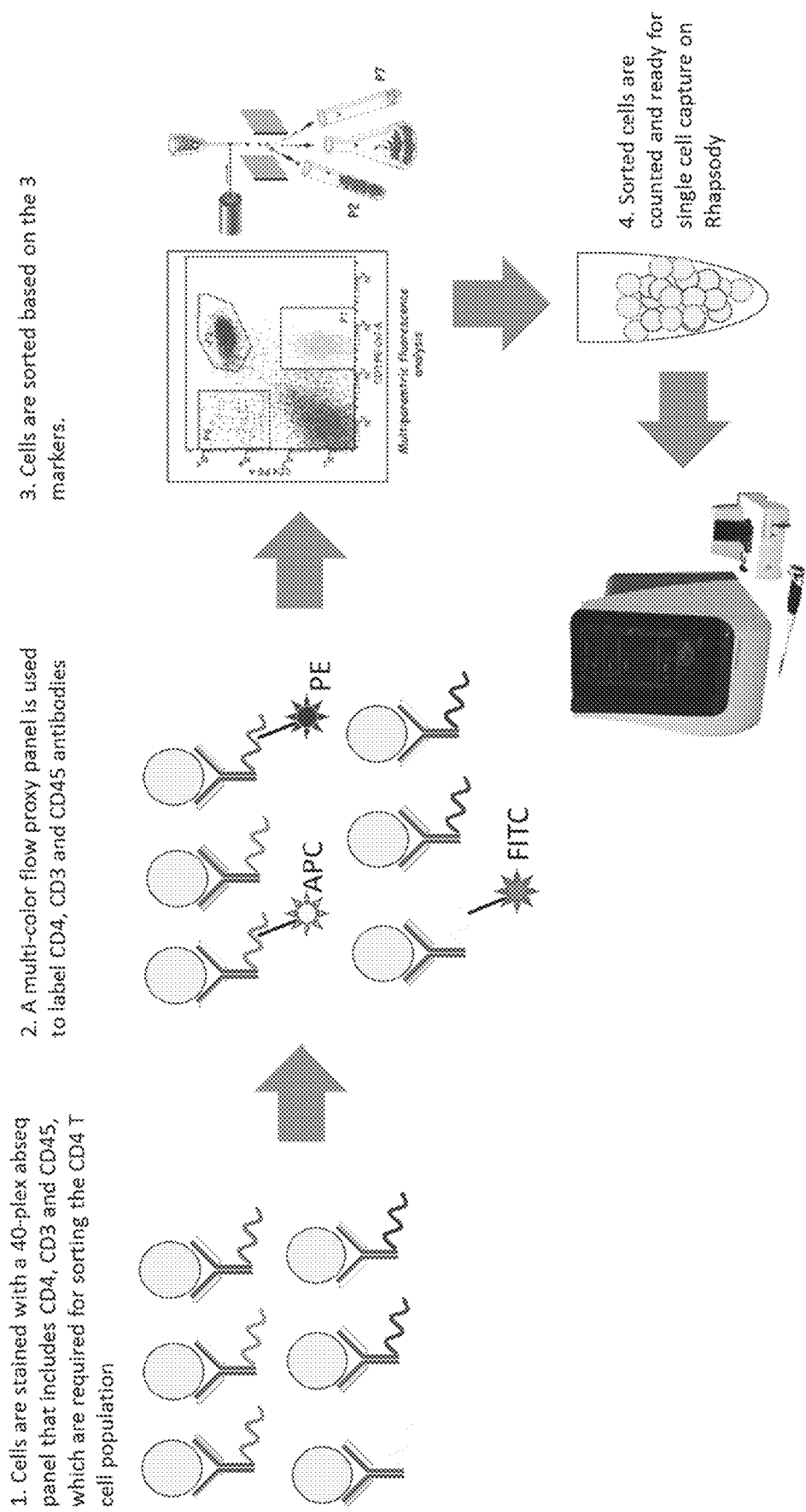
FIG. 13 shows a schematic illustration of a non-limiting exemplary workflow for digital mRNA and protein analysis cellular analysis.

FIG. 13 provides an example of a workflow for performing digital mRNA and protein quantification, such as described above, using BD AbSeq oligonucleotide comprising antibodies on the BD Rhapsody high throughput single cell capture system (BD Biosciences, San Jose, CA). As illustrated in FIG. 13, a cellular sample is stained with a multiplexed AbSeq oligonucleotide comprising antibody panel (e.g., 40-plex), where the identifiers of the oligonucleotides of the antibodies that specifically bind to CD3, CD4 and CD45 are hybridized to distinguishably fluorescently labeled label nucleic acids, e.g., a label nucleic acid that hybridizes to the identifier of the CD3 antibody and comprises APC, a label nucleic acid that hybridizes to the identifier of the CD4 antibody and comprises PE, and a label nucleic acid that hybridizes to the identifier of the CD45 antibody and comprises FITC. The resultant labeled sample is then flow cytometrically sorted based on the APC, PE and FITC to obtain a CD4 T Cell population. The resultant sorted cells are then counted and further processed with the BD Rhapsody high throughput single cell capture system. While FIG. 13 illustrates the workflow using label nucleic acids to associate the detectable moiety with the antibody oligonucleotide, the antibody oligonucleotide may also comprise the detectable moiety, e.g., as illustrated in FIG. 9.

Compositions and Kits

Aspects of the invention further include kits and compositions that find use in practicing various methods of the invention.

Some embodiments disclosed herein provide kits and compositions for simultaneous quantitative analysis of a plurality of cellular components (e.g., proteins) and/or a plurality of nucleic acid target molecules in a sample. The kits and compositions can, in some embodiments, comprise a plurality of cellular component binding reagents (e.g., a plurality of protein binding reagents) each conjugated with an oligonucleotide, wherein the oligonucleotide comprises a unique identifier for the cellular component binding reagent, and a plurality of oligonucleotide probes, wherein each of the plurality of oligonucleotide probes comprises a target binding region, a barcode sequence (e.g., a molecular label sequence), wherein the barcode sequence is from a diverse set of unique barcode sequences. In some embodiments, each of the oligonucleotides can comprise a molecular label, a cell label, a sample label, or any combination thereof. In some embodiments, each of the oligonucleotides can comprise a linker. In some embodiments, each of the oligonucleotides can comprise a binding site for an oligonucleotide probe, such as a poly(A) tail. For example, the poly(A) tail can be, e.g., oligodA$_{18}$ (unanchored to a solid support) or oligoA$_{18}$V (anchored to a solid support). The oligonucleotides can comprise DNA residues, RNA residues, or both.

In some instances, an oligonucleotide of a cellular component-binding reagent, e.g., as described above, is associated with a detectable moiety, such as a fluorescent moiety. As reviewed above, the oligonucleotide may comprise the detectable moiety or be non-covalently bound to a mediate that comprises the detectable moiety, e.g., a label nucleic acid that comprises the detectable moiety. While the number of distinct oligonucleotide comprising cellular component-binding reagents may vary, in some instances the number ranges from one to ten, such as two to five, e.g., three to four. In some instances, the kit comprises a population/cocktail that includes one or more oligonucleotide comprising cellular component-binding reagents in which the oligonucleotide is not associated with a detectable moiety. In such embodiments, the number of such oligonucleotide comprising cellular component-binding reagents that lack a detectable moiety may vary, ranging in some instances from 1 to 500, such as 3 to 300, including 5 to 100, e.g., 10 to 50. Oligonucleotide comprising cellular component-binding reagents that lack a detectable moiety may be present where one desires to assess one or more cellular component targets of interest that are not employed to distinguish, e.g., sort, certain cellular constituents from other cellular constituents in a sample. In some instances, the number of oligonucleotide-comprising cellular component-binding reagents that lack a detectable moiety exceeds the number that include a detectable moiety.

Disclosed herein include a plurality of sample indexing compositions. Each of the plurality of sample indexing compositions can comprise two or more cellular component binding reagents. Each of the two or more cellular component binding reagents can be associated with a sample indexing oligonucleotide. At least one of the two or more cellular component binding reagents can be capable of specifically binding to at least one cellular component target. The sample indexing oligonucleotide can comprise a sample indexing sequence for identifying sample origin of one or more cells of a sample. Sample indexing sequences of at least two sample indexing compositions of the plurality of sample indexing compositions can comprise different sequences.

Disclosed herein include kits comprising sample indexing compositions for cell identification. In some embodiments. Each of two sample indexing compositions comprises a cellular component binding reagent (e.g., a protein binding reagent) associated with a sample indexing oligonucleotide, wherein the cellular component binding reagent is capable of specifically binding to at least one of one or more cellular component targets (e.g., one or more protein targets), wherein the sample indexing oligonucleotide comprises a sample indexing sequence, and wherein sample indexing sequences of the two sample indexing compositions comprise different sequences. In some embodiments, the sample indexing oligonucleotide comprises a molecular label sequence, a binding site for a universal primer, or a combination thereof.

Disclosed herein include kits for cell identification. In some embodiments, the kit comprises: two or more sample indexing compositions. Each of the two or more sample indexing compositions can comprise a cellular component binding reagent (e.g., an antigen binding reagent) associated with a sample indexing oligonucleotide, wherein the cellular component binding reagent is capable of specifically binding to at least one of one or more cellular component targets, wherein the sample indexing oligonucleotide comprises a sample indexing sequence, and wherein sample indexing sequences of the two sample indexing compositions comprise different sequences. In some embodiments, the sample indexing oligonucleotide comprises a molecular label sequence, a binding site for a universal primer, or a combination thereof. Disclosed herein include kits for multiplet identification. In some embodiments, the kit comprises two sample indexing compositions. Each of two sample indexing compositions can comprise a cellular component binding reagent (e.g., an antigen binding reagent) associated with a sample indexing oligonucleotide, wherein the antigen binding reagent is capable of specifically binding to at least one of one or more cellular component targets (e.g., antigen targets), wherein the sample indexing oligonucleotide comprises a sample indexing sequence, and wherein sample indexing sequences of the two sample indexing compositions comprise different sequences.

The unique identifiers (or oligonucleotides associated with cellular component binding reagents, such as binding reagent oligonucleotides, antibody oligonucleotides, sample indexing oligonucleotides, cell identification oligonucleotides, control particle oligonucleotides, control oligonucleotides, or interaction determination oligonucleotides) can have any suitable length, for example, from about 25 nucleotides to about 45 nucleotides long. In some embodiments, the unique identifier can have a length that is, is about, is less than, is greater than, 4 nucleotides, 5 nucleotides, 6 nucleotides, 7 nucleotides, 8 nucleotides, 9 nucleotides, 10 nucleotides, 15 nucleotides, 20 nucleotides, 25 nucleotides, 30 nucleotides, 35 nucleotides, 40 nucleotides, 45 nucleotides, 50 nucleotides, 55 nucleotides, 60 nucleotides, 70 nucleotides, 80 nucleotides, 90 nucleotides, 100 nucleotides, 200 nucleotides, or a range that is between any two of the above values.

In some embodiments, the unique identifiers are selected from a diverse set of unique identifiers. The diverse set of unique identifiers can comprise, or comprise about, 20, 30, 40, 50, 60, 70, 80, 90, 100, 200, 300, 400, 500, 600, 700, 800, 900, 1000, 2000, 5000, or a number or a range between any two of these values, different unique identifiers. The diverse set of unique identifiers can comprise at least, or comprise at most, 20, 30, 40, 50, 60, 70, 80, 90, 100, 200, 300, 400, 500, 600, 700, 800, 900, 1000, 2000, or 5000, different unique identifiers. In some embodiments, the set of unique identifiers is designed to have minimal sequence homology to the DNA or RNA sequences of the sample to be analyzed. In some embodiments, the sequences of the set of unique identifiers are different from each other, or the complement thereof, by, or by about, 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, or a number or a range between any two of these values. In some embodiments, the sequences of the set of unique identifiers are different from each other, or the complement thereof, by at least, or by at most, 1 nucleotide, 2 nucleotides, 3 nucleotides, 4 nucleotides, 5 nucleotides, 6 nucleotides, 7 nucleotides, 8 nucleotides, 9 nucleotides, or 10 nucleotides.

In some embodiments, the unique identifiers can comprise a binding site for a primer, such as universal primer. In some embodiments, the unique identifiers can comprise at least two binding sites for a primer, such as a universal primer. In some embodiments, the unique identifiers can comprise at least three binding sites for a primer, such as a universal primer. The primers can be used for amplification of the unique identifiers, for example, by PCR amplification. In some embodiments, the primers can be used for nested PCR reactions.

Any suitable cellular component binding reagents are contemplated in this disclosure, such as any protein binding reagents (e.g., antibodies or fragments thereof, aptamers, small molecules, ligands, peptides, oligonucleotides, etc., or any combination thereof). In some embodiments, the cellular component binding reagents can be polyclonal antibodies, monoclonal antibodies, recombinant antibodies, single-chain antibody (scAb), or fragments thereof, such as Fab, Fv, etc. In some embodiments, the plurality of protein binding reagents can comprise, or comprise about, 20, 30, 40, 50, 60, 70, 80, 90, 100, 200, 300, 400, 500, 600, 700, 800, 900, 1000, 2000, 5000, or a number or a range between any two of these values, different protein binding reagents. In some embodiments, the plurality of protein binding reagents can comprise at least, or comprise at most, 20, 30, 40, 50, 60, 70, 80, 90, 100, 200, 300, 400, 500, 600, 700, 800, 900, 1000, 2000, or 5000, different protein binding reagents.

In some embodiments, the oligonucleotide is conjugated with the cellular component binding reagent through a linker. In some embodiments, the oligonucleotide can be conjugated with the protein binding reagent covalently. In some embodiment, the oligonucleotide can be conjugated with the protein binding reagent non-covalently. In some embodiments, the linker can comprise a chemical group that reversibly or irreversibly attached the oligonucleotide to the protein binding reagents. The chemical group can be conjugated to the linker, for example, through an amine group. In some embodiments, the linker can comprise a chemical group that forms a stable bond with another chemical group conjugated to the protein binding reagent. For example, the chemical group can be a UV photocleavable group, a disulfide bond, a streptavidin, a biotin, an amine, etc. In some embodiments, the chemical group can be conjugated to the protein binding reagent through a primary amine on an amino acid, such as lysine, or the N-terminus. The oligonucleotide can be conjugated to any suitable site of the protein binding reagent, as long as it does not interfere with the specific binding between the protein binding reagent and its protein target. In embodiments where the protein binding reagent is an antibody, the oligonucleotide can be conjugated to the antibody anywhere other than the antigen-binding site, for example, the Fc region, the $C_H1$ domain, the $C_H2$ domain, the $C_H3$ domain, the CL domain, etc. In some embodiments, each protein binding reagent can be conjugated with a single oligonucleotide molecule. In some embodiments, each protein binding reagent can be conjugated with, or with about, 2, 3, 4, 5, 10, 20, 30, 40, 50, 100, 1000, or a number or a range between any two of these values, oligonucleotide molecules, wherein each of the oligonucleotide molecule comprises the same unique identifier. In some embodiments, each protein binding reagent can be conjugated with more than one oligonucleotide molecule, for example, at least, or at most, 2, 3, 4, 5, 10, 20, 30, 40, 50, 100, or 1000, oligonucleotide molecules, wherein each of the oligonucleotide molecule comprises the same unique identifier.

In some embodiments, the plurality of cellular component binding reagents (e.g., protein binding reagents) are capable of specifically binding to a plurality of cellular component targets (e.g., protein targets) in a sample. The sample can be, or comprise, a single cell, a plurality of cells, a tissue sample, a tumor sample, a blood sample, or the like. In some embodiments, the plurality of cellular component targets comprises a cell-surface protein, a cell marker, a B-cell receptor, a T-cell receptor, an antibody, a major histocompatibility complex, a tumor antigen, a receptor, or any combination thereof. In some embodiments, the plurality of cellular component targets can comprise intracellular proteins. In some embodiments, the plurality of cellular component targets can comprise intracellular proteins. In some embodiments, the plurality of cellular component targets can be, or be about, 1%, 2%, 3%, 4%, 5%, 6%, 7%, 8%, 9%, 10%, 20%, 30%, 40%, 50%, 60%, 70%, 80%, 90%, 95%, 98%, 99%, or a number or a range between any two of these values of all cellular component targets (e.g., proteins expressed or could be expressed) in an organism. In some embodiments, the plurality of cellular component targets can be at least, or be at most, 1%, 2%, 3%, 4%, 5%, 6%, 7%, 8%, 9%, 10%, 20%, 30%, 40%, 50%, 60%, 70%, 80%, 90%, 95%, 98%, or 99%, of all cellular component targets (e.g., proteins expressed or could be expressed) in an organism. In some embodiments, the plurality of cellular component targets can comprise, or comprise about, 2, 3, 4, 5, 10, 20, 30, 40, 50, 100, 1000, 10000, or a number or a range between any two of these values, different cellular component targets. In some embodiments, the plurality of cellular component targets can comprise at least, or comprise at most, 2, 3, 4, 5, 10, 20, 30, 40, 50, 100, 1000, or 10000, different cellular component targets.

Components of the kits may be present in separate containers, or multiple components may be present in a single container.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

EXAMPLES

Some aspects of the embodiments discussed above are disclosed in further detail in the following examples, which are not in any way intended to limit the scope of the present disclosure.

Example 1

Oligonucleotides for Associating with Protein Binding Reagents

This example demonstrates designing of oligonucleotides that can be conjugated with protein binding reagents. The oligonucleotides can be used to determine protein expression and gene expression simultaneously. The oligonucleotides can also be used for sample indexing to determine cells of the same or different samples.
95mer Oligonucleotide Design The following method was used to generate candidate oligonucleotide sequences and corresponding primer sequences for simultaneous determination of protein expression and gene expression or sample indexing.

1. Sequence Generation and Elimination

The following process was used to generate candidate oligonucleotide sequences for simultaneous determination of protein expression and gene expression or sample indexing.

Step 1a. Randomly generate a number of candidate sequences (50000 sequences) with the desired length (45 bps).

Step 1b. Append the transcriptional regulator LSRR sequence to the 5' end of the sequences generated and a poly(A) sequence (25 bps) to the 3' end of the sequences generated.

Step 1c. Remove sequences generated and appended that do not have GC contents in the range of 40% to 50%.

Step 1d. Remove remaining sequences with one or more hairpin structures each.

The number of remaining candidate oligonucleotide sequences was 423.

2. Primer Design

The following method was used to design primers for the remaining 423 candidate oligonucleotide sequences.

2.1 N1 Primer: Use the universal N1 sequence: 5'-GTTGTCAAGATGCTACCGTTCAGAG-3' (LSRR sequence; SEQ ID NO. 3) as the N1 primer.

2.2 N2 Primer (for amplifying specific sample index oligonucleotides; e.g., N2 primer in FIGS. 10B-10D):

2.2a. Remove candidate N2 primers that do not start downstream of the N1 sequence.

2.2b. Remove candidate N2 primers that overlap in the last 35 bps of the candidate oligonucleotide sequence.

2.2c. Remove the primer candidates that are aligned to the transcriptome of the species of cells being studied using the oligonucleotides (e.g., the human transcriptome or the mouse transcriptome).

2.2d. Use the ILR2 sequence as the default control (ACACGACGCTCTTCCGATCT; SEQ ID NO. 4) to minimize or avoid primer-primer interactions.

Of the 423 candidate oligonucleotide sequences, N2 primers for 390 candidates were designed.

3. Filtering

The following process was used to filter the remaining 390 candidate primer sequences.

3a. Eliminate any candidate oligonucleotide sequence with a random sequence ending in As (i.e., the effective length of the poly(A) sequence is greater than 25 bps) to keep poly(A) tail the same length for all barcodes.

3b. Eliminate any candidate oligonucleotide sequences with 4 or more consecutive Gs (>3Gs) because of extra cost and potentially lower yield in oligo synthesis of runs of Gs.

FIG. 10A shows a non-limiting exemplary candidate oligonucleotide sequence generated using the method above.
200mer Oligonucleotide Design The following method was used to generate candidate oligonucleotide sequences and corresponding primer sequences for simultaneous determination of protein expression and gene expression and sample indexing.

1. Sequence Generation and Elimination

The following was used to generate candidate oligonucleotide sequences for simultaneous determination of protein expression and gene expression and sample indexing.

1a. Randomly generate a number of candidate sequences (100000 sequences) with the desired length (128 bps).

1b. Append the transcriptional regulator LSRR sequence and an additional anchor sequence that is non-human, non-mouse to the 5' end of the sequences generated and a poly(A) sequence (25 bps) to the 3' end of the sequences generated.

1c. Remove sequences generated and appended that do not have GC contents in the range of 40% to 50%.

1d. Sort remaining candidate oligonucleotide sequences based on hairpin structure scores.

1e. Select 1000 remaining candidate oligonucleotide sequences with the lowest hairpin scores.

2. Primer Design

The following method was used to design primers for 400 candidate oligonucleotide sequences with the lowest hairpin scores.

2.1 N1 Primer: Use the universal N1 sequence: 5'-GTTGTCAAGATGCTACCGTTCAGAG-3' (LSRR sequence; SEQ ID NO. 3) as the N1 primer.

2.2 N2 Primer (for amplifying specific sample index oligonucleotides; e.g., N2 primer in FIGS. 10B and 10C):

2.2a. Remove candidate N2 primers that do not start 23 nts downstream of the N1 sequence (The anchor sequence was universal across all candidate oligonucleotide sequences).

2.2b. Remove candidate N2 primers that overlap in the last 100 bps of the target sequence. The resulting primer candidates can be between the 48th nucleotide and 100th nucleotide of the target sequence.

2.2c. Remove the primer candidates that are aligned to the transcriptome of the species of cells being studied using the oligonucleotides (e.g., the human transcriptome or the mouse transcriptome).

2.2d. Use the ILR2 sequence, 5'-ACACGACGCTCTTCCGATCT-3' (SEQ ID NO. 4) as the default control to minimize or avoid primer-primer interactions.

2.2e. Remove N2 primer candidates that overlap in the last 100 bps of the target sequence.

Of the 400 candidate oligonucleotide sequences, N2 primers for 392 candidates were designed.

3. Filtering

The following was used to filter the remaining 392 candidate primer sequences.

3a. Eliminate any candidate oligonucleotide sequence with a random sequence ending in As (i.e., the effective length of the poly(A) sequence is greater than 25 bps) to keep poly(A) tail the same length for all barcodes.

3b. Eliminate any candidate oligonucleotide sequences with 4 or more consecutive Gs (>3Gs) because of extra cost and potentially lower yield in oligo synthesis of runs of Gs.

FIG. 10B shows a non-limiting exemplary candidate oligonucleotide sequence generated using the method above. The nested N2 primer shown in FIG. 10B can bind to the antibody or sample specific sequence for targeted amplification. FIG. 10C shows the same non-limiting exemplary candidate oligonucleotide sequence with a nested universal N2 primer that corresponds to the anchor sequence for targeted amplification. FIG. 10D shows the same non-limiting exemplary candidate oligonucleotide sequence with a N2 primer for one step targeted amplification.

Altogether, these data indicate that oligonucleotide sequences of different lengths can be designed for simultaneous determination of protein expression and gene expression or sample indexing. The oligonucleotide sequences can include a universal primer sequence, an antibody specific oligonucleotide sequence or a sample indexing sequence, and a poly(A) sequence.

Example 2

Oligonucleotide-Associated Antibody Workflow

This example demonstrates a workflow of using an oligonucleotide-conjugated antibody for determining the expression profile of a protein target.

Figure 11:
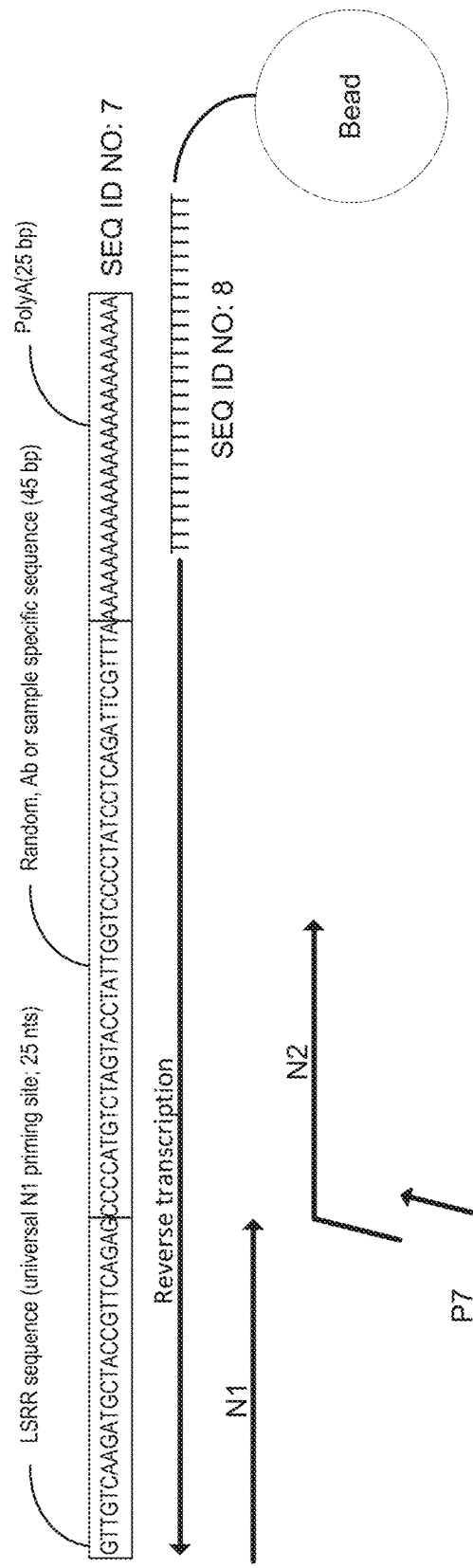
FIG. 11 shows a schematic illustration of a non-limiting exemplary oligonucleotide sequence for determining protein expression and gene expression simultaneously and for sample indexing.

Frozen cells (e.g., frozen peripheral blood mononuclear cells (PBMCs)) of a subject are thawed. The thawed cells are stained with an oligonucleotide-conjugated antibody (e.g., an anti-CD4 antibody at 0.06 µg/100 µl (1:333 dilution of an oligonucleotide-conjugated antibody stock)) at a temperature for a duration (e.g., room temperature for 20 minutes). The oligonucleotide-conjugated antibody is conjugated with 1, 2, or 3 oligonucleotides ("antibody oligonucleotides"). The sequence of the antibody oligonucleotide is shown in FIG. 11. The cells are washed to remove unbound oligonucleotide-conjugated antibody. The cells are optionally stained with Calcein AM (BD (Franklin Lake, NJ)) and Drag7™ (Abcam (Cambridge, United Kingdom)) for sorting with flow cytometry to obtain cells of interest (e.g., live cells). The cells are optionally washed to remove excess Calcein AM and Drag7™. Single cells stained with Calcein AM (live cells) and not Drag7™ (cells that are not dead or permeabilized) are sorted, using flow cytometry, into a BD Rhapsody™ cartridge.

Of the wells containing a single cell and a bead, the single cells in the wells (e.g., 3500 live cells) are lysed in a lysis buffer (e.g., a lysis buffer with 5 mM DTT). The mRNA expression profile of a target (e.g., CD4) is determined using BD Rhapsody™ beads. The protein expression profile of a target (e.g., CD4) is determined using BD Rhapsody™ beads and the antibody oligonucleotides. Briefly, the mRNA molecules are released after cell lysis. The Rhapsody™ beads are associated with barcodes (e.g., stochastic barcodes) each containing a molecular label, a cell label, and an oligo(dT) region. The poly(A) regions of the mRNA molecules released from the lysed cells hybridize to the poly(T) regions of the stochastic barcodes. The poly(dA) regions of the antibody oligonucleotides hybridize to the oligo(dT) regions of the barcodes. The mRNA molecules were reverse transcribed using the barcodes. The antibody oligonucleotides are replicated using the barcodes. The reverse transcription and replication optionally occur in one sample aliquot at the same time.

The reverse transcribed products and replicated products are PCR amplified using primers for determining mRNA expression profiles of genes of interest, using N1 primers, and the protein expression profile of a target, using the antibody oligonucleotide N1 primer. For example, the reverse transcribe products and replicated products can be PCR amplified for 15 cycles at 60 degrees annealing temperature using primers for determining the mRNA expression profiles of 488 blood panel genes, using blood panel N1 primers, and the expression profile of CD4 protein, using the antibody oligonucleotide N1 primer ("PCR 1"). Excess barcodes are optionally removed with Ampure cleanup. The products from PCR 1 are optionally divided into two aliquots, one aliquot for determining the mRNA expression profiles of the genes of interest, using the N2 primers for the genes of interest, and one aliquot for determining the protein expression profile of the target of interest, using the antibody oligonucleotide N2 primer ("PCR 2"). Both aliquots are PCR amplified (e.g., for 15 cycles at 60 degrees annealing temperature). The protein expression of the target in the cells are determined based on the antibody oligonucleotides as illustrated in FIG. 11 ("PCR 2"). Sequencing data is obtained and analyzed after sequencing adaptor addition ("PCR 3"), such as sequencing adaptor ligation. Cell types are determined based on the mRNA expression profiles of the genes of interest.

Altogether, this example describes using an oligonucleotide-Conjugated antibody for determining the protein expression profile of a target of interest. This example further describes that the protein expression profile of the target of interest and the mRNA expression profiles of genes of interest can be determine simultaneously.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A method of determining whether a cellular constituent in a sample comprises a cellular component target of interest, the method comprising:
producing a luminescent labeled sample comprising a cellular component-binding reagent, wherein the cellular component-binding reagent is associated with a cellular component-binding reagent specific oligonucleotide associated with a luminescent moiety and comprises an identifier sequence for the cellular component-binding reagent with which the cellular component-binding reagent specific oligonucleotide is associated, wherein the cellular component-binding reagent comprises an antibody or specific binding fragment thereof capable of specifically binding to the cellular component target of interest, and wherein the cellular component-binding reagent is not associated with a solid support; and
assaying cellular constituents of the luminescent labeled sample for the luminescent moiety to determine whether a cellular constituent in a cellular sample comprises the cellular component target of interest;
wherein the assaying comprises flow cytometrically sorting cells based on the luminescent moiety; and
wherein the cellular component-binding reagent specific oligonucleotide comprises the luminescent moiety or the identifier sequence in the cellular component-binding reagent specific oligonucleotide is hybridized to a label component comprising the luminescent moiety.

2. The method according to claim 1, wherein the cellular component-binding reagent specific oligonucleotide comprises the luminescent moiety.

3. The method according to claim 1, wherein the label nucleic acid comprising the luminescent moiety is hybridized to the identifier sequence for the cellular component-binding reagent.

4. The method according to claim 1, wherein the luminescent moiety comprises a fluorescent moiety.

5. The method according to claim 1, wherein the assaying comprises flow cytometrically assaying the detectably labeled sample.

6. The method according to claim 1, wherein the method further comprises counting cellular constituents that comprise the cellular component target of interest.

7. The method according to claim 1, wherein the method further comprises separating cellular constituents that comprise the cellular component target of interest from other constituents of the cellular sample.

8. The method according to claim 1, wherein the cellular component target of interest is a cell surface marker.

9. The method according to claim 1, wherein the method further comprises isolating a cellular constituent that comprises the cellular component target of interest into a single cell sample.

10. The method according to claim 9, wherein the method further comprises producing barcoded identifier sequences from the single cell sample.

11. The method according to claim 10, wherein the method further comprises sequencing the barcoded identifier sequences.

12. The method according to claim 11, wherein the barcoded identifier sequences are sequenced using a next generation sequencing (NGS) protocol.

13. The method according to claim 12, wherein the method further comprises quantitating the cellular component target of interest for the cellular constituent of the single cell sample from the sequence information.

14. The method according to claim 1, wherein the method further comprises analysis of the transcriptome or a portion thereof of cellular constituents of the cellular sample that comprise the cellular component target of interest.

15. The method of claim 1, wherein the method further comprises counting cellular constituents that comprise the cellular component target of interest based on the detectable moiety.

16. The method of claim 1, wherein the method further comprises counting cellular constituents that comprise the cellular component target of interest based on the identifier sequence.

17. The method of claim 1, wherein the sample comprises a mixed population of cells.

18. The method of claim 1, wherein the cellular constituents of the sample are labeled with a plurality of cellular component-binding reagents comprising a cellular component-binding reagent specific oligonucleotide with an identifier sequence that is not associated with the luminescent moiety.

19. The method of claim 18, further comprising assaying the cellular constituents of the luminescent labeled sample for the plurality of cellular component-binding reagents comprising the cellular component-binding reagent specific oligonucleotide with an identifier sequence that is not associated with the luminescent moiety.

* * * * *

SEQUENCE LISTING

```
<160> NUMBER OF SEQ ID NOS: 10

<210> SEQ ID NO 1
<211> LENGTH: 16
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(16)
<223> OTHER INFORMATION: n is a, c, g, or t
```

<400> SEQUENCE: 1
nnnnnnnnnn nnnnn                                                                  16

<210> SEQ ID NO 2
<211> LENGTH: 12
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(12)
<223> OTHER INFORMATION: n is a, c, g, or t

<400> SEQUENCE: 2
nnnnnnnnnn nn                                                                     12

<210> SEQ ID NO 3
<211> LENGTH: 25
<212> TYPE: DNA
<213> ORGANISM: Artificial sequence
<220> FEATURE:
<223> OTHER INFORMATION: synthetic sequence

<400> SEQUENCE: 3
gttgtcaaga tgctaccgtt cagag                                                       25

<210> SEQ ID NO 4
<211> LENGTH: 20
<212> TYPE: DNA
<213> ORGANISM: Artificial sequence
<220> FEATURE:
<223> OTHER INFORMATION: synthetic sequence

<400> SEQUENCE: 4
acacgacgct cttccgatct                                                             20

<210> SEQ ID NO 5
<211> LENGTH: 12
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(12)
<223> OTHER INFORMATION: n is a, c, g, or t

<400> SEQUENCE: 5
nnnnnnnnnn nn                                                                     12

<210> SEQ ID NO 6
<211> LENGTH: 12
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(12)
<223> OTHER INFORMATION: n is a, c, g, or t

<400> SEQUENCE: 6
nnnnnnnnnn nn                                                                     12

<210> SEQ ID NO 7

```
<211> LENGTH: 95
<212> TYPE: DNA
<213> ORGANISM: Artificial sequence
<220> FEATURE:
<223> OTHER INFORMATION: synthetic sequence

<400> SEQUENCE: 7
gttgtcaaga tgctaccgtt cagagcccca tgtctagtac ctattggtcc cctatcctca      60
gattcgttta aaaaaaaaaa aaaaaaaaaa aaaaa                                 95

<210> SEQ ID NO 8
<211> LENGTH: 26
<212> TYPE: DNA
<213> ORGANISM: Artificial sequence
<220> FEATURE:
<223> OTHER INFORMATION: synthetic sequence

<400> SEQUENCE: 8
tttttttttt tttttttttt tttttt                                           26

<210> SEQ ID NO 9
<211> LENGTH: 95
<212> TYPE: DNA
<213> ORGANISM: Artificial sequence
<220> FEATURE:
<223> OTHER INFORMATION: synthetic sequence

<400> SEQUENCE: 9
gttgtcaaga tgctaccgtt cagagtacgt ggagttggtg gcccgacccc gagcgctacg      60 agcccccgg aaaaaaaaaa aaaaaaaaaa aaaaa                                  95

<210> SEQ ID NO 10
<211> LENGTH: 200
<212> TYPE: DNA
<213> ORGANISM: Artificial sequence
<220> FEATURE:
<223> OTHER INFORMATION: synthetic sequence

<400> SEQUENCE: 10
gttgtcaaga tgctaccgtt cagagctact gtccgaagtt accgtgtatc taccacgggt      60
ggtttttcga atccggaaaa gatagtaata agtgttttag ttggaataag tcgcaacttt     120
tggagacggt tacctctcaa tttttctgat ccgtaggccc cccgatctcg gcctcaaaaa     180
aaaaaaaaaa aaaaaaaaa                                                  200
```